(12) United States Patent
Takahashi et al.

(10) Patent No.: US 8,106,086 B2
(45) Date of Patent: Jan. 31, 2012

(54) INDOLEDIONE DERIVATIVE

(75) Inventors: Toshiyuki Takahashi, Tsukuba (JP);
Tsuyoshi Nagase, Tokushima (JP);
Nagaaki Sato, Saitama (JP)

(73) Assignee: MSD K.K., Tokyo (JP)

( * ) Notice: Subject to any disclaimer, the term of this patent is extended or adjusted under 35 U.S.C. 154(b) by 262 days.

(21) Appl. No.: 12/532,182

(22) PCT Filed: Mar. 27, 2008

(86) PCT No.: PCT/JP2008/055825
§ 371 (c)(1),
(2), (4) Date: Sep. 21, 2009

(87) PCT Pub. No.: WO2008/120653
PCT Pub. Date: Oct. 9, 2008

(65) Prior Publication Data
US 2010/0056597 A1 Mar. 4, 2010

(30) Foreign Application Priority Data
Apr. 2, 2007 (JP) .................................. 2007-096690

(51) Int. Cl.
*A61K 31/4155* (2006.01)
*C07D 403/02* (2006.01)

(52) U.S. Cl. ..................................... 514/407; 548/364.7

(58) Field of Classification Search ........................ None
See application file for complete search history.

(56) References Cited

U.S. PATENT DOCUMENTS
7,491,381 B2 2/2009 Kotani et al.

FOREIGN PATENT DOCUMENTS
WO 94/17095 A1 8/1994
WO WO2006/106052 A1 10/2006

OTHER PUBLICATIONS

Lee, S.H. et al., "Fatty Acid Synthesis by Elongases in Trypanosomes", Cell, 2006, pp. 691-699, vol. 126.
Matsuzaka, T. et al., "Cloning and characterization of a mammalian fatty acyl-CoA elongase as a lipogenic enzyme regulated by SREBPs", Journal of Lipid Research, 2002, pp. 911-920, vol. 43.
Moon, Y. et al., "Identification of a Mammalian Long Chain Fatty Acyl Elongase Regulated by Sterol Regulatory Element-binding Proteins", The Journal of Biological Chemistry, 2001, pp. 45358-45366, vol. 276, No. 48.
Saito, et al., Bulletin of the Japanese Society for Neurochemistry, 1986, pp. 388-390, vol. 25, Issue 1.
STEP Taisha—Naibunpitsu (STEP Metabolism and Endocrine Secretion, Kaiba Shobo, 1st ed., 1998, p. 105.
The Merck Manual of Medical Information, second home ed., Merck & Co., 2003, Chapter 165, Diabetes Mellitus, p. 963.
RN577765-24-3, Sep. 2, 2003.
RN577983-35-8, Sep. 3, 2003.
RN578718-57-7, Sep. 4, 2003.
RN578761-79-2, Sep. 4, 2003.
RN587010-76-2, Sep. 17, 2003.
RN633287-91-9, Jan. 2, 2004.
RN633287-93-1, Jan. 2, 2004.
RN712346-01-5, Jul. 19, 2004.
RN712346-06-0, Jul. 19, 2004.
RN712346-07-1, Jul. 19, 2004.
RN845806-47-5, Mar. 17, 2005.
RN885434-72-0, May 24, 2006.
RN885434-79-7, May 24, 2006.
RN885434-86-6, May 24, 2006.
RN885434-93-5, May 24, 2006.
RN885435-00-7, May 24, 2006.

*Primary Examiner* — Kamal Saeed
(74) *Attorney, Agent, or Firm* — Janet E. Fair; John C. Todaro

(57) ABSTRACT

A compound represented by the general formula (I-a):

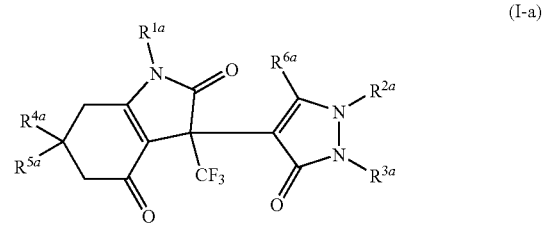

[wherein R1a and R2a each means hydrogen, lower cycloalkyl, lower alkyl, etc.; R3a means hydrogen, lower cycloalkyl, lower alkyl, etc.; R4a and R5a each means lower alkyl, lower cycloalkyl, etc. or R4a and R5a are bonded to each other to form lower cycloalkylidene; and R6a means lower alkyl, lower haloalkyl, etc.]. This compound functions as an LCE inhibitor and is useful as a therapeutic agent for various circulatory diseases, nervous diseases, metabolic diseases, reproductive diseases, digestive tract diseases, neoplasm, infectious diseases, etc.

20 Claims, No Drawings

INDOLEDIONE DERIVATIVE

CROSS-REFERENCE TO RELATED APPLICATIONS

This application is a U.S. National Phase application under 35 U.S.C. §371 of PCT Application No. PCT/JP2008/055825, filed Mar. 27, 2008, which claims priority under 35 U.S.C. §365(b) from Japanese patent application No. JP2007-096690, filed Apr. 2, 2007.

TECHNICAL FIELD

The present invention is useful in the pharmaceutical field. More specifically, the indoledione derivatives of the invention are useful as long chain fatty acyl elongase (hereinafter sometimes abbreviated as LCE) inhibitors in treating various circulatory diseases, neurological diseases, metabolic diseases, reproductive diseases, digestive tract diseases, neoplasm, infectious diseases and so on.

BACKGROUND ART

Obesity means a condition wherein energy intake continuously exceeds energy consumption and thus neutral lipids accumulate in adipocytes, which results in a remarkable increase in body weight compared with normal body weight (Eiji ITAGAKI, *STEP Taisha-Naibunpitsu* (*STEP Metabolism and Endocrine Secretion*), Kaiba Shobo, 1st ed., 1998, p. 105: Non-patent Document 1). It is known that the excessively accumulated lipids induce, for example, insulin resistance, diabetes, hypertension, hyperlipidemia and so on and a combination of a plural number of these factors highly increases the risk of the onset of atherosclerosis. These symptoms are called metabolic syndrome. Furthermore, it is known that hypertriglyceridemia or obesity increases the risk of the onset of, for example, pancreatitis, impaired liver function, cancer such as mammary cancer, uterine cancer, ovary cancer, colon cancer or prostatic cancer, menstrual disorder, arthritis, gout, cholecystitis, gastro-esophageal reflux, obesity-hypoventilation syndrome (Pickwickian syndrome), sleep apnea and so on. It is widely known that diabetes often leads to, onset of, for example, angina pectoris, heart failure, stroke, claudication, retinopathy, failing vision, renal failure, neuropathy, skin ulcer, infection and so on [*The Merck Manual of Medical Information*, second home ed., Merck & Co., 2003: Non-patent Document 2].

LCE occurring in endoplasmic reticula in cells is an enzyme which belongs to the group of enzymes catalyzing carbon chain elongation reactions of fatty acids having carbon chains consisting of 12 or more carbon atoms and catalyzes the rate-controlling condensation step. In mammals, many fatty acids newly synthesized in vivo have carbon chains consisting of 16 to 18 carbon atoms. These long chain fatty acids amount to more than 90% of the total fatty acids occurring in cells. These fatty acids are important constituents of membranes. Also, they are important components of fat tissues which are the largest energy storage organs in animals. New fatty acid synthesis occurs in the liver at the highest frequency. By this synthesis, excessive glucose in vivo is converted into fatty acids. Due to glycolysis, glucose is converted into pyruvate which is then converted into citrate in mitochondria and transported into the cytosol. ATP citrate lyase in the cytosol forms acetyl-CoA which is a precursor of a fatty acid and cholesterol. Acetyl-CoA is carboxylated by acetyl-CoA carboxylase (ACC) to give malonyl-CoA. Multifunctional fatty acid synthase (FAS) elongates a fatty acid by two carbon atoms using malonyl-CoA, acetyl-CoA and NADPH. The major final product of FAS in rodents is palmitoyl-CoA having a C16 carbon chain. This carbon chain of palmitoyl-CoA is further elongated by two carbon atoms by LCE [*J. Biol. Chem.*, 276(48), 45358 to 45366, (2001): Non-patent Document 3]. It is known that excessive promotion of fatty acid synthesis in vivo induces an increase in neutral lipids and the like and, in its turn, results in lipid accumulation. For example, WO 2005/005665 (Patent Document 1) indicates a direct relationship between LCE and obesity. It is also reported that the expression amount of mouse FACE (LCE) varies depending on food intake [Matsuzaka T. et al., *J. Lipid Res.*, 43(6):911 to 920 (2002): Non-patent Document 4].

It is known that LCE also occurs in protozoa and nematode and participates in the cell growth. In protozoa of the genus *Trypanosoma* causative of African trypanosomiasis (commonly called African sleeping sickness), for example, a long chain fatty acid is synthesized by a fatty acid-elongation pathway containing LCE. It is reported that the inhibition of the intracellular fatty acid elongation reaction affects the growth of the protozoa of the genus *Trypanosoma* [Lee S. H. et al., *Cell*, 126:691 to 699 (2006): Non-patent Document 5].

Therefore, it is expected that an LCE inhibitor is useful as a preventive and/or remedy for these diseases.

Although a part of the compounds according to the invention have been known in structure per se and these compounds have been commercially available, it has been neither disclosed nor suggested hitherto that these compounds have an LCE inhibitory effect.

Patent Document 1: WO 2005/005665

Non-patent Document 1: *STEP Taisha-Naibunpitsu* (*STEP Metabolism and Endocrine Secretion*, Kaiba Shobo, 1st ed., 1998, p. 105

Non-patent Document 2: *The Merck Manual of Medical Information*, second home ed., Merck & Co., 2003

Non-patent Document 3: *J. Biol. Chem.*, 276(48), 45358 to 45366, (2001)

Non-patent Document 4: *J. Lipid Res.*, 43(6):911 to 920 (2002)

Non-patent Document 5: *Cell*, 126:691 to 699 (2006)

DISCLOSURE OF THE INVENTION

Problems that the Invention is to Solve

An object of the invention is to provide a novel drug having an LCE inhibitory effect.

Means for Solving the Problems

As the results of intensive studies, the present inventors have found out that a compound represented by the general formula (I) has an excellent LCE inhibitory effect, thereby completing the invention:

[Chemical Formula 1]

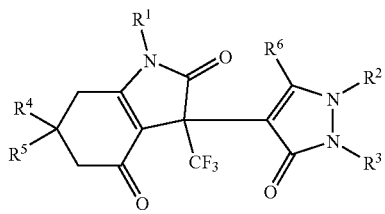

(I)

In the above formula, $R^1$ and $R^2$ each independently represents a hydrogen atom, a lower cycloalkyl group, an aryl group, a heteroaryl group or a lower alkyl group optionally substituted by a substituent selected from the group consisting of a lower cycloalkyl group, an aryl group and a heteroaryl group;

$R^4$ and $R^5$ each independently represents a lower alkyl group, a lower cycloalkyl group, an aryl group or an aralkyl group, or $R^4$ and $R^5$ may form a lower cycloalkylidene group together with the adjacent carbon atom;

$R^6$ represents a lower alkyl group, a lower haloalkyl group, a lower cycloalkyl group or a lower alkoxy-lower alkyl group; wherein the above-described lower cycloalkyl group, lower cycloalkylidene group, aryl group, aralkyl group and heteroaryl group may be each independently substituted by a substituent selected from the group consisting of a halogen atom, a lower alkyl group, a lower haloalkyl group and a lower alkoxy group;

$R^3$ represents a hydrogen atom, a lower cycloalkyl group, an aryl group, a heteroaryl group or a lower alkyl group optionally substituted by a substituent selected from the group consisting of a lower cycloalkyl group, an aryl group and a heteroaryl group, wherein the lower cycloalkyl group, aryl group and heteroaryl group in $R^3$ each independently represents an unsubstituted group or a lower cycloalkyl group, an aryl group or a heteroaryl group substituted by one or two substituents selected from the group consisting of a halogen atom, a nitro group, a cyano group, a lower alkyl group, a lower haloalkyl group, a lower alkoxy group, a lower haloalkoxy group, a carboxyl group, a lower cycloalkyl group, an aryl group, a heteroaryl group, an aryloxy group, an aralkyl group, —$CON(R^7)R^8$, —$N(R^7)R^8$, —$N(R^7)COR^8$, —$N(R^7)SO_2R^8$, —$OCOR^7$, —$OCON(R^7)R^8$, —$SR^7$, —$SO_2R^7$, —$SO_2N(R^7)R^8$ and

[Chemical Formula 2]

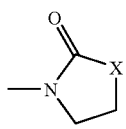

wherein $R^7$ and $R^8$ each independently represents a hydrogen atom or a lower alkyl group; and X represents —$N(R^7)$— or —O—.

The compounds (I) according to the invention have LCE inhibitory effect and, therefore, are useful as drugs for treating various diseases in which LCE participates, for example, circulatory diseases such as hypertension, angina pectoris, heart failure, cardiac infarction, stroke, claudication, diabetic renal failure, diabetic retinopathy, failing vision, electrolyte abnormality and atherosclerosis; central neurological diseases such as bulimia and diabetic neuropathy; metabolic diseases such as metabolic syndrome, obesity, diabetes, insulin resistance, hyperlipidemia, hypercholesterolemia, hypertriglyceridemia, dyslipidemia, non-alcoholic fatty liver, disturbance in hormone secretion, gout and fatty liver; reproductive diseases such as menstrual disorder and sexual dysfunction; digestive tract diseases such as impaired liver function, pancreatitis, cholecystitis and gastro-esophageal reflux; respiratory diseases such as obesity-hypoventilation syndrome (Pickwickian syndrome) and sleep apnea; infections caused by bacteria, fungi and parasites; malignant neoplasm; inflammatory diseases such as arthritis and skin ulcer; or a herbicide.

In particular, the compounds (I) according to the invention are useful as drugs for treating, for example, diabetes, obesity, non-alcoholic fatty liver or the like.

The invention relates to compounds represented by the general formula (I), salts or esters thereof and use of the same.

Next, the meanings of the terms used herein will be mentioned and the invention will be described in greater detail.

"Lower cycloalkyl group" means a cycloalkyl group having 3 to 6 carbon atoms and examples thereof include a cyclopropyl group, a cyclobutyl group, a cyclopentyl group and a cyclohexyl group.

"Lower cycloalkylidene group" means a cycloalkylidene group having 3 to 6 carbon atoms and examples thereof include a 1,1-cyclopropylidene group, a 1,1-cyclobutylidene group, a 1,1-cyclopentylidene group and a 1,1-cyclohexylidene group.

"Aryl group" means, for example, a phenyl group, a naphthyl group and so on.

"Aryloxy group" means, for example, a phenyloxy group, a 1-naphthyloxy group, a 2-naphthyloxy group and so on.

"Heteroaryl group" means a 5- or 6-membered monocyclic heteroaryl group having one or more (preferably 1 to 3) hetero atoms which are the same or different and selected from the group consisting of an oxygen atom, a nitrogen atom and a sulfur atom; or a fused ring heteroaryl group consisting of the preceding monocyclic heteroaryl group and the above-described aryl group condensed thereto, or the same or different preceding monocyclic heteroaryl groups condensed together; and examples thereof include a pyrrolyl group, a furyl group, a thienyl group, an imidazolyl group, a pyrazolyl group, a thiazolyl group, an isothiazolyl group, an oxazoyl group, an isoxazolyl group, a triazolyl group, a tetrazolyl group, an oxadiazolyl group, a 1,2,3-thiadiazolyl group, a 1,2,4-thiadiazolyl group, a 1,3,4-thiadiazolyl group, a pyridyl group, a pyrazinyl group, a pyrimidinyl group, a pyridazinyl group, a 1,2,4-triazinyl group, a 1,3,5-triazinyl group, an indolyl group, a benzofuranyl group, a benzothienyl group, a benzoimidazolyl group, a benzopyrazolyl group, a benzoxazolyl group, a benzoisoxazolyl group, a benzothiazolyl group, a benzoisothiazolyl group, an indazolyl group, a purinyl group, a quinolyl group, an isoquinolyl group, a phthalazinyl group, a naphthylidinyl group, a quinoxalynyl group, a quinazolinyl group, a cinnolinyl group, a puteridinyl group, a pyrido[3,2-b]pyridyl group and so on.

"Lower alkyl group" means a linear or branched alkyl group having 1 to 6 carbon atoms and examples thereof include a methyl group, an ethyl group, a propyl group, an isopropyl group, a butyl group, an isobutyl group, a sec-butyl group, a tert-butyl group, a pentyl group, an isopentyl group, a hexyl group, an isohexyl group and so on.

"Aralkyl group" means the above-described lower alkyl group that is substituted at an arbitrary substitutable position by one or more (preferably one) aryl group as described above and examples thereof include a benzyl group, a 1-phenylethyl group, a phenethyl group, a 1-naphthylmethyl group, a 2-naphthylmethyl group and so on.

"Halogen atom" includes a fluorine atom, a chlorine atom, a bromine atom and an iodine atom.

"Lower haloalkyl group" means the above-described lower alkyl group that is substituted at an arbitrary substitutable position by one or more (preferably 1 to 3) halogen atoms as described above that are the same or different. Examples thereof include a fluoromethyl group, a difluoromethyl group, a trifluoromethyl group, a 2-fluoroethyl group, a 1,2-difluoroethyl group, a chloromethyl group, a 2-chloroethyl group, a 1,2-dichloroethyl group, a bromomethyl group, an iodomethyl group and so on.

"Lower alkoxy group" means a linear or branched alkoxy group having 1 to 6 carbon atoms and examples thereof include a methoxy group, an ethoxy group, a propoxy group, an isopropoxy group, a butoxy group, a sec-butoxy group, an isobutoxy group, a tert-butoxy group, a pentyloxy group, an isopentyloxy group, a hexyloxy group, an isohexyloxy group and so on.

"Lower haloalkoxy group" means the lower alkoxy group as described above that is substituted at an arbitrary substitutable position by one or more (preferably 1 to 3) halogen atoms as described above that are the same or different. Examples thereof include a fluoromethoxy group, a difluoromethoxy group, a trifluoromethoxy group, a 2-fluoroethoxy group, a 1,2-difluoroethoxy group, a chloromethoxy group, a 2-chloroethoxy group, a 1,2-dichloroethoxy group, a bromomethoxy group, an iodomethoxy group and so on.

"Lower alkoxy-lower alkyl group" means the above-described lower alkyl group that is substituted at an arbitrary substitutable position by one or more (preferably 1 or 2) lower alkoxy groups as described above. Examples thereof include a methoxymethyl group, an ethoxymethyl group, a 2-methoxyethyl group, a 1-methoxy-1-methylethyl group, a 1,2-methoxyethyl group, a 3-methoxypropyl group and so on.

"Salt" of the compound according to the invention means pharmaceutically acceptable and common salts and examples thereof include base addition salts at a carboxyl group in the case of a compound having the carboxyl group or acid addition salts at an amino group or at a basic heterocyclic group in the case of a compound having the basic heterocyclic group.

Examples of the base addition salt include alkali metal salts such as sodium salts, and potassium salts; alkaline earth metal salts such as calcium salts and magnesium salts; ammonium salts; and organic amine salts such as trimethylamine salts, triethylamine salts, dicyclohexylamine salts, ethanolamine salts, diethanolamine salts, triethanolamine salts, procaine salts, N,N'-dibenzylethylenediamine salts, and so on.

Examples of the acid addition salt include inorganic acid salts such as hydrochlorides, sulfates, nitrates, phosphates, perchlorates and so on; organic acid salts such as maleates, fumarates, tartrates, citrates, ascorbates, trifluoroacetates and so on; and sulfonates such as methanesulfonates, isethionates, benzenesulfonates, p-toluenesulfonates and so on.

"Ester" of the compound according to the invention means pharmaceutically acceptable and common salts at a carboxyl group in the case of, for example, a compound having the carboxyl group. Examples thereof include esters with a lower alkyl group such as a methyl group, an ethyl group, a propyl group, an isopropyl group, a butyl group, a sec-butyl group, a tert-butyl group, a pentyl group, an isopentyl group, a neopentyl group, a cyclopropyl group, a cyclobutyl group or cyclopentyl group; esters with an aralkyl group such as a benzyl group or a phenethyl group; esters with a lower alkenyl group such as an allyl group, or a 2-butenyl group; esters with a lower alkoxy-lower alkyl group such as a methoxymethyl group, a 2-methoxyethyl group or a 2-ethoxyethyl group; esters with a lower alkanoyloxy lower alkyl group such as an acetoxymethyl group, a pivaloyloxymethyl group or a 1-pivaloyloxyethyl group; esters with a lower alkoxycarbonyl lower alkyl group such as a methoxycarbonylmethyl group, or an isopropoxycarbonylmethyl group; esters with a carboxy lower alkyl group such as a carboxymethyl group; esters with a lower alkoxycarbonyloxy lower alkyl group such as a 1-(ethoxycarbonyloxy)ethyl group or a 1-(cyclohexyloxycarbonyloxy)ethyl group; esters with a carbamoyloxy lower alkyl group such as a carbamoyloxymethyl group; and esters with a phthalidyl group; and esters with a (5-substituted-2-oxo-1,3-dioxol-4-yl)methyl group such as a (5-methyl-2-oxo-1,3-dioxol-4-yl)methyl group.

"Treating agent" means a drug which is used for the treatment and/or prevention of various diseases.

To further disclose the compounds according to the invention, the individual symbols used in the formula (I) and so on will be described in particular by citing preferred examples thereof $R^1$ and $R^2$ each independently represents a hydrogen atom, a lower cycloalkyl group, an aryl group, a heteroaryl group or a lower alkyl group optionally substituted by a substituent selected from the group consisting of a lower cycloalkyl group, an aryl group and a heteroaryl group. The above-described lower cycloalkyl group, aryl group and heteroaryl group may be each independently substituted by a substituent selected from the group consisting of a halogen atom, a lower alkyl group, a lower haloalkyl group and a lower alkoxy group.

Preferred examples of a lower cycloalkyl group as $R^1$ or $R^2$ include a cyclopropyl group, a cyclobutyl group, a cyclopenthyl group, a cyclohexyl group and so on.

Preferred examples of an aryl group as $R^1$ or $R^2$ include a phenyl group and so on.

Preferred examples of a heteroaryl group as $R^1$ or $R^2$ include a pyridyl group and so on.

"Lower alkyl group optionally substituted by a substituent selected from the group consisting of a lower cycloalkyl group, an aryl group and a heteroaryl group" as $R^1$ or $R^2$ means an unsubstituted lower alkyl group as described above or the above-described lower alkyl group that is substituted at an arbitrary substitutable position by one or more (preferably one) substituents which are the same or different and selected from the group consisting of a lower cycloalkyl group, an aryl group and a heteroaryl group.

Preferred examples of the lower cycloalkyl group as the substituent include a cyclopentyl group, a cyclohexyl group and so on.

Preferred examples of the aryl group as the substituent include a phenyl group and so on.

Preferred examples of the heteroaryl group as the substituent include a furyl group, a pyridyl group and so on.

Preferred examples of the substituent include a phenyl group, a pyridyl group and so on.

As "Lower alkyl group" per se in the lower alkyl group optionally having the above-described substituent as $R^1$ or $R^2$ include a methyl group, an ethyl group, a propyl group, an isopropyl group, a butyl group and so on.

The above-described lower cycloalkyl group, aryl group and heteroaryl group may be each independently substituted at an arbitrary substitutable position by one or more (preferably 1 or 2) substituents that are the same or different and selected from the group consisting of a halogen atom, a lower alkyl group, a lower haloalkyl group and a lower alkoxy group.

Preferred examples of the halogen atom as the substituent include a fluorine atom, a chlorine atom and so on.

Preferred examples of the lower alkyl group as the substituent include a methyl group, an ethyl group and so on.

Preferred examples of the lower haloalkyl group as the substituent include a difluoromethyl group, a trifluoromethyl group and so on.

Preferred examples of the lower alkoxy group as the substituent include a methoxy group, an ethoxy group and so on.

Preferred examples of the substituent include a halogen atom, a lower alkoxy group and so on.

Thus, examples of $R^1$ include a hydrogen atom, a cyclopropyl group, a cyclobutyl group, a cyclopentyl group, a cyclohexyl group, a phenyl group, a 2-pyridyl group, a 3-pyridyl group, a 4-pyridyl group, a methyl group, an ethyl group, a propyl group, an isopropyl group, a butyl group, a benzyl group, a phenethyl group, a furfuryl group, a 2-pyridylmethyl group, a 3-pyridylmethyl group, a 4-pyridylmethyl group, a 2-fluorophenyl group, a 2-chlorophenyl group, a 3-fluorophenyl group, a 3-chlorophenyl group, a 4-fluorophenyl group, a 4-chlorophenyl group, a 3,4-dichlorophenyl, a 4-methylphenyl group, a 3,4-dimethylphenyl group, a 3-trifluoromethylphenyl group, a 2-methoxyphenyl group, a 3-methoxyphenyl group, a 4-methoxyphenyl group, a 2-fluorobenzyl group, a 2-chlorobenzyl group, a 4-fluorobenzyl group, a 4-chlorobenzyl group, a 3,4-dimethoxyphenethyl group and so on. Among them, preferable examples include a cyclopropyl group, a cyclobutyl group, a cyclopentyl group, a cyclohexyl group, a propyl group, a 2-pyridylmethyl group, a 3-pyridylmethyl group, a 4-pyridylmethyl group, a 4-chlorophenyl group and 3-methoxyphenyl group, or a phenyl group, a benzyl group, a 3-chlorophenyl group, a 4-fluorophenyl group, a 4-methoxyphenyl group and so on. In particular, a cyclohexyl group, a phenyl group and so on are preferred.

Preferred examples of $R^2$ include a hydrogen atom, a methyl group and so on and a hydrogen atom is particularly preferred.

$R^4$ and $R^5$ each independently represents a lower alkyl group, a lower cycloalkyl group, an aryl group or an aralkyl group, or $R^4$ and $R^5$ may form a lower cycloalkylidene group together with the adjacent carbon atom. The above-described lower cycloalkyl group, lower cycloalkylidene group, aryl group or aralkyl group may be each individually substituted at an arbitrary substitutable position by a substituent selected from the group consisting of a halogen atom, a lower alkyl group, a lower haloalkyl group and a lower alkoxy group.

Preferred examples of a lower alkyl group as $R^4$ or $R^5$ include a methyl group, an ethyl group, a propyl group and so on and a methyl group is particularly preferred.

Preferred examples of a lower cycloalkyl group as $R^4$ or $R^5$ include a cyclobutyl group, a cyclopenthyl group, a cyclohexyl group and so on.

Preferred examples of an aryl group as $R^4$ or $R^5$ include a phenyl group and so on.

Preferred examples of an aralkyl group as $R^4$ or $R^5$ include a benzyl group and so on.

Preferred examples of the lower cycloalkylidene group per se in the case where $R^4$ and $R^5$ "form a lower cycloalkylidene group together with the adjacent carbon atom" include a 1,1-cyclobutylidene group and so on.

The above-described lower cycloalkyl group, lower cycloalkylidene group, aryl group or aralkyl group may be each independently substituted by one or more (preferably 1 or 2) substituents that are the same or different and selected from the group consisting of a halogen atom, a lower alkyl group, a lower haloalkyl group and a lower alkoxy group.

Preferred examples of the halogen atom as the substituent include a fluorine atom, a chlorine atom and so on.

Preferred examples of the lower alkyl group as the substituent include a methyl group, an ethyl group and so on.

Preferred examples of the lower haloalkyl group as the substituent include a difluoromethyl group, a trifluoromethyl group and so on.

Preferred examples of the lower alkoxy group as the substituent include a methoxy group, an ethoxy group and so on.

Preferred examples of the substituent include a halogen atom, a lower alkoxy group and so on.

Preferred embodiment of $R^4$ and $R^5$ include a case where $R^4$ and $R^5$ are both lower alkyl groups (more preferably both methyl groups), and a case where $R^4$ and $R^5$ form together with the adjacent carbon atom a lower cycloalkylidene group (more preferably a 1,1-cyclobutylidene group or the like).

$R^6$ represents a lower alkyl group, a lower haloalkyl group, a lower cycloalkyl group or a lower alkoxy-lower alkyl group.

Preferred examples of the lower alkyl group as $R^6$ include a methyl group, an ethyl group, an n-propyl group, an isopropyl group and so on and a methyl group is particularly preferred.

Preferred examples of the lower haloalkyl group as $R^6$ include a trifluoromethyl group and so on.

Preferred examples of the lower cycloalkyl group as $R^6$ include a cyclopropyl group and so on.

Preferred examples of the lower alkoxy-lower alkyl group as $R^6$ include a methoxymethyl group and so on.

A lower alkyl group is preferred as $R^6$.

$R^3$ represents a hydrogen atom, a lower cycloalkyl group, an aryl group, a heteroaryl group or a lower alkyl group optionally substituted by a substituent selected from the group consisting of a lower cycloalkyl group, an aryl group and a heteroaryl group, wherein the lower cycloalkyl group, aryl group and heteroaryl group in $R^3$ each independently represents an unsubstituted group or a lower cycloalkyl group, an aryl group or a heteroaryl group substituted by one or two substituents selected from the group consisting of a halogen atom, a nitro group, a cyano group, a lower alkyl group, a lower haloalkyl group, a lower alkoxy group, a lower haloalkoxy group, a carboxyl group, a lower cycloalkyl group, an aryl group, a heteroaryl group, an aryloxy group, an aralkyl group, —CON($R^7$)$R^8$, —N($R^7$)$R^8$, —N($R^7$)COR$^8$, —N($R^7$)SO$_2$R$^8$, —OCOR$^7$, —OCON($R^7$)$R^8$, —SR$^7$, —SO$_2$R$^7$, —SO$_2$N($R^7$)$R^8$ and

[Chemical Formula 3]

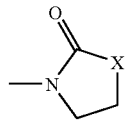

In the above formula, $R^7$ and $R^8$ each independently represents a hydrogen atom or a lower alkyl group; and X represents —N($R^7$)— or —O—.

Preferred examples of the lower cycloalkyl group as $R^3$ include a cyclopropyl group, a cyclobutyl group, a cyclopentyl group, a cyclohexyl group and so on.

Preferred examples of the aryl group as $R^3$ include a phenyl group and so on.

Preferred examples of the heteroaryl group as $R^3$ include a pyridyl group, a 5-benzopyrazolyl group, a 6-benzopyrazolyl group and so on.

"Lower alkyl group optionally substituted by a substituent selected from the group consisting of a lower cycloalkyl group, an aryl group and a heteroaryl group" as $R^3$ means an unsubstituted lower alkyl group as described above or the above-described lower alkyl group that is substituted at an arbitrary substitutable position by one or more (preferably one) substituents which are the same or different and selected from the group consisting of a lower cycloalkyl group, an aryl group and a heteroaryl group.

Preferred examples of the lower cycloalkyl group as the substituent include a cyclopentyl group, a cyclohexyl group and so on.

Preferred examples of the aryl group as the substituent include a phenyl group and so on.

Preferred examples of the heteroaryl group as the substituent include a furyl group, a pyridyl group and so on.

Preferred examples of the substituent include a phenyl group, a pyridyl group and so on.

As preferred examples of "Lower alkyl group" per se in the lower alkyl group optionally having the above-described substituent as $R^3$ include a methyl group, an ethyl group, a propyl group, an isopropyl group, a butyl group and so on.

The lower cycloalkyl group, aryl group and heteroaryl group in $R^3$ each independently represents an unsubstituted group or a lower cycloalkyl group, an aryl group or a heteroaryl group substituted by one or two substituents selected from the group consisting of a halogen atom, a nitro group, a cyano group, a lower alkyl group, a lower haloalkyl group, a lower alkoxy group, a lower haloalkoxy group, a carboxyl group, a lower cycloalkyl group, an aryl group, a heteroaryl group, an aryloxy group, an aralkyl group, —CON($R^7$)$R^8$, —N($R^7$)$R^8$, —N($R^7$)COR$^8$, —N($R^7$)SO$_2$R$^8$, —OCOR$^7$, —OCON($R^7$)$R^8$, —SR$^7$, —SO$_2$R$^7$, —SO$_2$N($R^7$)$R^8$ and

[Chemical Formula 4]

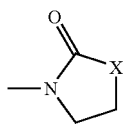

In the above formula, $R^7$ and $R^8$ each independently represents a hydrogen atom or a lower alkyl group; and X represents —N($R^7$)— or —O—.

Preferred examples of the halogen atom as the substituent include a fluorine atom, a chlorine atom and so on.

Preferred examples of the lower alkyl group as the substituent include a methyl group, an ethyl group and so on.

Preferred examples of the lower haloalkyl group as the substituent include a difluoromethyl group, a trifluoromethyl group and so on.

Preferred examples of the lower alkoxy group as the substituent include a methoxy group, an ethoxy group and so on.

Preferred examples of the lower haloalkoxy group as the substituent include a trifluoromethoxy group and so on.

Preferred examples of the lower cycloalkyl group as the substituent include a cyclopentyl group, a cyclohexyl group and so on.

Preferred examples of the aryl group as the substituent include a phenyl group and so on.

Preferred examples of the heteroaryl group as the substituent include a pyridyl group and so on.

Preferred examples of the aryloxy group as the substituent include a phenoxy group and so on.

Preferred examples of the aralkyl group as the substituent include a benzyl group and so on.

In the groups represented by —CON($R^7$)$R^8$, —N($R^7$)$R^8$, —N($R^7$)COR$^8$, —N($R^7$)SO$_2$R$^8$, —OCOR$^7$, —OCON($R^7$)$R^8$, —SR$^7$, —SO$_2$R$^7$, —SO$_2$N($R^7$)$R^8$ and

[Chemical Formula 5]

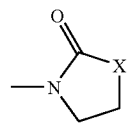

$R^7$ and $R^8$ each independently represents a hydrogen atom or a lower alkyl group; and X represents —N($R^7$)— or —O—.

Preferred examples of the lower alkyl group as $R^7$ or $R^8$ include a methyl group, an ethyl group and so on.

Preferred examples of the substituent include a halogen atom, a cyano group, a lower alkyl group, a lower haloalkyl group, a lower alkoxy group, —SO$_2$N($R^7$)$R^8$ and so on.

Preferable examples of $R^3$ include an isopropyl group, a cyclohexyl group, an unsubstituted phenyl group and a phenyl group substituted by one or two substituents selected from the group consisting of a halogen atom, a nitro group, a cyano group, a lower alkyl group, a lower haloalkyl group, a lower alkoxy group, a lower haloalkoxy group, a carboxyl group, a lower cycloalkyl group, an aryl group, a heteroaryl group, an aryloxy group, an aralkyl group, —CON($R^7$)$R^8$, —N($R^7$)$R^8$, —N($R^7$)COR$^8$, —N($R^7$)SO$_2$R$^8$, —OCOR$^7$, —OCON($R^7$)$R^8$, —SR$^7$, —SO$_2$R$^7$, —SO$_2$N($R^7$)$R^8$ and

[Chemical Formula 6]

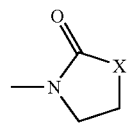

Particularly preferred examples thereof include a phenyl group substituted by one or two substituents selected independently from the group consisting of a halogen atom, a cyano group, a lower alkyl group, a lower haloalkyl group, a lower alkoxy group, a lower haloalkoxy group, —SO$_2$N($R^7$)$R^8$ and so on.

Thus, specific examples preferred as $R^3$ include an isopropyl group, a cyclohexyl group, a phenyl group, a 5-benzopyrazolyl group, a 6-benzopyrazolyl group, a 3-fluorophenyl group, a 4-fluorophenyl group, a 3,4-difluorophenyl group, a 3,5-difluorophenyl group, a 3-chlorophenyl group, a 4-chlorophenyl group, a 3,4-dichlorophenyl group, a 3,5-dichlorophenyl group, a 4-nitrophenyl group, a 3-cyanophenyl group, a 4-cyanophenyl group, a 3-methylphenyl group, a 4-methylphenyl group, a 3,5-dimethylphenyl group, a 3-isopropylphenyl group, a 4-isopropylphenyl group, a 4-tert-butylphenyl group, a 3-trifluoromethylphenyl group, a 4-trifluoromethylphenyl group, a 2-methoxyphenyl group, a 3-methoxyphenyl group, a 4-methoxyphenyl group, a 4-isopropoxyphenyl group, a 4-trifluoromethoxyphenyl group, a 4-carboxyphenyl group, a 4-cyclohexylphenyl group, a 4-biphenylyl group, a 4-benzylphenyl group, a 4-phenoxyphenyl group, a 4-carbamoylphenyl group, a 4-methylcarbamoylphenyl group, a 4-dimethylcarbamoylphenyl group, a 4-aminophenyl group, a 4-methylaminophenyl group, a 4-dimethylaminophenyl group, a 4-acetylaminophenyl group, a 4-(N-methylacetylamino)phenyl group, a 4-methylsulfonylaminophenyl group, a 4-(N-methylmethylsulfonylamino)phenyl group, a 4-tert-butoxycarbonyloxyphenyl group, a 4-dimethylcarbamoyloxyphenyl group, a 4-methylthiophenyl group, a 4-methylsulfonylphenyl group, a 3-aminosulfonylphenyl group, a 4-aminosulfonylphenyl group, a 4-methylsulfonylphenyl group and groups represented by the following formulae

[Chemical Formula 7]

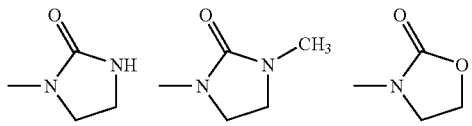

Among all, preferred examples include a phenyl group, a 4-fluorophenyl group, a 3-chlorophenyl group, a 4-chlorophenyl group, a 4-cyanophenyl group, a 4-methylphenyl group, a 4-isopropylphenyl group, a 4-tert-butylphenyl group, a 4-trifluoromethylphenyl group, a 2-methoxyphenyl group, a 3-methoxyphenyl group, a 4-methoxyphenyl group, a 4-trifluoromethoxyphenyl group, a 4-biphenylyl group, a 4-aminosulfonylphenyl group, a 4-methylsulfonylphenyl group and so on.

A preferred embodiment of $R^1$, $R^2$, $R^3$, $R^4$, $R^5$ and $R^6$ is a case where $R^2$ is a hydrogen atom, $R^3$ is a phenyl group and $R^4$, $R^5$ and $R^6$ are respectively methyl groups. In this case, it is preferred that $R^1$ is one of the preferred groups as cited above. Another preferred embodiment of $R^1$, $R^2$, $R^3$, $R^4$, $R^5$ and $R^6$ is a case where $R^1$ is one of the preferred group as cited above, $R^2$ is a hydrogen atom, $R^4$, $R^5$ and $R^6$ are respectively methyl groups, and $R^3$ is a phenyl group that is substituted by preferred group(s) as cited above.

Among the compounds represented by the general formula (I), compounds wherein $R^2$ is a hydrogen atom; $R^3$ is a phenyl group; $R^4$, $R^5$ and $R^6$ are respectively methyl groups; and $R^1$ is an n-butyl group, a phenyl group, a 4-fluorophenyl group, a 3-chlorophenyl group, a 3,4-dichlorophenyl group, a 4-methylphenyl group, a 3,4-dimethylphenyl group, a 3-trifluoromethylphenyl group, a 4-methoxyphenyl group, a furfuryl group, a benzyl group, a phenethyl group, a 4-fluorobenzyl group, a 2-chlorobenzyl group or a 3,4-dimethoxyphenethyl group have been known in public. These compounds are marketed by, for example, [ChemBridge, R1=phenyl group] and shown in its catalogue (Catalogue No. 7904749).

On the other hand, compounds represented by the general formula (I-a):

[Chemical Formula 8]

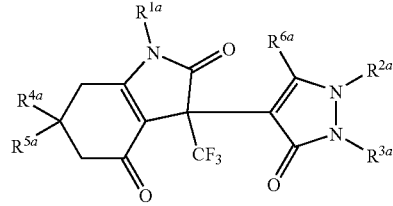

(I-a)

In the above formula,
$R^{1a}$ and $R^{2a}$ each independently represents a hydrogen atom, a lower cycloalkyl group, an aryl group, a heteroaryl group or a lower alkyl group optionally substituted by a substituent selected from the group consisting of a lower cycloalkyl group, an aryl group and a heteroaryl group;

$R^{4a}$ and $R^{5a}$ each independently represents a lower alkyl group, a lower cycloalkyl group, an aryl group or an aralkyl group, or $R^{4a}$ and $R^{5a}$ may form a lower cycloalkylidene group together with the adjacent carbon atom;

$R^{6a}$ represents a lower alkyl group, a lower haloalkyl group, a lower cycloalkyl group or a lower alkoxy-lower alkyl group; wherein the above-described lower cycloalkyl group, lower cycloalkylidene group, aryl group, aralkyl group and heteroaryl group may be each independently substituted by a substituent selected from the group consisting of a halogen atom, a lower alkyl group, a lower haloalkyl group and a lower alkoxy group;

$R^{3a}$ represents a hydrogen atom, a lower cycloalkyl group, an aryl group, a heteroaryl group or a lower alkyl group optionally substituted by a substituent selected from the group consisting of a lower cycloalkyl group, an aryl group and a heteroaryl group, wherein the lower cycloalkyl group, aryl group and heteroaryl group in $R^{3a}$ each independently represents an unsubstituted group or a lower cycloalkyl group, an aryl group or a heteroaryl group substituted by one or two substituents selected from the group consisting of a halogen atom, a nitro group, a cyano group, a lower alkyl group, a lower haloalkyl group, a lower alkoxy group, a lower haloalkoxy group, a carboxyl group, a lower cycloalkyl group, an aryl group, a heteroaryl group, an aryloxy group, an aralkyl group, $—CON(R^7)R^8$, $—N(R^7)R^8$, $—N(R^7)COR^8$, $—N(R^7)SO_2R^8$, $—OCOR^7$, $—OCON(R^7)R^8$, $—SR^7$, $—SO_2R^7$, $—SO_2N(R^7)R^8$ and

[Chemical Formula 9]

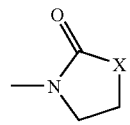

wherein $R^7$ and $R^8$ each independently represents a hydrogen atom or a lower alkyl group; and X represents $—N(R^7)—$ or $—O—$ (provided that when $R^{2a}$ is a hydrogen atom, $R^{3a}$ is a phenyl group and $R^{4a}$, $R^{5a}$ and $R^{6a}$ are respectively methyl groups, then $R^{1a}$ does not represent an n-butyl group, a phenyl group, a 4-fluorophenyl group, a 3-chlorophenyl group, a 3,4-dichlorophenyl group, a 4-methylphenyl group, a 3,4-dimethylphenyl group, a 3-trifluoromethylphenyl group, a 4-methoxyphenyl group, a furfuryl group, a benzyl group, a phenethyl group, a 4-fluorobenzyl group, a 2-chlorobenzyl group or a 3,4-dimethoxyphenethyl group);
are novel compounds that have never been reported in documents, etc. and have been created by the present inventors.

Preferred embodiments of $R^{1a}$, $R^{2a}$, $R^{3a}$, $R^{4a}$, $R^{5a}$ and $R^{6a}$ in the compound represented by the general formula (I-a) are the same as those of $R^1$, $R^2$, $R^3$, $R^4$, $R^5$ and $R^6$ in the compound represented by the general formula (I), excluding the cases corresponding to the publicly known compounds as mentioned above. Among all, it is particularly preferred that $R^{1a}$ is a cyclopropyl group, a cyclobutyl group, a cyclopentyl group, a cyclohexyl group, a propyl group, a 2-pyridylmethyl group, a 3-pyridylmethyl group, a 4-pyridylmethyl group, a 4-chlorophenyl group or a 3-methoxyphenyl group and a cyclopropyl group, a cyclobutyl group, a cyclopentyl group or a cyclohexyl group is still preferred as $R^{1a}$.

"An any arbitrary substitutable position" means a position of a chemically-substitutable hydrogen atom on the carbon atom, nitrogen atom, oxygen atom and/or sulfur atom thereof, and a chemically-stable compound is obtained as the result of the substitution.

Depending on the type of the substituents or on the form of salts, the compounds of the invention sometimes occur as stereoisomers or tautomers such as optical isomers, diastereoisomers and geometrical isomers, and the compounds of the invention encompass all these stereoisomers, tautomers and their mixtures.

Moreover, the invention encompasses various crystals, amorphous, salts, hydrates and solvates of the compounds according to the invention.

Further, prodrugs of the compounds according to the invention also fall within the scope of the invention. In general, such prodrugs are functional derivatives of the compounds of the invention which can be readily converted into the compounds required in vivo. Thus, the term "administer" as used herein concerning the method of treating various disorders includes not only the administration of a specific compound but also the administration of a compound which, after administered to patients, may be converted into the specific compound in vivo. Commonly employed methods for selection and production of suitable prodrug derivatives are described, for example, in *Design of Prodrugs*, ed. H. Bundgaard, Elsevier, 1985, etc. and the entire descriptions of which are referred to and incorporated herein as a part of the specification of the present application. Metabolites of these compounds include active compounds that are produced by allowing the compounds of the invention to stand in a biological environment, and they also fall within a scope of the invention.

Specific examples of the compounds of the general formula (I), and their salts or esters include the compounds mentioned in Production Examples and salts and esters thereof. Among all, preferred examples thereof are as follows:

3-(2,5-dihydro-3-methyl-5-oxo-1-phenyl-1H-pyrazol-4-yl)-3,5,6,7-tetrahydro-6,6-dimethyl-1-phenyl-3-trifluoromethyl-1H-indole-2,4-dione, 3-(2,5-dihydro-3-methyl-5-oxo-1-phenyl-1H-pyrazol-4-yl)-3,5,6,7-tetrahydro-6,6-dimethyl-1-phenylmethyl-3-trifluoromethyl-1H-indole-2,4-dione, 1-(4-fluorophenyl)-3-(2,5-dihydro-3-methyl-5-oxo-1-phenyl-1H-pyrazol-4-yl)-3,5,6,7-tetrahydro-6,6-dimethyl-3-trifluoromethyl-1H-indole-2,4-dione, 3-(2,5-dihydro-3-methyl-5-oxo-1-phenyl-1H-pyrazol-4-yl)-3,5,6,7-tetrahydro-1-(4-methoxyphenyl)-6,6-dimethyl-3-trifluoromethyl-1H-indole-2,4-dione, 1-(3-chlorophenyl)-3-(2,5-dihydro-3-methyl-5-oxo-1-phenyl-1H-pyrazol-4-yl)-3,5,6,7-tetrahydro-6,6-dimethyl-3-trifluoromethyl-1H-indole-2,4-dione, 1-(4-chlorophenyl)-3-(2,5-dihydro-3-methyl-5-oxo-1-phenyl-1H-pyrazol-4-yl)-3,5,6,7-tetrahydro-6,6-dimethyl-3-trifluoromethyl-1H-indole-2,4-dione, 3-(2,5-dihydro-3-methyl-5-oxo-1-phenyl-1H-pyrazol-4-yl)-3,5,6,7-tetrahydro-1-(3-methoxyphenyl)-6,6-dimethyl-3-trifluoromethyl-1H-indole-2,4-dione, 3-(2,5-dihydro-3-methyl-5-oxo-1-phenyl-1H-pyrazol-4-yl)-3,5,6,7-tetrahydro-1,6,6-trimethyl-3-trifluoromethyl-1H-indole-2,4-dione, 1-ethyl-3-(2,5-dihydro-3-methyl-5-oxo-1-phenyl-1H-pyrazol-4-yl)-3,5,6,7-tetrahydro-6,6-dimethyl-3-trifluoromethyl-1H-indole-2,4-dione, 3-(2,5-dihydro-3-methyl-5-oxo-1-phenyl-1H-pyrazol-4-yl)-3,5,6,7-tetrahydro-6,6-dimethyl-1-propyl-3-trifluoromethyl-1H-indole-2,4-dione, 3-(2,5-dihydro-3-methyl-5-oxo-1-phenyl-1H-pyrazol-4-yl)-3,5,6,7-tetrahydro-1-isopropyl-6,6-dimethyl-3-trifluoromethyl-1H-indole-2,4-dione, 1-cyclopropyl-3-(2,5-dihydro-3-methyl-5-oxo-1-phenyl-1H-pyrazol-4-yl)-3,5,6,7-tetrahydro-6,6-dimethyl-3-trifluoromethyl-1H-indole-2,4-dione, 1-cyclobutyl-3-(2,5-dihydro-3-methyl-5-oxo-1-phenyl-1H-pyrazol-4-yl)-3,5,6,7-tetrahydro-6,6-dimethyl-3-trifluoromethyl-1H-indole-2,4-dione, 1-cyclopentyl-3-(2,5-dihydro-3-methyl-5-oxo-1-phenyl-1H-pyrazol-4-yl)-3,5,6,7-tetrahydro-6,6-dimethyl-3-trifluoromethyl-1H-indole-2,4-dione, 1-cyclohexyl-3-(2,5-dihydro-3-methyl-5-oxo-1-phenyl-1H-pyrazol-4-yl)-3,5,6,7-tetrahydro-6,6-dimethyl-3-trifluoromethyl-1H-indole-2,4-dione, 3-(2,5-dihydro-3-methyl-5-oxo-1-phenyl-1H-pyrazol-4-yl)-3,5,6,7-tetrahydro-6,6-dimethyl-1-(2-pyridylmethyl)-3-trifluoromethyl-1H-indole-2,4-dione, 3-(2,5-dihydro-3-methyl-5-oxo-1-phenyl-1H-pyrazol-4-yl)-3,5,6,7-tetrahydro-6,6-dimethyl-1-(3-pyridylmethyl)-3-trifluoromethyl-1H-indole-2,4-dione, 3-(2,5-dihydro-3-methyl-5-oxo-1-phenyl-1H-pyrazol-4-yl)-3,5,6,7-tetrahydro-6,6-dimethyl-1-(4-pyridylmethyl)-3-trifluoromethyl-1H-indole-2,4-dione, 3-(3-ethyl-2,5-dihydro-5-oxo-1-phenyl-1H-pyrazol-4-yl)-3,5,6,7-tetrahydro-6,6-dimethyl-1-phenyl-3-trifluoromethyl-1H-indole-2,4-dione, 3-(3-cyclopropyl-2,5-dihydro-5-oxo-1-phenyl-1H-pyrazol-4-yl)-3,5,6,7-tetrahydro-6,6-dimethyl-1-phenyl-3-trifluoromethyl-1H-indole-2,4-dione, 3-(2,5-dihydro-5-oxo-1-phenyl-3-trifluoromethyl-1H-pyrazol-4-yl)-3,5,6,7-tetrahydro-6,6-dimethyl-1-phenyl-3-trifluoromethyl-1H-indole-2,4-dione, 3-[1-(3-chlorophenyl)-2,5-dihydro-3-methyl-5-oxo-1H-pyrazol-4-yl]-3,5,6,7-tetrahydro-6,6-dimethyl-1-phenyl-3-trifluoromethyl-1H-indole-2,4-dione, 3-[1-(4-chlorophenyl)-2,5-dihydro-3-methyl-5-oxo-1H-pyrazol-4-yl]-3,5,6,7-tetrahydro-6,6-dimethyl-1-phenyl-3-trifluoromethyl-1H-indole-2,4-dione, 3-[2,5-dihydro-1-(2-methoxyphenyl)-3-methyl-5-oxo-1H-pyrazol-4-yl]-3,5,6,7-tetrahydro-6,6-dimethyl-1-phenyl-3-trifluoromethyl-1H-indole-2,4-dione, 3-[2,5-dihydro-1-(3-methoxyphenyl)-3-methyl-5-oxo-1H-pyrazol-4-yl]-3,5,6,7-tetrahydro-6,6-dimethyl-1-phenyl-3-trifluoromethyl-1H-indole-2,4-dione, 3-[2,5-dihydro-1-(4-methoxyphenyl)-3-methyl-5-oxo-1H-pyrazol-4-yl]-1-phenyl-3,5,6,7-tetrahydro-6,6-dimethyl-3-trifluoromethyl-1H-indole-2,4-dione, 3-(2,5-dihydro-3-methyl-5-oxo-1-phenyl-1H-pyrazol-4-yl)-3,5,6,7-tetrahydro-6-methyl-1-phenyl-3-trifluoromethyl-1H-indole-2,4-dione, 3'-(2,5-dihydro-3-methyl-5-oxo-1-phenyl-1H-pyrazol-4-yl)-1'-phenyl-3'-trifluoromethyl-3',7'-dihydrospiro[cyclobutane-1,6'-indole]-2',4'(1'H,5'H)-dione, 3-[2,5-dihydro-3-methyl-5-oxo-1-(4-trifluoromethylphenyl)-1H-pyrazol-4-yl]-3,5,6,7-tetrahydro-6,6-dimethyl-1-phenyl-3-trifluoromethyl-1H-indole-2,4-dione, 3-[1-(4-fluorophenyl)-2,5-dihydro-3-methyl-5-oxo-1H-pyrazol-4-yl]-3,5,6,7-tetrahydro-6,6-dimethyl-1-phenyl-3-trifluoromethyl-1H-indole-2,4-dione, 3-[1-(4-cyanophenyl)-2,5-dihydro-3-methyl-5-oxo-1H-pyrazol-4-yl]-3,5,6,7-tetrahydro-6,6-dimethyl-1-phenyl-3-trifluoromethyl-1H-indole-2,4-dione, 3-[2,5-dihydro-1-(4-isopropylphenyl)-3-methyl-5-oxo-1H-pyrazol-4-yl]-3,5,6,7-tetrahydro-6,6-dimethyl-1-phenyl-3-trifluoromethyl-1H-indole-2,4-dione, 3-[2,5-dihydro-3-methyl-1-(4-methylphenyl)-5-oxo-1H-pyrazol-4-yl]-3,5,6,7-tetrahydro-6,6-dimethyl-1-phenyl-3-trifluoromethyl-1H-indole-2,4-dione, 3-[1-(4-aminosulfonylphenyl)-2,5-dihydro-3-trifluoromethyl-5-oxo-1H-pyrazol-4-yl]-3,5,6,7-tetrahydro-6,6-dimethyl-1-phenyl-3-trifluoromethyl-1H-indole-2,4-dione, 3-[1-(4-tert-butylphenyl)-2,5-dihydro-3-methyl-5-oxo-1H-pyrazol-4-yl]-3,5,6,7-tetrahydro-6,6-dimethyl-1-phenyl-3-trifluoromethyl-1H-indole-2,4-dione, 3-[2,5-dihydro-3-methyl-5-oxo-1-(4-trifluoromethoxyphenyl)-1H-pyrazol-4-yl]-3,5,6,7-tetrahydro-6,6-dimethyl-1-phenyl-3-trifluoromethyl-1H-indole-2,4-dione, 3-(2,5-dihydro-3-methyl-1-(3,5-dimethylphenyl)-5-oxo-1H-pyrazol-4-yl)-3,5,6,7-tetrahydro-6,6-dimethyl-1-phenyl-3-trifluoromethyl-1H-indole-2,4-dione, 3-[1-(4-cyclohexylphenyl)-2,5-dihydro-3-methyl-5-oxo-1H-pyrazol-4-yl]-3,5,6,7-tetrahydro-6,6-dimethyl-1-phenyl-3-trifluoromethyl-1H-indole-2,4-dione, 3-[1-(4-benzylphenyl)-2,5-dihydro-3-methyl-5-oxo-1H-pyrazol-4-yl]-3,5,6,7-tetrahydro-6,6-dimethyl-1-phenyl-3-trifluoromethyl-1H-indole-2,4-dione, 3-[2,5-dihydro-1-(4-isopropoxyphenyl)-3-methyl-5-oxo-1H-pyrazol-4-yl]-3,5,6,7-tetrahydro-6,6-dimethyl-1-phenyl-3-trifluoromethyl-1H-indole-2,4-dione, 3-[2,5-dihydro-3-methyl-5-oxo-1-(4-phenoxyphenyl)-1H-pyrazol-4-yl]-3,5,6,7-tetrahydro-6,6-dimethyl-1-phenyl-3-trifluoromethyl-1H-indole-2,4-dione, 3-[2,5-dihydro-3-methyl-5-oxo-1-(biphenyl-4-yl)-1H-pyrazol-4-yl]-3,5,6,7-tetrahydro-6,6-dimethyl-1-phenyl-3-trifluoromethyl-1H-indole-2,4-dione, 3-[1-(3,5-dichlorophenyl)-2,5-dihydro-3-methyl-5-oxo-1H-pyrazol-4-yl]-3,5,6,7-tetrahydro-6,6-dimethyl-1-phenyl-3-trifluoromethyl-1H-indole-2,4-dione or 3-[2,5-dihydro-3-methyl-(4-methylsulfonylphenyl)-5-oxo-1H-pyrazol-4-yl]-3,5,6,7-tetrahydro-6,6-dimethyl-1-phenyl-3-trifluoromethyl-1H-indole-2,4-dione, or a salt thereof, etc.

In addition, the following compounds have been publicly known:

3-(2,5-dihydro-3-methyl-5-oxo-1-phenyl-1H-pyrazol-4-yl)-3,5,6,7-tetrahydro-6,6-dimethyl-1-phenyl-3-trifluoromethyl-1H-indole-2,4-dione, 3-(2,5-dihydro-3-methyl-5-oxo-1-phenyl-1H-pyrazol-4-yl)-3,5,6,7-tetrahydro-6,6-dimethyl-1-phenylmethyl-3-trifluoromethyl-1H-indole-2,4-dione, 1-(4-fluorophenyl)-3-(2,5-dihydro-3-methyl-5-oxo-1-phenyl-1H-pyrazol-4-yl)-3,5,6,7-tetrahydro-6,6-dimethyl-3-trifluoromethyl-1H-indole-2,4-dione, 3-(2,5-dihydro-3-methyl-5-oxo-1-phenyl-1H-pyrazol-4-yl)-3,5,6,7-tetrahydro-1-(4-methoxyphenyl)-6,6-dimethyl-3-trifluoromethyl-1H-indole-2,4-dione, and 1-(3-chlorophenyl)-3-(2,5-dihydro-3-methyl-5-oxo-1-phenyl-1H-pyrazol-4-yl)-3,5,6,7-tetrahydro-6,6-dimethyl-3-trifluoromethyl-1H-indole-2,4-dione.

Next, methods for producing the compounds according to the invention will be described.

The compounds (I) according to the invention can be produced by, for example, the following production methods or the methods shown in Production Examples and Referential Examples, etc., however the methods for producing the compounds according to the invention are not restricted to these reaction examples.

Production method 1

A compound represented by the general formula (II):

[Chemical Formula 10]

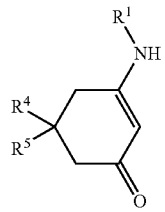

(II)

wherein $R^1$, $R^4$ and $R^5$ each has the meaning as described above; is reacted with a compound represented by the general formula (III):

[Chemical Formula 11]

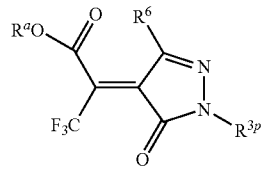

(III)

wherein $R^a$ represents an ester residue; $R^{3p}$ represents a hydrogen atom, a lower cycloalkyl group, an aryl group, a heteroaryl group or a lower alkyl group optionally substituted by a substituent selected from the group consisting of a lower cycloalkyl group, an aryl group and a heteroaryl group, wherein the lower cycloalkyl group, aryl group and heteroaryl group in $R^3$ each independently represents an unsubstituted group or a lower cycloalkyl group, an aryl group or a heteroaryl group substituted by one or two substituents selected from the group consisting of a halogen atom, a nitro group, a cyano group, a lower alkyl group, a lower haloalkyl group, a lower alkoxy group, a lower haloalkoxy group, an optionally protected carboxyl group, a lower cycloalkyl group, an aryl group, a heteroaryl group, an aryloxy group, an aralkyl group, —CON($R^{7ap}$)$R^{8ap}$, —N($R^{7ap}$)$R^{8ap}$, —N($R^{7ap}$)COR$^8$, —N($R^{7ap}$)SO$_2$R$^8$, —OCOR$^7$, —OCON($R^{7ap}$)$R^{8ap}$, —SR$^{7bp}$, —SO$_2$R$^7$, —SO$_2$N($R^{7ap}$)$R^{8ap}$ and

[Chemical Formula 12]

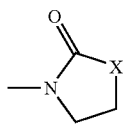

wherein $R^7$ and $R^8$ each independently represents a hydrogen atom or a lower alkyl group; $R^{7ap}$ and $R^{8ap}$ each independently represents a protecting group for amino group or imino group, a hydrogen atom or a lower alkyl group; $R^{7bp}$ represents a protecting group for thiol, a hydrogen atom or a lower alkyl group; X represents —N($R^{7ap}$)— or —O—; and $R^6$ has the meaning as defined above. Thus, a compound represented by the general formula (IV):

[Chemical Formula 13]

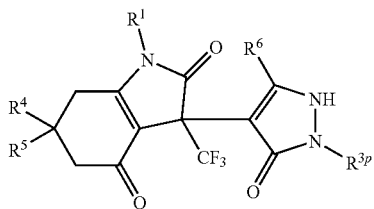

(IV)

wherein $R^1$, $R^{3p}$, $R^4$, $R^5$ and $R^6$ each has the meaning as defined above; is obtained. In the case where this compound (IV) has a protective group, the protective group is removed. Thus, a compound represented by the general formula (I-1) can be produced:

[Chemical Formula 14]

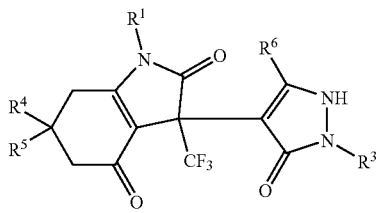

(I-1)

wherein $R^1$, $R^3$, $R^4$, $R^5$ and $R^6$ each has the meaning as defined above.

This production method is a method of producing a compound which corresponds to the compound represented by the general formula (I) wherein $R^2$ is a hydrogen atom, i.e., the compound represented by the general formula (I-1).

The ester residue represented by $R^a$ is not particularly restricted so long as it is usable in so-called condensation reactions in the field of organic chemistry and exerts no undesirable effect on the preceding reaction. Examples thereof include a lower alkyl group such as a methyl group, an ethyl group, a propyl group, an isopropyl group, a butyl group, a sec-butyl group, and a tert-butyl group; an aryl group such as a phenyl group, and a tolyl group; and an aralkyl group such as a benzyl group. Among them, a methyl group and so on are preferred.

In the case where the reactants in the above-described reaction contain an amino group, an imino group, a mercapto group, a carboxyl group or the like not participating in the reaction, it is possible that such amino group, imino group, mercapto group or carboxyl group is optionally protected by a protecting group for amino group or imino group or a protecting group for thiol or carboxyl group and then the reaction is conducted followed by the removal of the preceding protecting group.

Examples of "protecting group for amino group or imino group" include an aralkyl group such as a benzyl group, a p-methoxybenzyl group, a 3,4-dimethoxybenzyl group, an o-nitrobenzyl group, a p-nitrobenzyl group, a benzhydryl group, and a trityl group; a lower alkanoyl group such as a formyl group, an acetyl group, a propionyl group, a butyryl group, and a pivaloyl group; a benzoyl group; an arylalkanoyl group such as a phenylacetyl group, and a phenoxyacetyl group; a lower alkoxycarbonyl group such as a methoxycarbonyl group, an ethoxycarbonyl group, a propyloxycarbonyl group, and a tert-butoxycarbonyl group; an aralkyloxycarbonyl group such as a benzyloxycarbonyl group, a p-nitrobenzyloxycarbonyl group, and a phenethyloxycarbonyl group; and a lower alkylsilyl group such as a trimethylsilyl group, and a tert-butyldimethylsilyl group. Particularly preferred are an acetyl group, a pivaloyl group, a benzoyl group, an ethoxycarbonyl group, a tert-butoxycarbonyl group and so on.

Examples of "protecting group for thiol" include a lower alkylsilyl group such as a trimethylsilyl group, and a tert-butyldimethylsilyl group; a lower alkoxymethyl group such as a methoxymethyl group, and a 2-methoxyethoxymethyl group; a tetrahydropyranyl group; a trimethylsilylethoxymethyl group; an aralkyl group such as a benzyl group, a p-methoxybenzyl group, a 2,3-dimethoxybenzyl group, an o-nitrobenzyl group, a p-nitrobenzyl group, and a trityl group; an acyl group such as a formyl group, and an acetyl group; and so on. Particularly preferred are a methoxymethyl group, a tetrahydropyranyl group, a trityl group, a trimethylsilylethoxymethyl group, a tert-butyldimethylsilyl group, an acetyl group and so on.

Preferred examples of "protecting group for carboxyl group" include a lower alkyl group such as a methyl group, an ethyl group, a propyl group, an isopropyl group, and a tert-butyl group; a lower haloalkyl group such as a 2,2,2-trichloroethyl group; a lower alkenyl group such as a 2-propenyl group; an aralkyl group such as a benzyl group, a p-methoxybenzyl group, a p-nitrobenzyl group, a benzhydryl group, and a trityl group; and so on. Particularly preferred are a methyl group, an ethyl group, a tert-butyl group, a 2-propenyl group, a benzyl group, a p-methoxybenzyl group, a benzhydryl group and so on.

In the reaction between the compound represented by the general formula (II) and the compound represented by the general formula (III), the compound (III) is usually used in an equimolar amount to in excess (preferably equimolar to 1.5 mol) per mol of the compound (II).

The reaction is usually conducted in an inert solvent. Examples of the inert solvent include toluene, benzene, methylene chloride, chloroform, tetrahydrofuran, dioxane, dimethylformamide, N-methylpyrrolidone, dimethyl sulfoxide and a mixture thereof. Still preferred are chloroform and so on.

The reaction temperature ranges usually from 0° C. to the boiling point of the solvent employed in the reaction. Room temperature is preferred.

The reaction time is usually from 5 minutes to 7 days, preferably from 2 hours to 24 hours.

After the completion of the reaction, a treatment common employed is conducted and thus a crude product of the compound represented by the general formula (IV) can be obtained. The thus obtained compound represented by the general formula (IV) is optionally purified in accordance with a conventional method. In the case where the compound has protecting group(s) for amino group, imino group, thiol and/or carboxyl group, reaction(s) for removing the protecting group(s) for amino group, imino group, thiol and/or carboxyl group may be conducted in combination. Thus, the compound of the general formula (I-1) can be produced.

Although the method of removing a protecting group differs depending on the type of the protecting group, the stability of the target compound (I) and so on, it is carried out in accordance with, for example, the methods described in document *Protective Groups in Organic Synthesis*, T. W. Greene, John Wiley & Sons (1981) or similar methods, for example, solvolysis using an acid or a base, i.e., a method which comprises treating the preceding compound with an acid (preferably trifluoroacetic acid, formic acid, hydrochloric acid, etc.) in an amount of 0.01 mol to large excess or a base (preferably potassium hydroxide, calcium hydroxide, etc.) in an equimolar amount to large excess; chemical reduction using a metal hydride complex, etc.; catalytic reduction using a palladium-carbon catalyst, a Raney nickel catalyst, etc.; and so on.

The compound of the general formula (I-1) can be readily isolated and purified by a conventional separation procedure. Examples of the procedure include solvent-extraction, recrystallization, column chromatography, preparative thin layer chromatography and so on.

These compounds can be converted into pharmaceutically acceptable salts by conventional methods. On the contrary, such salts can be converted into free compounds by conventional methods too.

Production method 2

A compound represented by the general formula (IV)

[Chemical Formula 15]

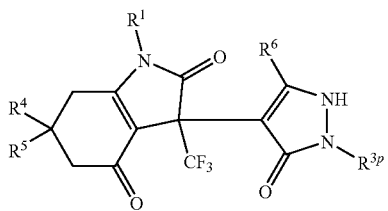

(IV)

wherein $R^1$, $R^{3p}$, $R^4$, $R^5$ and $R^6$ each has the meaning as defined above; and a compound represented by the general formula (V):

[Chemical Formula 16]

$R^{20}$-L (V)

wherein L represents a leaving group; and $R^{20}$ represents a lower cycloalkyl group, an aryl group, a heteroaryl group or a lower alkyl group optionally substituted by a substituent selected from the group consisting of a lower cycloalkyl group, an aryl group and a heteroaryl group; wherein the above-described lower cycloalkyl group, aryl group and heteroaryl group may be each independently substituted by a substituent selected from the group consisting of a halogen atom, a lower alkyl group, a lower haloalkyl group and a lower alkoxy group; are reacted to thereby give a compound represented by the general formula (VI)

[Chemical Formula 17]

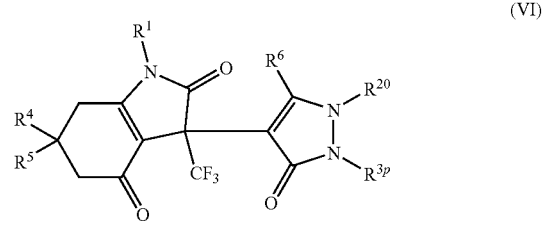

(VI)

wherein $R^1$, $R^{20}$, $R^{3p}$, $R^4$, $R^5$ and $R^6$ each has the meaning as defined above. In the case where this compound (VI) has a protective group, the protective group is removed. Thus, a compound represented by the general formula (I-2) can be produced:

[Chemical Formula 18]

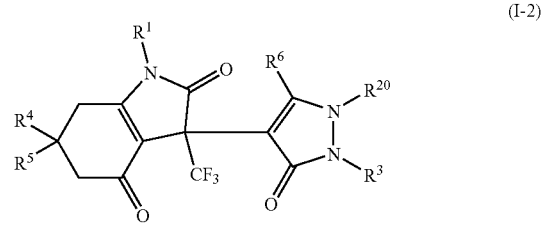

(I-2)

wherein $R^1$, $R^{20}$, $R^3$, $R^4$, $R^5$ and $R^6$ each has the meaning as defined above.

This production method is a method of producing a compound which corresponds to the compound represented by the general formula (I) wherein $R^2$ is a group other than a hydrogen atom, i.e., the compound represented by the general formula (I-2).

Examples of the leaving group represented by L include a halogen atom such as a chlorine atom, a bromine atom, and an iodine atom; an organic sulfonyl group such as a methylsulfinyl group, a methylsulfonyl group, an ethylsulfonyl group, and a phenylsulfonyl group; and an organic sulfonyloxy group such as a methylsulfonyloxy group, a trifluoromethylsulfonyloxy group, and a p-tolylsulfonyloxy group. Preferred are, for example, a halogen atom such as a chlorine atom, a bromine atom, and an iodine atom.

In the reaction between the compound represented by the general formula (IV) and the compound represented by the general formula (V), the compound (V) is usually used in 0.5 mol to in excess (preferably 2.0 mol to 5.0 mol) per mol of the compound (IV).

The reaction is usually conducted in an inert solvent such as tetrahydrofuran, benzene, toluene, acetonitrile, and dimethylformamide in the presence of a base such as sodium hydride, sodium amide, and sodium alkoxide. Alternatively, it may be conducted in a solvent such as methanol, ethanol, and acetonitrile in the presence of a base such as sodium hydroxide, potassium hydroxide, and potassium carbonate, and so on.

The reaction temperature preferably ranges usually from 0° C. to the boiling point of the solvent employed in the reaction. Preferably, the reaction time is usually 1 hour to 48 hours.

After the completion of the reaction, a treatment common employed is conducted and thus a crude product of the compound represented by the general formula (VI) can be obtained. The thus obtained compound represented by the general formula (VI) is optionally purified in accordance with a conventional method. In the case where the compound has protecting group(s) for amino group, imino group, thiol and/or carboxyl group, reaction(s) for removing the protecting group(s) for amino group, imino group, thiol and/or carboxyl group may be conducted in combination. Thus, the compound of the general formula (I-2) can be produced.

The protecting groups can be removed by the same methods as described in the above production method 1.

The compound of the general formula (I-2) can be readily isolated and purified by a conventional separation procedure. Examples of the procedure include solvent-extraction, recrystallization, column chromatography, preparative thin layer chromatography and so on.

These compounds can be converted into pharmaceutically acceptable salts by conventional methods. On the contrary, such salts can be converted into free compounds by conventional methods too.

The compound represented by the general formula (IV) can be produced by the production method 1 as described above. The compound represented by the general formula (IV) that is obtained by the steps of the above production method can be optionally purified and then employed as the starting material of the present production method.

As the compounds represented by the general formula (II), (III) or (V), use can be made of commercially available products. Alternatively, these compounds can be synthesized by combining, if necessary, the methods reported in documents or similar methods or the methods described in the following Production Examples and Referential Examples.

Production method A

[Chemical Formula 19]

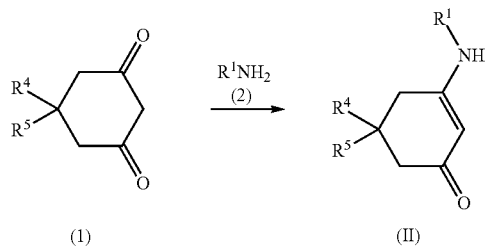

wherein $R^1$, $R^4$ and $R^5$ each has the meaning as defined above.

The production method A is a method of producing the compound represented by the general formula (II).

According to this production method, the compound represented by the general formula (II) can be produced by reacting the compound represented by the formula (1) with the compound represented by the formula (2).

In this reaction, it is possible to apply reaction methods for condensing a ketone carbonyl with a primary amine which are commonly known in the field of organic chemistry. Usually, it can be conducted by reacting the compound (2) in an equimolar amount to in excess per mol of the compound (1) in an inert solvent such as methanol, ethanol, benzene, toluene, ethyl ether, tetrahydrofuran or a mixture thereof.

The reaction temperature ranges usually from 0° C. to the boiling point of the solvent employed in the reaction. Room temperature to 100° C. is preferred.

The reaction time is usually from 5 minutes to 7 days, preferably from 30 minutes to 24 hours.

As the compounds represented by the general formula (1) or (2), use can be made of commercially available products. Alternatively, these compounds can be synthesized by combining, if necessary, publicly known methods or the methods described in the following Production Examples or similar methods thereof.

Production method B

[Chemical Formula 20]

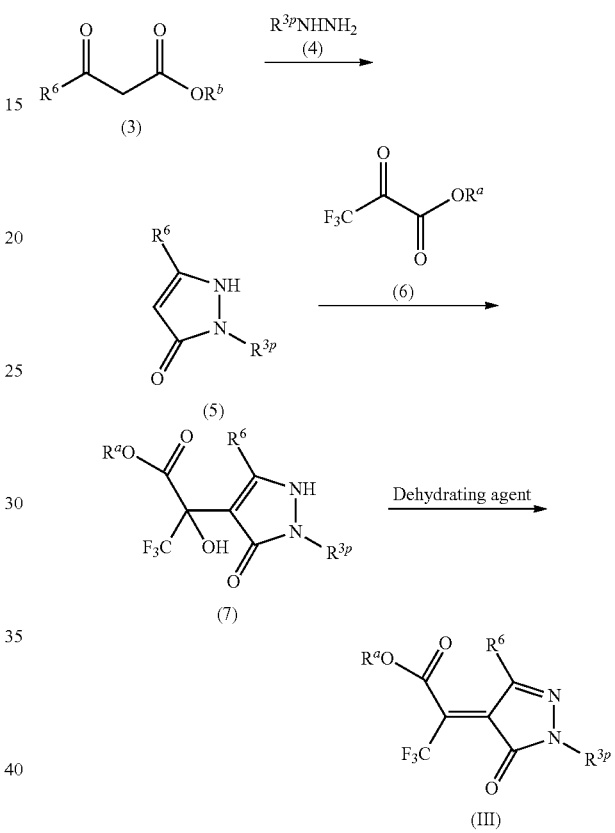

wherein $R^b$ represents an ester residue; and $R^{3p}$, $R^6$ and $R^a$ each has the meaning as defined above.

This production method is a method of producing the compound represented by the general formula (III).

According to this production method, the compound represented by the general formula (III) is produced by reacting the compound represented by the formula (3) with the hydrazine derivative represented by the formula (4) to give the compound represented by the formula (5), then treating the compound represented by the formula (5) with the compound (6) to give the compound (7) and next subjecting the compound (7) to intramolecular dehydration.

As examples of the ester residue represented by $R^b$, the same residues as in the ester residue $R^a$ in production method 1 can be cited. Preferred are also the same.

The step of reacting the compound represented by the formula (3) with the hydrazine derivative represented by the formula (4) to give the compound represented by the formula (5) is usually conducted by using the hydrazine derivative (4) in an amount of 0.5 mol to excess (preferably equimolar to 3.0 mol) per mol of the compound (3).

The reaction is usually conducted in an inert solvent. Preferred examples of the inert solvent include methylene chloride, chloroform, tetrahydrofuran, ethyl ether, methanol, ethanol, benzene, toluene, dimethylformamide, a mixture thereof and so on.

The reaction temperature ranges usually from 0° C. to the boiling point of the solvent employed in the reaction. Room temperature to 100° C. is preferred.

The reaction time is usually from 5 minutes to 7 days, preferably from 30 minutes to 24 hours.

In the step of reacting the compound represented by the formula (5) with the compound represented by the formula (6) to give the compound represented by the formula (7), it is possible to apply reaction methods of the 1,2-addition to a ketone carbonyl which are commonly known per se in the field of organic chemistry. Usually, it can be conducted by using 0.5 mol to excess (preferably equimolar to 3.0 mol) of the compound (6) per mol of the compound (5).

Usually, the reaction is conducted in an inert solvent. Preferred examples of the inert solvent include methylene chloride, chloroform, tetrahydrofuran, ethyl ether, methanol, ethanol, benzene, toluene, dimethylformamide, a mixture thereof and so on.

The reaction temperature ranges usually from 0° C. to the boiling point of the solvent employed in the reaction. Room temperature to 100° C. is preferred.

The reaction time is usually from 5 minutes to 7 days, preferably from 30 minutes to 24 hours.

In the step of producing the compound represented by the formula (III) from the compound represented by the formula (7), it is possible to apply reaction methods of intramolecular dehydration which are commonly known per se in the field of organic chemistry. Usually, it can be conducted by treating the compound (7) with an appropriate dehydrating agent.

Examples of the dehydrating agent include thionyl chloride, hydrogen chloride, sulfuric acid, phosphorus pentaoxide, polyphosphoric acid, paratolenesulfonic acid and so on. Among all, thionyl chloride and the like are preferred.

Usually, the reaction is conducted in an inert solvent. Preferred examples of the inert solvent include chloroform, methylene chloride, pyridine, benzene, toluene, a mixture thereof and so on. In the case of using some dehydrating agents in the above reaction, it is also possible to use such a dehydrating agent both as a reactant and as a solvent.

The reaction temperature ranges usually from 0° C. to the boiling point of the solvent employed in the reaction. Room temperature to 100° C. is preferred.

The reaction time is usually from 5 minutes to 7 days, preferably from 30 minutes to 24 hours.

(Another Method)

Alternatively, the compound represented by the general formula (7) can be produced by the following steps.

[Chemical Formula 21]

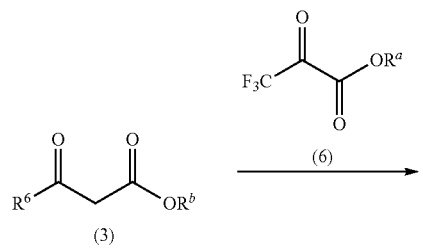

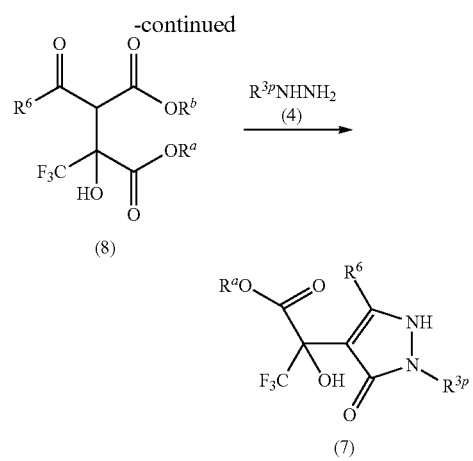

wherein $R^b$, $R^{3p}$, $R^6$ and $R^a$ each has the meaning as described above.

According to this production method, the compound (7) can be produced by reacting the compound represented by the formula (3) with the compound represented by the formula (6) to give the compound represented by the formula (8) and then treating the compound (8) with the hydrazine derivative represented by the formula (4).

The step of reacting the compound represented by the formula (3) with the compound represented by the formula (6) to give the compound represented by the formula (8) is usually conducted by using the compound (6) in an amount of 0.5 mol to excess (preferably equimolar to 3.0 mol) per mol of the compound (3).

The reaction is usually conducted in an inert solvent. Preferred examples of the inert solvent include methylene chloride, chloroform, tetrahydrofuran, ethyl ether, methanol, ethanol, benzene, toluene, dimethylformamide, a mixture thereof and so on.

The reaction temperature ranges usually from 0° C. to the boiling point of the solvent employed in the reaction. Room temperature to 100° C. is preferred.

The reaction time is usually from 5 minutes to 7 days, preferably from 30 minutes to 24 hours.

The step of treating the compound (8) with the hydrazine derivative represented by the formula (4) to give the compound (7) can be conducted in the same manner as in the step of reacting the compound represented by the formula (3) with the hydrazine derivative represented by the formula (4) to give the compound represented by the formula (5) in the above production method. Namely, it is conducted by using the hydrazine derivative (4) in an amount of 0.5 mol to excess (preferably equimolar to 3.0 mol) per mol of the compound (8).

Other conditions including the solvent to be used in the reaction, reaction temperature, reaction time and so on are the same as in the step of producing the compound (5) from the compound (3) as described above.

As the compounds represented by the general formula (3), (4) or (6), use can be made of commercially available products. Alternatively, these compounds can be synthesized by combining, if necessary, publicly known methods or the methods described in the following Production Examples, or similar methods thereof.

The usefulness of the compounds according to the invention as drugs can be proved by, for example, the following Pharmacological Test Examples.

Pharmacological Test Example 1

LCE Enzyme Activity Inhibition Test

A test compound was dissolved in dimethyl sulfoxide (DMSO) to a concentration of 10 mM and then further diluted with DMSO to give a 1000-fold concentrated solution of the compound compared with the assay concentration. The LCE enzyme activity inhibition test was carried out according to a modification of the method of Moon et al., *J. Biol. Chem.*, Vol. 276, pp. 45358 to 45366 (2001). Namely, 1.0 µl of the diluted test compound was added to each well of a 96-well assay plate (Corning, 96-Well Assay Block). Next, 50 µl of a phosphate buffer solution (100 mM potassium phosphate buffer solution, pH 6.5) and 25 µl of a substrate solution (in 100 mM potassium phosphate buffer solution (pH 6.5), 4.0 µM rotenone, 80 µM fatty acid-free bovine serum albumin, 160 µM palmitoyl CoA, 80 µM malonyl CoA, 3.5 µM [$^{14}$C]-malonyl CoA (1.92 GBq/mmol, manufactured by Amersham) were added to each well. Further, 25 µl of an enzyme solution (in 100 mM potassium phosphate buffer solution (pH 6.5), 100 µg/ml human LCE) was added thereto. Then, the upper side of the plate was sealed up, and the plate was incubated with gently stirring at 37° C. for 90 minutes. Subsequently, 100 µl of 5 N HCl was added to each well. The reaction was ceased by stirring the assay plate at room temperature for 5 minutes and acyl CoA was hydrolyzed. Subsequently, the enzyme reaction solution in each well was adsorbed by each well of a 96-well GF/C filter plate (Perkin Elmer Unifilter 96GF/C) through which water had been preliminarily passed. After washing each well with water to remove unabsorbed malonyl CoA, the GF/C filter plate was dried at 50° C. for 60 minutes. Next, 30 µl of a scintilator (Perkin Elmer, Microschinti 0) was added to each well and the upper side of the plate was sealed up. The radioactivity of the thus fixed [$^{14}$C] was measured with a microplate scintillation counter (Perkin Elmer, Topcount) and the obtained value was referred to as the enzyme activity. The human LCE enzyme inhibition activity of the test compound was calculated, based on the radioactivity of the well containing test compound-free DMSO as a control.

The activities of the compounds according to the invention were examined by this assay. As a result, these compounds inhibit human LCE activity. Table 1 shows the results.

TABLE 1

| Compound | LCE enzyme inhibition activity (IC50, nM) |
|---|---|
| Production Example 23 | 9.5 |
| Production Example 26 | 16.5 |
| Production Example 29 | 23 |
| Production Example 31 | 17 |
| Production Example 32 | 9.7 |
| Production Example 33 | 11.0 |
| Production Example 35 | 15 |
| Production Example 36 | 11 |
| Production Example 40 | 30 |
| Production Example 42 | 22 |
| Production Example 44 | 8.9 |

Pharmacological Test Example 2

Intracellular LCE Activity Inhibition Test

Cultured H2.35 cells originating in mouse liver were maintained in DMEM (GIBCO) containing 4% calf serum and 200 nM dexamethasone and cultured at 33° C. in the presence of 5% $CO_2$. About $2.5 \times 10^5$ H2.35 cells were pipetted into a 24-well cell culture plate (Corning, 24-Well Cell Culture Cluster) and cultured overnight at 33° C. in the presence of 5% $CO_2$. Next, a test compound dissolved in dimethyl sulfoxide (DMSO) was added thereto to give the assay concentration. After culturing for 1 hour at 33° C. in the presence of 5% $CO_2$, [$^{14}$C]-palmitoyl CoA (2.13 GBq/mmol, manufactured by Perkin Elmer) was added to each well and culture was conducted for additional 4 hours at 33° C. in the presence of 5% $CO_2$. Next, each well was washed with ice-cooled phosphate-buffered physiological saline and 250 µl of 2M sodium hydroxide was added to cease the reaction. Then, the reaction solution in each well was transferred into a glass test tube and incubated at 70° C. for 1 hour. After adding 100 µl of a 5N hydrogen chloride solution, fatty acids were extracted with petroleum ether. Then [$^{14}$C]-labeled fatty acids were quantified by radio HPLC and the ratio of the amount of fatty acids having carbon chains consisting of 18 carbon atoms to the amount of those having carbon chains consisting of 16 carbon atoms (C18/C16 ratio) was calculated. The intracellular LCE inhibition activity of the test compound was calculated, based on the C18/C16 ratio of the well containing test compound-free DMSO as a control.

The activities of the compounds according to the invention were examined by this assay. As a result, these compounds inhibit intracellular LCE activity. Table 2 shows the results.

TABLE 2

| Compound | Intracellular LCE inhibition activity (IC50, nM) |
|---|---|
| Production Example 23 | 1.8 |
| Production Example 26 | 3.1 |
| Production Example 29 | 1.2 |
| Production Example 31 | 5.4 |
| Production Example 32 | 1.8 |
| Production Example 33 | 4.2 |
| Production Example 35 | 4.2 |
| Production Example 36 | 0.6 |
| Production Example 40 | 38 |
| Production Example 42 | 25 |
| Production Example 44 | 7.0 |

The compounds represented by the general formula (I) or (I-a) can be administered orally and parenterally. After formulating into preparations suitable for intended administration routes, these compounds can be provided as drugs for treating various diseases, for example, circulatory diseases such as hypertension, angina pectoris, heart failure, cardiac infarction, stroke, claudication, diabetic renal failure, diabetic retinopathy, failing vision, electrolyte abnormality and atherosclerosis; central neurological diseases such as bulimia and diabetic neuropathy; metabolic diseases such as metabolic syndrome, obesity, diabetes, insulin resistance, hyperlipidemia, hypercholesterolemia, hypertriglyceridemia, dyslipidemia, non-alcoholic fatty liver, disturbance in hormone secretion, gout and fatty liver; reproductive diseases such as menstrual disorder and sexual dysfunction; digestive tract diseases such as impaired liver function, pancreatitis, cholecystitis and gastro-esophageal reflux; respiratory diseases such as obesity-hypoventilation syndrome (Pickwickian syndrome) and sleep apnea; infections caused by bacteria, fungi and parasites; malignant neoplasm; inflammatory diseases such as arthritis and skin ulcer.

One aspect of the invention provides a method for treating or preventing disorders, diseases or conditions caused by modulation of LCE which comprises administering to a subject in need thereof a therapeutically or prophylactically effective amount of a compound (I) or (I-a) according to the invention or a pharmaceutically acceptable salt thereof.

Another aspect of the invention provides a method for treating or preventing metabolic syndrome, fatty liver, hyperlipidemia, dyslipidemia, non-alcoholic fatty liver, obesity, diabetes, bulimia, malignant neoplasm or an infectious disease which comprises administering to a subject in need thereof a therapeutically or prophylactically effective amount of a compound (I) or (I-a) according to the invention or a pharmaceutically acceptable salt thereof.

Another aspect of the invention provides a method for treating metabolic syndrome, fatty liver, hyperlipidemia, obesity, diabetes, bulimia, malignant neoplasm or infectious diseases, which comprises administering to a subject in need thereof a therapeutically effective amount of a compound (I) or (I-a) according to the invention or a pharmaceutically acceptable salt thereof.

Another aspect of the invention provides a method for treating or preventing diabetes which comprises administering to a subject in need thereof a therapeutically or prophylactically effective amount of a compound (I) or (I-a) according to the invention or a pharmaceutically acceptable salt thereof.

Another aspect of the invention provides a method for treating or preventing obesity which comprises administering to a subject in need thereof a therapeutically or prophylactically effective amount of a compound (I) or (I-a) according to the invention or a pharmaceutically acceptable salt thereof.

Another aspect of the invention provides a method for treating or preventing an obesity-related disease selected from the group consisting of overeating, bulimia, hypertension, elevated plasma insulin concentrations, insulin resistance, hyperlipidemia, endometrial cancer, breast cancer, prostate cancer, colon cancer, kidney cancer, osteoarthritis, obstructive sleep apnea, heart disease, abnormal heart rhythms, arrhythmias, myocardial infarction, congestive heart failure, coronary heart disease, sudden death, stroke, polycystic ovary disease, craniopharyngioma, metabolic syndrome, insulin resistance syndrome, sexual and reproductive dysfunction, infertility, hypogonadism, hirsutism, obesity-related gastro-esophageal reflux, obesity-hypoventilation syndrome (Pickwickian syndrome), inflammation, systemic inflammation of the vasculature, atherosclerosis, hypercholesterolemia, hyperuricaemia, lower back pain, inflammation, systemic inflammation of the vasculature, atherosclerosis, hypercholesterolemia, hyperuricaemia, lower back pain, gallbladder disease, gout, constipation, irritable bowel syndrome, inflammatory bowel syndrome, cardiac hypertrophy, and left ventricular hypertrophy which comprises administering to a subject in need thereof a therapeutically or prophylactically effective amount of a compound (I) or (I-a) according to the invention or a pharmaceutically acceptable salt thereof.

Another aspect of the invention provides a method for treating or preventing hyperlipidemia or dyslipidemia which comprises administering to a subject in need thereof a therapeutically or prophylactically effective amount of a compound (I) or (I-a) according to the invention or a pharmaceutically acceptable salt thereof.

Another aspect of the invention provides a method for caloric intake which comprises administering to a subject in need thereof a therapeutically or prophylactically effective amount of a compound (I) or (I-a) according to the invention or a pharmaceutically acceptable salt thereof.

Another aspect of the invention provides a method for reducing food intake which comprises administering to a subject in need thereof a therapeutically or prophylactically effective amount of a compound (I) or (I-a) according to the invention or a pharmaceutically acceptable salt thereof.

Another aspect of the invention provides a method for increasing satiety which comprises administering to a subject in need thereof a therapeutically or prophylactically effective amount of a compound of formula (I) or (I-a) according to the invention or a pharmaceutically acceptable salt thereof.

Another aspect of the invention provides a method for reducing appetite which comprises administering to a subject in need thereof a therapeutically or prophylactically effective amount of a compound (I) or (I-a) according to the invention or a pharmaceutically acceptable salt thereof.

The invention also relates to methods for treating or preventing obesity which comprises administering a compound (I) or (I-a) according to the invention or a pharmaceutically acceptable salt thereof, in combination with a therapeutically or prophylactically effective amount of another agent that has been known to be useful to treat or prevent the condition.

The invention also relates to methods for treating or preventing diabetes which comprises administering a compound of formula (I) or (I-a) according to the invention or a pharmaceutically acceptable salt thereof, in combination with a therapeutically or prophylactically effective amount of another agent that has been known to be useful to treat or prevent the condition.

The invention also relates to methods for treating or preventing hyperlipidemia or dyslipidemia which comprises administering a compound of formula (I) or (I-a) according to the invention or a pharmaceutically acceptable salt thereof, in combination with a therapeutically or prophylactically effective amount of another agent that has been known to be useful to treat or prevent the condition.

Another aspect of the invention provides a medicinal composition comprising a compound of (I) or (I-a) according to the invention or a pharmaceutically acceptable salt thereof, and a pharmaceutically acceptable carrier.

Yet another aspect of the invention relates to a compound (I) or (I-a) according to the invention or a pharmaceutically acceptable salt thereof, for use in medicine.

Yet another aspect of the invention relates to the use of a compound (I) or (I-a) according to the invention or a pharmaceutically acceptable salt thereof, for the production of a medicine that is useful for the treatment or prevention, or suppression of a disease caused by LCE in a subject in need thereof.

Yet another aspect of the invention relates to the use of a compound (I) or (I-a) according to the invention or a pharmaceutically acceptable salt thereof, for the production of a medicine useful for treating or preventing metabolic syndrome, hyperlipidemia, dyslipidemia, nonalcoholic fatty liver, obesity, diabetes, bulimia, malignant neoplasm or an infectious disease in a subject in need thereof.

Yet another aspect of the invention relates to the use of a compound (I) or (I-a) according to the invention or a pharmaceutically acceptable salt thereof, for the production of a medicine useful for treating or preventing obesity in a subject in need thereof.

Yet another aspect of the invention relates to the use of a compound (I) or (I-a) according to the invention or a pharmaceutically acceptable salt thereof, for the production of a medicine useful for treating or preventing diabetes in a subject in need thereof.

Yet another aspect of the invention relates to the use of a compound (I) or (I-a) according to the invention or a pharmaceutically acceptable salt thereof, for the production of a medicine useful for treating or preventing hyperlipidemia or dyslipidemia in a subject in need thereof.

Yet another aspect of the invention relates to the use of a therapeutically effective amount of a compound (I) or (I-a) according to the invention or a pharmaceutically acceptable salt thereof, and a therapeutically effective amount of an agent selected from the group consisting of an insulin sensitizer, an insulin mimetic, a sulfonylurea, an α-glucosidase inhibitor, a dipeptidyl peptidase 4 (DPP-4 or DP-IV) inhibitor, a glucagons like peptide 1 (GLP-1) agonist, an HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid CB1 receptor antagonist or inverse agonist, a melanin-concentrating hormone receptor agonist, a melanocortin 4 receptor agonist, a bombesin receptor subtype 3 agonist, a ghrelin antagonist, PYY, $PYY_{3-36}$, and an NK1 antagonist, or a pharmaceutically acceptable salt thereof, for the production of a medicine useful for the treatment, control, or prevention of obesity, diabetes, a diabetes related disorder, or an obesity-related disease in a subject in need thereof.

Yet another aspect of the invention relates to the use of a therapeutically effective amount of a compound (I) or (I-a) according to the invention or a pharmaceutically acceptable salt thereof, and a therapeutically effective amount of an agent selected from the group consisting of an insulin sensitizer, an insulin mimetic, a sulfonylurea, an α-glucosidase inhibitor, a dipeptidyl peptidase 4 (DPP-4 or DP-IV) inhibitor, a glucagon-like peptide 1 (GLP-1) agonist, an HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid CB1 receptor antagonist or inverse agonist, a melanin-concentrating hormone receptor agonist, a melanocortin 4 receptor agonist, a bombesin receptor subtype 3 agonist, a ghrelin antagonist, PYY, $PYY_{3-36}$, and an NK-1 antagonist, or a pharmaceutically acceptable salt thereof, for the production of a medicine for treatment or prevention of obesity, diabetes, a diabetes related disorder, or an obesity-related disease which comprises the use of an effective amount of a compound (I) or (I-a) according to the invention or a pharmaceutically acceptable salt thereof, and an effective amount of the agent, together or separately.

Yet another aspect of the invention relates to a product containing a therapeutically effective amount of a compound (I) or (I-a) according to the invention or a pharmaceutically acceptable salt thereof, and a therapeutically effective amount of an agent selected from the group consisting of an insulin sensitizer, an insulin mimetic, a sulfonylurea, an α-glucosidase inhibitor, a dipeptidyl peptidase 4 (DPP-4 or DP-IV) inhibitor, a glucagon-like peptide 1 (GLP-1) agonist, an HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid CB1 receptor antagonist or inverse agonist, a melanin-concentrating hormone receptor agonist, a melanocortin 4 receptor agonist, a bombesin receptor subtype 3 agonist, a ghrelin antagonist, PYY, $PYY_{3-36}$, and an NK-1 antagonist, or a pharmaceutically acceptable salt thereof, as a combined preparation for simultaneous, separate or sequential use in obesity, diabetes, a diabetes related disorder, or an obesity-related disease.

Yet another aspect of the invention relates to the use of a therapeutically effective amount of a compound (I) or (I-a) according to the invention or a pharmaceutically acceptable salt thereof, and a therapeutically effective amount of an agent selected from the group consisting of: simvastatin, mevastatin, ezetimibe, atorvastatin, sitagliptin, metformin, sibutramine, orlistat, Qnexa (Product Nama) and phentermine or a pharmaceutically acceptable salt thereof, for the production of a medicine useful for the treatment, control, or prevention of obesity, diabetes, a diabetes related disorder, or an obesity-related disease in a subject in need thereof.

In the clinical use of the compounds of the invention, pharmaceutically-acceptable additives may be added thereto to formulate various preparations in accordance with the intended administration route thereof, and then the preparations may be administered. Various additives generally used in the field of pharmaceutical compositions may be used herein, including, for example, gelatin, lactose, sucrose, titanium oxide, starch, crystalline cellulose, methylcellulose, hydroxypropylmethylcellulose, carboxymethylcellulose, corn starch, microcrystalline wax, white petrolatum, magnesium metasilicate aluminate, anhydrous calcium phosphate, citric acid, trisodium citrate, hydroxypropylcellulose, sorbitol, sorbitan fatty acid esters, polysorbate, sucrose fatty acid esters, polyoxyethylene, hardened castor oil, polyvinylpyrrolidone, magnesium stearate, palmitoleic acid, light silicic acid anhydride, talc, vegetable oils, benzyl alcohol, gum arabic, propylene glycol, polyalkylene glycol, cyclodextrin, and hydroxypropylcyclodextrin.

Examples of the forms of preparations comprising the compound of the invention mixed with such additives include solid preparations such as tablets, capsules, granules, powders and suppositories; and liquid preparations such as syrups, elixirs and injections. These preparations can be produced in any method known in the field of pharmaceutical compositions. The liquid preparations may be in such a form that is dissolved or suspended in water or in any other appropriate vehicles before using. In the case of injections, in particular, the preparation may be dissolved or suspended in a physiological saline or a glucose solution if desired, and a buffer and a preservative may be further added thereto.

The compounds of the invention are effective for animals including humans and other mammals and plants with need for the treatment using the compounds. As the mammals, humans are preferred and they may be either male or female. Examples of the mammals other than humans include companion animals such as dogs and cats. The compounds of the invention are effective also for obesity and obesity-related diseases of dogs and cats. Any ordinary physicians, veterinarians and clinicians may readily determine whether the treatment with the compound of the invention is needed or not.

In the case of using the compound of the invention for, e.g., a clinical purpose, the dose and administration frequency may vary depending on the sex, age, body weight, conditions of the patient, the type and range of the required treatment using the compound, and so on. In oral administration, the dose of the compound may be from 0.01 to 100 mg/kg of adult/day (preferably from 0.03 to 1 mg/kg of adult/day) and the administration frequency is preferably from one to several times. In parenteral administration, the dose may be from 0.001 to 10 mg/kg of adult/day (preferably from 0.001 to 0.1 mg/kg of adult/day, more preferably from 0.01 to 0.1 mg/kg of adult/day) and the administration frequency is preferably from one to several times.

For oral administration, the compositions are preferably provided in the form of tablets containing 1.0 to 1000 mg of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient, since the dose is to be adjusted depending on the conditions of the patient to be treated. The compounds may be administered on a regimen of 1 to 4 times per day, preferably once or twice per day.

In the case of using the compounds of the invention for treating or preventing obesity and/or diabetes and/or hyperlipidemia and/or dyslipidemia and/or non-alcoholic fatty liver or other diseases, satisfactory results can be generally obtained by administering the compounds of the invention in a daily dosage of from about 0.1 mg to about 100 mg per kilogram of animal body weight, preferably in a single daily dose or in divided doses two to six times a day, or as sustained release preparations. In the case of many large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic effects.

Ordinary physicians, veterinarians and clinicians may readily determine the effective dose of the pharmaceutical compound necessary to treat, prevent, inhibit, suppress or stop the target disease and conduct the treatment.

These preparations may contain the compound of the invention in an amount of from 1.0 to 100% by weight, preferably from 1.0 to 60% by weight based on the total preparation. The preparations may contain any other therapeutically-effective compound.

The compounds of the invention may be combined with any other therapeutic agents that are useful for treating various diseases, for example, circulatory diseases such as hypertension, angina pectoris, heart failure, cardiac infarction, stroke, claudication, diabetic renal failure, diabetic retinopathy, failing vision, electrolyte abnormality and atherosclerosis; central neurological diseases such as bulimia and diabetic neuropathy; metabolic diseases such as metabolic syndrome, obesity, diabetes, insulin resistance, hyperlipidemia, hypercholesterolemia, hypertriglyceridemia, dyslipidemia, non-alcoholic fatty liver, disturbance in hormone secretion, gout and fatty liver; reproductive diseases such as menstrual disorder and sexual dysfunction; digestive tract diseases such as impaired liver function, pancreatitis, cholecystitis and gastroesophageal reflux; respiratory diseases such as obesity-hypoventilation syndrome (Pickwickian syndrome) and sleep apnea; infections caused by bacteria, fungi and parasites; malignant neoplasm; inflammatory diseases such as arthritis and skin ulcer. The individual ingredients to be combined may be administered either at the same time or at different times during the treatment period, either as a single preparation or as separate preparations. That is, the invention should be construed as encompassing any administration mode at the same time or at different times, and the administration in the invention should be construed so too. The scope of the combination of the compound of the invention with the other therapeutic agent useful for the treatment of the above-mentioned disorders encompasses, in principle, all combinations of the compounds of the invention with any pharmaceutical agents useful for the treatment of the above-mentioned disorders.

The above-described combination includes not only the compositions of a compound of the invention with one other active substance but also the compositions of a compound of the invention with two or more other active substances. There are a lot of examples of the combinations of a composition of the invention and one, two or more active substances selected from the therapeutic agents for the above-mentioned diseases. For example, in the case of aiming at the treatment, management and prevention of metabolic syndrome, a combination of a composition of the invention and one, two or more active substances selected from hypolipidemic agents, lipid lowering agents and anti-diabetic agents is useful. In particular, a composition which contains an anti-obesity agent and an anti-hypertension agent, in addition to an anti-diabetic agent and/or a hypolipidemic agent or lipid lowering agent, can exhibit a synergistic effect for treatment, management and prevention of metabolic syndrome.

Examples of the pharmaceutical agents to be combined with the compound of the invention include an ACAT inhibitor, an α-blocker, an aldose reductase inhibitor, an α-amylase inhibitor, an angiotensin-converting enzyme inhibitor, an angiotensin receptor antagonist, an anion exchange resin, an anorectic, an antioxidant, an antiplatelet, a β-blocker, a biguanide agent, a calcium antagonist, a CB1 receptor inverse agonist/antagonist, a CETP inhibitor, a cholesterol absorption inhibitor, a DGAT inhibitor, a DP-IV inhibitor, a diuretic, eicosapentaenoic acid, an endothelin antagonist, an FLAP inhibitor, an FXR modulator, a Ghrelin antagonist, a GLP-1 agonist, a GLP-1 secretagogue, a glucagon antagonist, a glucokinase activator, a glucocorticoid receptor ligand, an α-glycosidase inhibitor, a GPAT inhibitor, a histamine-H3 receptor ligand, an HMG-CoA reductase inhibitor, an HSD inhibitor, insulin and insulin mimetics, a kinase inhibitor such as a VEGF inhibitor, and a PDGF inhibitors, leptin, a lipase inhibitor, a 5-LO inhibitor, an LXR ligand, a melanocortin agonist, an MCH antagonist, an MTTP inhibitor, an orexin antagonist, an opioid antagonist, a neuropeptide Y antagonist, a nicotinic acid agonist, a PPAR ligand, a PTP-1B inhibitor, an SCD-1 inhibitor, a serotonin transporter inhibitor, an SGLT inhibitor, an SUR ligand, a thyroid hormone agonist, a UCP activator, a VPAC receptor agonist and so on.

More concretely, examples of the other active ingredients that can be combined with the composition of the invention as separate or the same pharmaceutical compositions are as follows, though the invention is not restricted thereto.

(a) Anti-diabetic agents, for example, (1) glitazones (e.g., ciglitazone, darglitazone, englitazone, isaglitazone (MCC-555), pioglitazone, rosiglitazone, troglitazone, tularik, BRL49653, CLX-0921, 5-BTZD and so on), and PPAR-γ agonists such as GW-0207, LG-100641, and LY-300512; (2) biguanides such as buformin, metformin, and phenformin; (3) protein tyrosine phosphatase-1B (PTP-1B) inhibitors; (4) sulfonylureas such as acetohexamide, chlorpropamide, diabinese, glibenclamide, glipizide, glyburide, glimepiride, gliclazide, glipentide, gliquidone, glisolamide, tolazamide, and tolbutamide; (5) meglitinides such as repaglinide, and nateglinide; (6) α-glucosidase hydroxylase inhibitors such as acarbose, adiposine, camiglibose, emiglitate, miglitol, voglibose, pradimicin-Q, salbostatin, CKD-711, MDL-25,637, MDL-73,945, and MOR14; (7) α-amylase inhibitors such as tendamistat, trestatin, and A1-3688; (8) insulin secretagogues such as linogliride, and A-4166; (9) fatty acid oxidation inhibitors such as clomoxir, and etomoxir; (10) α2 antagonists such as midaglizole, isaglidole, deriglidole, idazoxan, earoxan, and fluparoxan; (11) insulin and insulin mimetics such as biota, LP-100, novarapid, insulin detemir, insulin lispro, insulin glargine, insulin zinc suspension (lente and ultralente), Lys-Pro insulin, GLP-1 (73-7) (insulintropin), and GLP-1 (7-36)-$NH_2$; (12) non-thiazolidinediones such as JT-501, farglitazar (GW-2570/GI-262579), and muraglitazar; PPAR α/δ dual agonists such as muraglitazar and the compounds disclosed in U.S. Pat. No. 6,414,002; (13) PPAR-α/γ dual agonists such as MK-0767/KRP-297, CLX-0940, GW-1536, GW-1929, GW-2433, L-796449, LR-90, and SB219994; (14) other insulin sensitizers; (15) VPAC2 receptor agonists; (16) glucokinase activators; and (17) DPP-4 inhibitors, such as sitagliptin (Januvia™), isoleucine thiazolidide (P32/98), NVP-DPP-728, vildagliptin (LAF 237), P93/01, denagliptin (GSK 823093), SYR322, RO 0730699, TA-6666, and saxagliptin (BMS 477118).

(b) Lipid lowering agents, for example, (1) bile acid sequestrants such as cholestyramine, colesevelam, colestipol, dialkylaminoalkyl derivatives of a cross-linked dextran, Colestid™, LoCholest™, and Questran™; (2) HMG-CoA reductase inhibitors such as atorvastatin, itavastatin, fluvastatin, lovastatin, pitavastatin, pravastatin, rivastatin, rosuvastatin, simvastatin, and ZD-4522; (3) HMG-CoA synthase inhibitors; (4) cholesterol absorption inhibitors such as stanol esters, β-sitosterol, sterol glycosides such as tiqueside, azetidinones such as ezetimibe; (5) acyl coenzyme A-cholesterol acyl-transferase (ACAT) inhibitors such as avasimibe, efiucimibe, KY505, and SMP797; (6) CETP inhibitors such as JTT705, torcetrapib, CP532 and 632, BAY63-2149, SC591, and SC795; (7) squalene synthase inhibitors; (8) antioxidants such as probucol; (9) PPARα agoists such as beclofibrate, benzafibrate, ciprofibrate, clofibrate, etofibrate, fenofibrate, gemcabene, gemfibrozil, and other fibric acid derivatives, e.g., GW7647, BM170744, LY518674, Atromid™, Lopid™, Tricor™ and so on and compounds described in WO 97/36579; (10) FXR receptor modulators such as GW4064, SR103912; (11) LXR receptor ligands such as GW3965, T9013137, and XTCO179628; (12) lipoprotein synthesis inhibitors such as niacin; (13) renin/angiotensin system inhibitors; (14) PPARδ partial agonists; (15) bile acid reabsorption inhibitors such as BARI1453, SC435, PHA384640, S8921, and AZD7706; (16) PPARδ agonists such as GW501516, GW590735, and compounds described in WO97/28149; (17) triglyceride synthesis inhibitors; (18) microsomal triglyceride transport (MTTP) inhibitors such as inplitapide, LAB687, and CP346086; (19) transcription modulators; (20) squalene epoxidase inhibitors; (21) low-density lipoprotein (LDL) receptor inducers; (22) platelet aggregation inhibitors; (23) 5-LO or FLAP inhibitors; and (24) niacin receptor agonists; and so on.

(c) Anti-hypertensive agents, for example, (1) diuretics such as thiazides including chlorthalidone, chlorothiazide, dichlorphenamide, hydroflumethiazide, indapamide, hydrochlorothiazide and so on; loop diuretics such as bumetanide, ethacrynic acid, furosemide and torsemide; potassium sparing agents such as amiloride and triamterene; aldosterone antagonists such as spironolactone, and epirenone; (2) β-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol; (3) calcium channel blockers such as amlodipine, aranidipine, azelnidipine, bamidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodipine, nisoldipine, nitrendipine, manidipine, pranidipine, and verapamil; (4) angiotensin converting enzyme (ACE) inhibitors such as benazepril, captopril, cilazapril, delapril, enalapril, fosinopril, imidapril, lisinopril, moexipril, quinapril, quinaprilat, ramipril, perindopril, perindropril, quanipril, spirapril, tenocapril, trandolapril, and zofenopril; (5) neutral endopeptidase inhibitors such as omapatrilat, cadoxatril, ecadotril, fosidotril, sampatrilat, AVE7688, and ER4030; (6) endothelin antagonists such as bosentan, tezosentan, A308165, and YM62899; (7) vasodilators such as hydralazine, clonidine, minoxidil, and nicotinyl alcohol; (8) angiotensin II receptor antagonists such as candesartan, eprosartan, irbesartan, losartan, pratosartan, tasosartan, telmisartan, valsartan, EXP-3137, FI6828K, and RNH6270; (9) α/β-adrenergic blockers such as nipradilol, arotinolol, and amosulalol; (10) α1-blockers such as terazosin, urapidil, prazosin, bunazosin, trimazosin, doxazosin, naftopidil, indoramin, WHIP 164, and XEN010; (11) α2-agonists such as lofexidine, tiamenidine, moxonidine, rilmenidine, and guanobenz; (12) aldosterone inhibitors; and so on, and (d) Anti-obesity agents, for example, (1) 5HT (serotonin) transporter inhibitors such as paroxetine, fluoxetine, fenfluramine, fluvoxamine, sertraline, and imipramine; (2) NE (norepinephrine) transporter inhibitors such as GW320659, despiramine, talsupram and nomifensine; (3) CB-1 (cannabinoid-1 receptor) antagonists/inverse agonists such as rimonabant (Sanofi Synthelabo), SR-147778 (Sanofi Synthelabo), BAY65-2520 (Bayer), SLV319 (Solvey); and the compounds disclosed in U.S. Pat. Nos. 5,532,237, 4,973,587, 5,013,837, 5,081,122, 5,112,820, 5,292,736, 5,624,941 and 6,028,084, WO96/33159, WO98/33765, WO98/43636, WO98/43635, WO01/09120, WO01/96330, WO98/31227, WO98/41519, WO98/37061, WO00/10967, WO00/10968, WO97/29079, WO99/02499, WO01/58869, WO02/076949, WO01/64632, WO01/64633, WO01/64634, WO03/006007, WO03/007887, WO04/048317, WO05/000809 and EPO NO. EP-658546, EP 656354 and EP 576357; (4) ghrelin antagonists such as those disclosed in WO01/87335 and WO02/08250; (5) H3 (histamine H3) antagonists/inverse agonists such as thioperamide, 3-(1H-imidazol-4-yl)propyl N-(4-pentenyl)carbamate, clobenpropit, iodophenpropit, imoproxifan, GT2394 (Gliatech), A331440, those disclosed in WO02/15905, O-[3-(1H-imidazol-4-yl)propanol]carbamates (Kiec-Kononowicz, K. et al., *Pharmazie*, 55:349-355 (2000)), piperidine-containing histamine H3-receptor antagonists (Lazewska, D. et al., *Pharmazie*, 56:927-932 (2001)), benzophenone derivatives and related compounds (Sasse, A. et al., *Arch. Pharm. (Weinheim)* 334:45-52 (2001)), substituted N-phenylcarbamates (Reidemeister, S. et al., *Pharmazie*, 55:83-86 (2000)), and proxifan derivatives (Sasse, A. et al., *J. Med. Chem.*, 43:3335-3343 (2000)); (6) melanin-concentrating hormone-1 receptor (MCH1R) antagonists such as T-226296 (Takeda), SNP-7941 (Synaptic), those disclosed in WO01/82925, WO01/87834, WO02/051809, WO02/06245, WO02/076929, WO02/076947, WO02/04433, WO02/51809, WO02/083134, WO02/094799, WO03/004027, and Japanese Patent Application No. JP 13226269 and JP 2004-139909; (7) MCH2R (melanin-concentrating hormone 2R) agonists/antagonists; (8) NPY1 (neuropeptide Y Y1) antagonists such as BIBP3226, 2-[1-(5-chloro-3-isopropyloxycarbonylaminophenyl)ethylamino]-6-[2-(5-ethyl-4-methyl-1,3-thiazol-2-yl)ethyl]-4-morpholinopyridine, BIBO3304, LY-357897, CP-671906, GI-264879A, and those disclosed in U.S. Pat. No. 6,001,836, WO96/14307, WO01/23387, WO99/51600, WO01/85690, WO01/85098, WO01/85173 and WO01/89528; (9) NPY5 (neuropeptide Y Y5) antagonists such as L-152,804, GW-569180A, GW-594884A, GW-587081X, GW-548118X, FR235,208, FR-226928, FR240662, FR252384, 1229U91, GI-264879A, CGP71683A, LY-377897, LY366377, PD-160170, SR-120562A, SR-120819A, JCF-104, H409/22 and the compounds disclosed in U.S. Pat. Nos. 6,057,335, 6,043,246, 6,140,354, 6,166,038, 6,180,653, 6,191,160, 6,258,837, 6,313,298, 6,337,332, 6,329,395, 6,340,683 and U.S. Pat. Nos. 6,326,375, 6,329,395, 6,337,332, 6,335,345, 6,388,077, 6,462,053, 6,649,624 and 6,723,847, EPO EP-01010691 and EP-01044970 and PCT WO97/19682, WO97/20820, WO97/20821, WO97/20822, WO97/20823, WO98/27063, WO00/107409, WO00/185714, WO00/185730, WO00/64880, WO00/68197, WO00/69849, WO01/09120, WO01/14376, WO01/85714, WO01/85730, WO01/07409, WO01/02379, WO01/23388, WO01/23389, WO01/44201, WO01/62737, WO01/62738, WO01/09120, WO02/20488, WO02/22592, WO02/48152, WO02/49648, WO02/094789, WO02/094825, WO03/014083, WO03/10191, WO03/092889, WO2004/002986, WO2004/031175, and Norman et al., *J. Med. Chem.*, 43:4288-4312 (2000); (10) leptins such as recombinant human leptin (PEG-OB, Hoffman La Roche), and recombinant methionyl human leptin (Amgen); (11) leptin derivatives such as those disclosed in U.S. Pat. Nos. 5,552,524, 5,552,523, 5,552,522 and 5,521,283, and PCT WO96/23513, WO96/23514, WO96/23515, WO96/23516, WO96/23517, WO96/23518, WO96/23519 and WO96/23520; (12) opioid antagonists such as nalmefene (Revex™), 3-methoxynaltrexone, naloxone, naltrexone and the compounds disclosed in WO00/21509; (13) orexin antagonists such as SB-334867-A and the compounds disclosed in WO01/96302, WO01/68609, WO02/51232, WO02/51838 and WO03/023561; (14) BRS3 (bombesin receptor subtype 3) agonists such as [D-Phe6,beta-Ala11,Phe13,Nle14]Bn(6-14) and [D-Phe6,Phe13]Bn(6-13)propylamide and those compounds disclosed in *Pept. Sci.*, 2002 August; 8(8): 461-475; (15) CCK-A (cholecystokinin-A) antagonists such as AR-R15849, GI181771, JMV-180, A-71378, A-71623, SR146131 and the compounds disclosed in U.S. Pat. No. 5,739,106; (16) CNTFs (ciliary neurotrophic factors) such as GI-181771 (Glaxo-SmithKline), SR146131 (Sanofi Synthelabo), butabindide and PD 170292 and PD 149164 (Pfizer); (17) CNTF derivatives such as axokine (Regeneron) and the compounds disclosed in WO94/09134, WO98/22128 and WO99/43813; (18) GHS (growth hormone secretagogue receptor) agonists such as NN703, hexarelin, MK-0677, SM-130686, CP-424,391, L-692,429, L-163,255 and the compounds disclosed in U.S. Pat. Nos. 5,536,716 and 6,358,951, USP Application Nos. 2002/049196 and 2002/022637, WO01/56592 and WO02/32888; (19) 5HT2c (serotonin receptor 2c) agonists such as BVT933, DPCA37215, IK264, PNU22394, WAY161503, R-1065, YM348 and the compounds disclosed in U.S. Pat. No. 3,914,250, WO02/36596, WO02/48124, WO02/10169, WO01/66548, WO02/44152, WO02/51844, WO02/40456, and WO02/40457; (20) Mc3r (melanocortin-3 receptor) agonists; (21) Mc4r (melanocortin-4 receptor) agonists such as CHIR86036 (Chiron), ME-10142 and ME-10145 (Melacure), PT-141 and PT-14 (Palatin) and the compounds disclosed in U.S. Pat. Nos. 6,410,548, 6,294,534, 6,350,760, 6,458,790, 6,472,398, 6,376,509, and 6,818,658, USP Application Nos. US2002/0137664, US2003/0236262, US2004/009751, US2004/0092501, WO99/64002, WO00/74679, WO01/991752, WO01/74844, WO01/70708, WO01/70337, WO01/91752, WO02/059095, WO02/059107, WO02/059108, WO02/059117, WO02/12166, WO02/11715, WO02/12178, WO02/15909, WO02/068387, WO02/068388, WO02/067869, WO03/007949, WO03/009847, WO04/024720, WO04/078716, WO04/078717, WO04/087159, WO04/089307 and WO05/009950; (22) monoamine reuptake inhibitors such as sibutratmine (Meridia™/Reductil™) and salts thereof, and the compounds disclosed in U.S. Pat. Nos. 4,746,680, 4,806,570 and 5,436,272, U.S. Patent Publication No. 2002/0006964, and WO01/27068 and WO01/62341; (23) serotonin reuptake inhibitors such as dexfenfluramine, fluoxetine, paroxetine, sertraline, and the compounds disclosed in U.S. Pat. No. 6,365,633, WO01/27060, and WO01/162341; (24) GLP-I (glucagon-like peptide-1) agonists; (25) topiramate (Topimax™); (26) Phytopharm compound 57 (CP644,673); (27) ACC2 (acetyl-CoA carboxylase-2) inhibitors; (28) β3 (β-adrenergic receptor-3) agonists such as AD9677/TAK677 (Dainippon/Takeda), CL-316, 243, SB418790, BRL-37344, L-796568, BMS-196085, BRL-35135A, CGP12177A, BTA-243, GW427353, trecadrine, Zeneca D7114, SR59119A and the compounds disclosed in U.S. Pat. No. 5,705,515, U.S. Pat. No. 5,451,677, WO94/18161, WO95/29159, WO97/46556, WO98/04526, WO98/32753, WO01/74782 and WO02/32897; (29) DGAT1 (diacylglycerol acyltransferase-1) inhibitors; (30) DGAT2 (diacylglycerol acyltransferase-2) inhibitors; (31) FAS (fatty acid synthase) inhibitors such as cerulenin and C75; (32) PDE (phosphodiesterase) inhibitors such as theophylline, pentoxifylline, zaprinast, sildenafil, aminone, milrinone, cilostamide, rolipram and cilomilast; (33) thyroid hormone-β agonists such as KB-2611 (KaroBio BMS), and the compounds disclosed in WO02/15845 and Japanese Patent Application No. JP2000256190; (34) UCP-1 (uncoupling protein-1), 2 or 3 activators such as phytanic acid, 4-[(E)-2-(5,6,7,8-tetrahydro-5,5,8,8-tetramethyl-2-naphthalenyl)-1-propenyl]benzoic acid (TTNPB), retinoic acid, and the compounds disclosed in WO99/00123; (35) acyl-estrogens such as oleoyl-estrones disclosed in del Mar-Grasa, M. et al., *Obesity Research*, 9:202-209 (2001); (36) glucocorticoid antagonists; (37) 11βHSD-1 (11-β-hydroxysteroid dehydrogenase type 1) inhibitors such as BVT3498, BVT2733 and the compounds disclosed in WO01/90091, WO01/90090, WO01/90092, U.S. Pat. No. 6,730,690 and USP Application No. 2004/0133011; (38) SCD-1 (stearoyl-CoA desaturase-1) inhibitors; (39) dipeptidyl peptidase IV (DP-IV) inhibitors such as isoleucine thiazolidide, valine pyrrolidide, NVP-DPP728, LAF237, P93/01, TSL225, TMC-2A/2B/2C, FE999011, P9310/K364, VIP0177, SDZ274-444 and the compounds disclosed in U.S. Pat. No. 6,699,871, WO03/004498, WO03/004496, EP1258476, WO02/083128, WO02/062764, WO03/000250, WO03/002530, WO03/002531, WO03/002553, WO03/002593, WO03/000180 and WO03/000181; (40) lipase inhibitors such as tetrahydrolipstatin (Orlistat/Xenical™), Triton WR1339, RHC80267, lipstatin, teasaponin, diethylumbelliferyl phosphate, FL-386, WAY-121898, Bay-N-3176, valilactone, esteracin, ebelactone A, ebelactone B, RHC80267 and the compounds disclosed in WO01/77094, U.S. Pat. Nos. 4,598,089, 4,452,813, 5,512,565, 5,391,571, 5,602,151, 4,405,644, 4,189,438, and 4,242,453; (41) fatty acid transporter inhibitors; (42) dicarboxylate transporter inhibitors; (43) glucose transporter inhibitors; (44) phosphate transporter inhibitors; (45) melanocortin agonists such as melanotan II and the compounds described in WO99/64002 and WO00/746799; (46) melanin condensating hormone antagonists such as the compounds disclosed in WO01/21577 and WO01/21169; (47) galanin antagonists; (48) CCK agonists; (49) corticotropin-releasing hormone agonists; and (50) phosphodiesterase-3B (PDE3B) inhibitors; (51) 5HT-2 agonists; (52) histamine receptor-3 (H3) modulators; (53) β-hydroxy steroid dehydrogenase-1 (β-HSD-1) inhibitors; (54) anti-obesity serotonergic agents such as fenfluramine, dexfenfluramine, phentermine and sibutramine; (55) peptide YY, PYY 3-36, peptide YY analogs, derivatives and fragments such as BIM-43073D, BIM-43004C (Olitvak, D. A. et al., *Dig. Dis. Sci.* 44(3):643-48 (1999)) and those disclosed in U.S. Pat. Nos. 5,026,685, 5,604,203, 5,574,010, 5,696,093, 5,936,092, 6,046,162, 6,046,167, 6,093,692, 6,225,445, 5,604,203, 4,002,531, 4,179,337, 5,122,614, 5,349,052, 5,552,520, 6,127,355, PCT International Patent Publication Nos. WO95/06058, WO98/32466, WO03/026591, WO03/057235, WO03/027637, and WO2004/066966; (56) NPY2 (neuropeptide Y2) agonists such NPY3-36, N-acetyl-[Leu(28,31)]-NPY 24-36, TASP-V and cyclo-(28/32)-Ac-[Lys28-Glu32]-(25-36)-pNPY; (57) NPY4 (neuropeptide Y4) agonists such as pancreatic peptide (PP) as described in Batterham et al., *J. Clin. Endocrinol. Metab.* 88:3989-3992 (2003) and other Y4 agonists such as 1229U91; (58) cyclooxygenase-2 inhibitors such as etoricoxib, celecoxib, valdecoxib, parecoxib, lumiracoxib, BMS347070, tiracoxib, JTE522, ABT963, CS502 and GW406381, and pharmaceutically acceptable salts thereof; (59) a minorex; (60) amphechloral; (61) amphetamine; (62) benzphetamine; (63) chlorphentermine; (64) clobenzorex; (65) cloforex; (66) clominorex; (67) clortermine; (68) cyclexedrine; (69) dextroamphetamine; (70) diphemethoxidine, (71) N-ethylamphetamine; (72) fenbutrazate; (73) fenisorex; (74) fenproporex; (75) fludorex; (76) fluminorex; (77) furfurylmethylamphetamine; (78) levamfetamine; (79) levophacetoperane; (80) mefenorex; (81) metamfepramone; (82) methamphetamine; (83) norpseudoephedrine; (84) pentorex; (85) phendimetrazine; (86) phenmetrazine; (87) picilorex; (88) zonisamide, and (89) neurokinin-1 receptor antagonists (NK-1 antagonists) such as the compounds disclosed in: U.S. Pat. Nos. 5,162,339, 5,232,929, 5,242,930, 5,373,003, 5,387,595, 5,459,270, 5,494,926, 5,496,833 and 5,637,699; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942, 97/21702, and 97/49710; and (90) Qnexa.

The present agents may be combined with a non-drug therapy such as kinesitherapy, dietetic treatment, and radiation therapy.

The compounds and the combined compositions of the invention are effective for treating and preventing diabetes. The term "diabetes" as used herein includes both insulin-dependent diabetes (i.e., also known as IDDM, type-1 diabetes), and insulin-independent diabetes (i.e., also known as NIDDM, type-2 diabetes).

Diabetes is characterized by a fasting plasma glucose level being 126 mg/dl or more. A diabetic subject has a fasting plasma glucose level of 126 mg/dl or more. Prediabetes is characterized by an impaired fasting plasma glucose (FPG) level of 110 mg/dl or more but not more than 126 mg/dl; or impaired glucose tolerance; or insulin resistance. A prediabetic patient, who shows an impaired fasting plasma glucose (a fasting plasma glucose (FPG) level of 110 mg/dl or more but not more than 126 mg/dl); or impaired glucose tolerance (a 2 hour plasma glucose level of 140 mg/dl or more but not more than 200 mg/dl); or insulin resistance, suffers from an increased risk of developing diabetes.

The compounds and compositions of the invention are useful for treating both type-1 diabetes and type-2 diabetes. The compounds and compositions are particularly useful for treating type-2 diabetes. The compounds and compositions of the invention are particularly useful for treating and/or preventing pre-diabetes. Also, the compounds and compositions of the invention are particularly useful for treating and/or preventing gestational diabetes.

Treatment of diabetes refers to the administration of a compound or composition of the invention to a diabetic subject. One result of the treatment is to reduce an increased glucose concentration. Another result of the treatment is to reduce an increased insulin concentration. Still another result of the treatment is to reduce an increased blood triglyceride concentration.

Still another result of the treatment is to increase insulin sensitivity. Still another result of the treatment may be improving impaired glucose tolerance. Still another result of the treatment is to reduce insulin resistance. Still another result of the treatment is to lower plasma insulin levels. Still another result of the treatment is to improve glycemic control, particularly in type 2 diabetes. Yet another result of the treatment is to increase hepatic insulin sensitivity.

Prevention of diabetes, in particular diabetes associated with obesity, refers to the administration of a compound or combination of composition of the invention to prevent or treat the onset of diabetes in a subject in need thereof. A subject in need of preventing diabetes means a prediabetic subject.

The term "hypertension" as used herein includes essential hypertension, wherein the cause is not known or where hypertension is caused by one or more factors such as changes in both the heart and blood vessels, as well as secondary hypertension wherein the cause is known. The causes of secondary hypertension include obesity but are not limited thereto and also include kidney disease, hormonal disorders and use of certain drugs (for example, oral contraceptives, corticosteroids, cyclosporin and so on). The term "hypertension" encompasses high blood pressure, wherein both the systolic and diastolic pressure levels are elevated, and isolated systolic hypertension wherein only the systolic pressure is elevated to 140 mm Hg or more while the diastolic pressure is less than 90 mm Hg. One result of treatment is to lower the elevated blood pressure.

Dyslipidemias or disorders of lipid metabolism include various conditions characterized by abnormal concentrations of one or more lipids (for example, cholesterol and triglycerides) and/or apolipoproteins (for example, apolipoproteins A, B, C and E) and/or lipoproteins (for example, macromolecular complexes such as LDL, VLDL and IDL that are formed by lipids and apolipoproteins and allow the lipids to circulate in blood). Dyslipidemia includes atherogenic dyslipidemia. Hyperlipidemia is associated with abnormal increases in lipids, LDL and VLDL cholesterol and/or triglyceride levels. A result of the treatment of dyslipidemia including hyperlipidemia is to reduce an increased LDL cholesterol concentration. Another result of the treatment is to increase a lowered concentration of HDL cholesterol. Another result of treatment is to decrease very low density lipoproteins and/or small density LDL.

The term "metabolic syndrome", which is also known as syndrome X, is defined in *Third Report of the National Cholesterol Education Program Expert Panel on Detection, Evaluation and Treatment of High Blood Cholesterol in Adults* (ATP-III) (E. S. Ford et al., JAMA, vol. 287 (3), Jan. 16, 2002, pp 356-359). That is, a person is defined as having metabolic syndrome in the case where he/she has three or more of the following symptoms, i.e., visceral obesity, hypertriglyceridemia, low HDL cholesterol, high blood pressure and high fasting glucose. The criteria for these are defined in ATP-III.

The term "obesity" as used herein means a condition in which there is an excess of body fat, and includes visceral obesity. The definition of obesity is based on the body mass index (BMI), which is calculated as body weight per height in meters squared ($kg/m^2$). In Europeans and Americans, "obesity" refers to a condition wherein an otherwise healthy subject has a BMI of 30 $kg/m^2$ or more, or a condition wherein a subject with at least one complication has a BMI of 27 $kg/m^2$ or more. A person with a risk of obesity is an otherwise healthy subject with a BMI of 25 $kg/m^2$ or more but less than 30 $kg/m^2$ or a subject with at least one complication with a BMI of 25 $kg/m^2$ or more but less than 27 $kg/m^2$.

In Asians, the increased risks associated with obesity occur at a lower BMI than in Europeans and Americans. In Asian countries including Japan, "obesity" means a condition wherein a subject with at least one obesity-induced or obesity-related complication, that requires weight reduction or that would be improved by weight reduction, has a BMI of 25 $kg/m^2$ or more. In Asian countries, a person with a risk of obesity is a subject with a BMI of 23 $kg/m^2$ or more but less than 25 $kg/m^2$.

As used herein, the term "obesity" is meant to encompass all of the above definitions of obesity.

Obesity-induced or obesity-related complications include diabetes, impaired glucose tolerance, insulin resistance syndrome, dyslipidemia, hypertension, hyperuricacidemia, gout, coronary artery disease, myocardial infarction, angina pectoris, sleep apnea syndrome, Pickwickian syndrome, fatty liver, cerebral infarction, cerebral thrombosis, transient ischemic attack, orthopedic disorders, arthritis deformans, lumbodynia, emmeniopathy and infertility, though not restricted thereto. In particular, complications include hypertension, hyperlipidemia, dyslipidemia, impaired glucose intolerance, circulatory disease, sleep apnea, diabetes, and other obesity-related conditions.

Treatment of obesity and obesity-related diseases refers to the administration of the compounds or combined compositions of the invention to reduce or maintain the body weight of an obese subject. One result of the treatment is to begin the reduction of the body weight of an obese subject compared with his/her body weight immediately before the administration of a compound or combined composition of the invention. Another result of the treatment is to begin the reduction of body fat including visceral body fat. Another result of the treatment is to prevent body weight gain. Another result of the treatment is to prevent body weight regain of body weight previously lost as a result of diet, exercise, or pharmacotherapy. Another result of the treatment is to reduce the risk of the occurrence of obesity-related diseases and/or to reduce the severity of the same. The result of the treatment is to reduce food and/or calorie intake by the subject, namely, to reduce total food intake, or the intake of specific components of the diet such as carbohydrates or fats; and/or to inhibit nutrient absorption; and/or to inhibit the lowering in metabolic rate. Another result of the treatment is to alter metabolic rate, namely, to inhibit a lowering in metabolic rate or increase metabolic rate, and/or to minimize the metabolic resistance usually caused by weight loss.

Prevention of obesity and obesity-related diseases means the administration of the compounds or combined compositions of the invention to a subject at risk of obesity to reduce or maintain his/her body weight. One result of the prevention is to reduce the body weight of a subject at risk of obesity relative to his/her body weight immediately before the administration of the compound or combined composition of the invention. Another result of the prevention is to prevent body weight regain of body weight previously lost as a result of diet, exercise, or pharmacotherapy. Another result of the prevention is to prevent obesity from occurring in the case of conducting the treatment prior to the onset of obesity in a subject at risk of obesity. Another result of the prevention is to reduce the risk of the occurrence and/or severity of obesity-related diseases in the case of conducting the treatment prior to the onset of obesity in a subject at risk of obesity. In the case where the treatment is conducted for an already obese subject, it can prevent the occurrence, progression or severity of obesity-related diseases. Examples of the obesity-related diseases include atherosclerosis, Type 2 diabetes, polycystic ovary disease, circulatory diseases, osteoarthritis, dermatological diseases, hypertension, insulin resistance, hypercholesterolemia, hypertriglyceridemia, and cholelithiasis, though the invention is not restricted thereto.

ADVANTAGE OF THE INVENTION

Because of having excellent LCE inhibitory effect, the compounds according to the invention are useful as drugs for treating various diseases in which LCE participates, for example, circulatory diseases, neurological diseases, metabolic diseases, reproductive diseases, digestive tract diseases, neoplasm, infections and so on.

BEST MODE FOR CARRYING OUT THE INVENTION

The invention will be described more concretely with reference to Production Examples and Reference Examples. However, it is to be understood that the invention is not restricted thereto.

EXAMPLES

In Production Examples, thin layer chromatography was carried out by using Silica gel$_{60}$F$_{254}$ (Merck) for the plate and a UV detector for detection. As the silica gel for column, use was made of Wakogel™ C-300 or C-200 (Wako Pure Chemical Industries, Ltd.), FLASH+ cartridge (Biotage) or Chromatorex (FUJI SILYSIA CHEMICAL). MS spectra were measured by using ZQ2000 (Waters). NMR spectrometry was carried out by using dimethyl sulfoxide as the internal standard in the case of measuring in a deuterated dimethyl-sulfoxide solution. Also, a spectrophotometer JNM-AL400 (JEOL), Mercury400 (400 MHz; Varian) or Inova400 (400 MHz; Varian) was employed and the total δ value was expressed in ppm.

Abbreviations in NMR have the following meanings.

s: singlet;

d: doublet;

dd: double doublet;

t: triplet;

dt: double triplet;

q: quartet;

m: multiplet;

br: broad;

J: coupling constant;
Hz: hertz; and
DMSO-d$_6$: deuterated dimethyl sulfoxide.

Production Example 1

Production of 3-(2,5-dihydro-3-methyl-5-oxo-1-phenyl-1H-pyrazol-4-yl)-3,5,6,7-tetrahydro-6,6-dimethyl-1-phenyl-3-trifluoromethyl-1H-indole-2,4-dione (1) Production of 2,5-dihydro-α-hydroxy-3-methyl-5-oxo-1-phenyl-α-(trifluoromethyl)-1H-pyrazole-4-acetic acid methyl ester (Method 1)
To a chloroform solution (30 ml) of 3-methyl-1-phenyl-5-pyrazolone (5.0 g, 28.7 mmol), methyl trifluoropyruvate (3.22 mL, 28.7 mmol) was added at room temperature and the mixture was stirred at 80° C. for 2 hours. After removing the solvent under reduced pressure, the title compound was obtained as a colorless solid (9.48 g).
$^1$HNMR (400 MHz, CDCl$_3$, δ ppm): 2.30 (3H, s), 4.00 (3H, s), 4.06 (1H, s), 7.29 (1H, d, J=7.3 Hz), 7.43 (2H, t, J=8.3 Hz), 7.60-7.70 (2H, m).
(Method 2)
To ethylacetoacetate (651 mg, 5.0 mmol), trifluoropyruvate (858 mg, 5.5 mmol) was added and the mixture was stirred at room temperature for 14 hours. After removing excessive trifluoropyruvate under vacuum, 3-acetyl-2-hydroxy-2-trifluoromethyl-butanedioic acid-4-ethyl-1-methyl ester was obtained as a colorless liquid (1.43 g).
To a toluene solution (20 ml) of the thus obtained 3-acetyl-2-hydroxy-2-trifluoromethyl-butanedioic acid-4-ethyl-1-methyl ester (290.0 mg, 1.01 mmol), phenylhydrazine (110 mg, 1.01 mmol) was added and the mixture was stirred under reflux for 2 hours. The liquid reaction mixture was concentrated under reduced pressure and thus the title compound was obtained as a colorless solid (325 mg).

(2) Production of 2-(1,5-dihydro-3-methyl-5-oxo-1-phenyl-4H-pyrazol-4-ylidene)-3,3,3-trifluoro-propanoic acid methyl ester To a toluene solution (50 ml) of 2,5-dihydro-α-hydroxy-3-methyl-5-oxo-1-phenyl-α-(trifluoromethyl)-1H-pyrazole-4-acetic acid methyl ester (1.5 g, 4.5 mmol), thionyl chloride (2 ml, 22.5 mmol) was added and the mixture was stirred under reflux for 3 hours. After concentrating the liquid reaction mixture under reduced pressure, the title compound was obtained as a reddish brown solid (4.41 g).
$^1$HNMR (400 MHz, CDCl$_3$, δ ppm): 2.41 (3H, s), 4.02 (3H, s), 7.23 (1H, t, J=7.3 Hz), 7.41 (2H, t, J=8.8 Hz), 7.80 (2H, d, J=7.8 Hz)

(3) Production of 3-(2,5-dihydro-3-methyl-5-oxo-1-phenyl-1H-pyrazol-4-yl)-3,5,6,7-tetrahydro-6,6-dimethyl-1-phenyl-3-trifluoromethyl-1H-indole-2,4-dione To a chloroform solution (5 ml) of 2-(1,5-dihydro-3-methyl-5-oxo-1-phenyl-4H-pyrazol-4-ylidene)-3,3,3-trifluoro-propanoic acid methyl ester (565 mg, 1.81 mmol), 5,5-dimethyl-3-phenylamino-2-cyclohexen-1-one (390 mg, 1.81 mmol) was added and the mixture was stirred for 14 hours. After concentrating the liquid reaction mixture under reduced pressure, the residue was purified by silica gel flash column chromatography. Thus, the title compound was obtained as a colorless solid (780 mg).
$^1$HNMR (400 MHz, CDCl$_3$, δ ppm): 1.08 (3H, s), 1.12 (3H, s), 2.10-2.45 (7H, m), 7.28-7.38 (5H, m), 7.45-7.55 (5H, m).
ESI-MS (m/e): 496 [M+H]$^+$.
3-(2,5-dihydro-3-methyl-5-oxo-1-phenyl-1H-pyrazol-4-yl)-3,5,6,7-tetrahydro-6,6-dimethyl-1-phenyl-3-trifluoromethyl-1H-indole-2,4-dione obtained in Production Example 1 was optically resolved by using DAICEL CHIRALPAK AD-H (4.6×150 mm, 5 um, 25° C.) under the following conditions, hexane:EtOH (0.1% TFA)-95:5, flow rate: 0.5 ml/min, UV 250 nm. The fractions with retention times of 11.5 min and 17.6 min were respectively collected and the optically active component with the retention time of 11.5 min was identified as being active.
Compounds of Production Examples 2 to 34 were obtained as in Production Example 1 but replacing 5,5-dimethyl-3-phenylamino-2-cyclohexen-1-one employed in Production Example 1 by the 3-substituted-2-cyclohexen-1-one derivatives as the starting materials corresponding to the respective target compounds and further replacing 2-(1,5-dihydro-3-methyl-5-oxo-1-phenyl-4H-pyrazol-4-ylidene)-3,3,3-trifluoro-propanoic acid methyl ester employed in Production Example 1 by the pyrazolone derivatives available as the starting materials for the respective target compounds.

Production Example 2

Production of 3-(2,5-dihydro-3-methyl-5-oxo-1-phenyl-1H-pyrazol-4-yl)-3,5,6,7-tetrahydro-6,6-dimethyl-1-phenylmethyl-3-trifluoromethyl-1H-indole-2,4-dione The title compound was obtained as in Production Example 1 but using as the starting material 5,5-dimethyl-3-phenylmethylamino-2-cyclohexen-1-one.
$^1$HNMR (400 MHz, CDCl$_3$, δ ppm): 0.99 (3H, s), 1.04 (3H, s), 1.80-2.57 (7H, m), 4.54 (2H, br), 6.95-7.45 (6H, m), 7.59-7.76 (4H, m).
ESI-MS (m/e): 510 [M+H]$^+$.

Production Example 3

Production of 1-(4-fluorophenyl)-3-(2,5-dihydro-3-methyl-5-oxo-1-phenyl-1H-pyrazol-4-yl)-3,5,6,7-tetrahydro-6,6-dimethyl-3-trifluoromethyl-1H-indole-2,4-dione The title compound was obtained as in Production Example 1 but using as the starting material 5,5-dimethyl-3-(4-fluorophenylamino)-2-cyclohexen-1-one. $^1$HNMR (400 MHz, CD$_3$OD, δ ppm): 1.03 (3H, s), 1.11 (3H, s), 2.20-2.40 (m, 4H), 2.45 (3H, m), 7.25-7.40 (4H, m), 7.40-7.50 (4H, m), 7.55 (1H, m).
ESI-MS (m/e): 514 [M+H]$^+$.

Production Example 4

Production of 1-(4-chlorophenyl)-3-(2,5-dihydro-3-methyl-5-oxo-1-phenyl-1H-pyrazol-4-yl)-3,5,6,7-tetrahydro-6,6-dimethyl-3-trifluoromethyl-1H-indole-2,4-dione The title compound was obtained as in Production Example 1 but using as the starting material 3-(4-chlorophenylamino)-5,5-dimethyl-2-cyclohexen-1-one.

¹HNMR (400 MHz, CD₃OD, δ ppm): 1.03 (3H, s), 1.11 (3H, s), 2.20-2.55 (7H, m), 7.25-7.40 (5H, m), 7.40-7.60 (4H, m).
ESI-MS (m/e): 530 [M+H]⁺.

Production Example 5

Production of 3-(2,5-dihydro-3-methyl-5-oxo-1-phenyl-1H-pyrazol-4-yl)-3,5,6,7-tetrahydro-1-(4-methoxyphenyl)-6,6-dimethyl-3-trifluoromethyl-1H-indole-2,4-dione The title compound was obtained as in Production Example 1 but using as the starting material 3-(4-methoxyphenylamino)-5,5-dimethyl-2-cyclohexen-1-one.
¹HNMR (400 MHz, CDCl₃, δ ppm): 1.04 (3H, s), 1.11 (3H, s), 2.20-2.40 (7H, m), 3.86 (3H, s), 6.97-7.06 (2H, m), 7.15-7.30 (3H, m), 7.30-7.40 (3H, m), 7.65 (1H, m).
ESI-MS (m/e): 526 [M+H]⁺.

Production Example 6

Production of 3-(2,5-dihydro-3-methyl-5-oxo-1-phenyl-1H-pyrazol-4-yl)-3,5,6,7-tetrahydro-1-(3-methoxyphenyl)-6,6-dimethyl-3-trifluoromethyl-1H-indole-2,4-dione The title compound was obtained as in Production Example 1 but using as the starting material 3-(3-methoxyphenylamino)-5,5-dimethyl-2-cyclohexen-1-one.
¹HNMR (400 MHz, CDCl₃, δ ppm): 1.10 (3H, s), 1.11 (3H, s), 2.25-2.40 (4H, m), 2.32 (3H, s), 7.15-7.20 (4H, m), 7.23-7.29 (5H, m).
ESI-MS (m/e): 526 [M+H]⁺.

Production Example 7

Production of 1-(3-chlorophenyl)-3-(2,5-dihydro-3-methyl-5-oxo-1-phenyl-1H-pyrazol-4-yl)-3,5,6,7-tetrahydro-6,6-dimethyl-3-trifluoromethyl-1H-indole-2,4-dione The title compound was obtained as in Production Example 1 but using as the starting material 3-(3-chlorophenylamino)-5,5-dimethyl-2-cyclohexen-1-one.
¹HNMR (400 MHz, CD₃OD, δ ppm): 1.06 (3H, s), 1.13 (3H, s), 2.25-2.40 (4H, m), 2.46 (3H, s), 7.29 (2H, t, J=7.3 Hz), 7.38 (1H, d, J=6.8 Hz), 7.46 (2H, t, J=8.3 Hz), 7.30-7.70 (4H, m).
ESI-MS (m/e): 530 [M+H]⁺.

Production Example 8

Production of 3-(2,5-dihydro-3-methyl-5-oxo-1-phenyl-1H-pyrazol-4-yl)-3,5,6,7-tetrahydro-1,6,6,-trimethyl-3-trifluoromethyl-1H-indole-2,4-dione The title compound was obtained as in Production Example 1 but using as the starting material 5,5-dimethyl-3-methylamino-2-cyclohexen-1-one.
¹HNMR (400 MHz, CDCl₃, δ ppm): 1.13 (3H, s), 1.16 (3H, s), 2.21-2.52 (4H, m), 2.55 (3H, s), 3.21 (3H, s), 7.09-7.17 (1H, m), 7.26-7.34 (2H, m), 7.69 (2H, d, J=7.8 Hz).
ESI-MS (m/e): 434 [M+H]⁺.

Production Example 9

Production of 1-ethyl-3-(2,5-dihydro-3-methyl-5-oxo-1-phenyl-1H-pyrazol-4-yl)-3,5,6,7-tetrahydro-6,6-dimethyl-3-trifluoromethyl-1H-indole-2,4-dione The title compound was obtained as in Production Example 1 but using as the starting material 3-ethylamino-5,5-dimethyl-2-cyclohexen-1-one.
¹HNMR (400 MHz, CDCl₃, δ ppm): 1.10-1.40 (9H, m), 2.05 (3H, s), 2.10-2.65 (4H, m), 4.12 (2H, q, J=7.3 Hz), 7.45-7.50 (3H, m), 7.70-7.80 (2H, m).
ESI-MS (m/e): 448 [M+H]⁺.

Production Example 10

Production of 3-(2,5-dihydro-3-methyl-5-oxo-1-phenyl-1H-pyrazol-4-yl)-3,5,6,7-tetrahydro-6,6-dimethyl-1-propyl-3-trifluoromethyl-1H-indole-2,4-dione The title compound was obtained as in Production Example 1 but using as the starting material 5,5-dimethyl-3-propylamino-2-cyclohexen-1-one.
¹HNMR (400 MHz, CDCl₃, δ ppm): 0.95-1.04 (3H, m), 1.09-1.22 (6H, m), 2.03-2.63 (11H, m), 7.33-7.45 (3H, m), 7.67-7.77 (2H, m).
ESI-MS (m/e): 462 [M+H]⁺.

Production Example 11

Production of 3-(2,5-dihydro-3-methyl-5-oxo-1-phenyl-1H-pyrazol-4-yl)-3,5,6,7-tetrahydro-1-isopropyl-6,6-dimethyl-3-trifluoromethyl-1H-indole-2,4-dione The title compound was obtained as in Production Example 1 but using as the starting material 5,5-dimethyl-3-isopropylamino-2-cyclohexen-1-one.
¹HNMR (400 MHz, CDCl₃, δ ppm): 1.10-1.30 (9H, m), 1.52 (3H, s), 1.59 (3H, s), 2.10-2.70 (4H, m), 4.32 (1H, m), 7.34-7.45 (3H, m), 7.66-7.81 (2H, m).
ESI-MS (m/e): 462 [M+H]⁺.

Production Example 12

Production of 1-cyclopropyl-3-(2,5-dihydro-3-methyl-5-oxo-1-phenyl-1H-pyrazol-4-yl)-3,5,6,7-tetrahydro-6,6-dimethyl-3-trifluoromethyl-1H-indole-2,4-dione The title compound was obtained as in Production Example 1 but using as the starting material 3-cyclopropylamino-5,5-dimethyl-2-cyclohexen-1-one.
¹HNMR (400 MHz, CDCl₃, δ ppm): 1.11-1.23 (9H, m), 1.90-2.48 (5H, m), 2.60 (3H, s), 4.27 (1H, br), 7.31-7.47 (3H, m), 7.67-7.76 (2H, m).
ESI-MS (m/e): 460 [M+H]⁺.

Production Example 13

Production of 1-cyclobutyl-3-(2,5-dihydro-3-methyl-5-oxo-1-phenyl-1H-pyrazol-4-yl)-3,5,6,7-tetrahydro-6,6-dimethyl-3-trifluoromethyl-1H-indole-2,4-dione The title compound was obtained as in Production Example 1 but using as the starting material 3-cyclobutylamino-5,5-dimethyl-2-cyclohexen-1-one.

$^1$HNMR (400 MHz, CDCl$_3$, δ ppm): 1.10-1.30 (12H, m), 1.80-2.60 (3H, m), 3.44-3.52 (4H, m), 4.32 (1H, m), 7.34-7.42 (3H, m), 7.61-7.81 (2H, m).
ESI-MS (m/e): 474 [M+H]$^+$.

Production Example 14

Production of 1-cyclopentyl-3-(2,5-dihydro-3-methyl-5-oxo-1-phenyl-1H-pyrazol-4-yl)-3,5,6,7-tetrahydro-6,6-dimethyl-3-trifluoromethyl-1H-indole-2,4-dione The title compound was obtained as in Production Example 1 but using as the starting material cyclopentylamino-5,5-dimethyl-3-2-cyclohexen-1-one.
$^1$HNMR (400 MHz, CDCl$_3$, δ ppm): 1.09-1.12 (13H, m), 2.00-2.50 (6H, m), 2.64-2.75 (3H, m), 7.31-7.47 (3H, m), 7.67-7.76 (2H, m).
ESI-MS (m/e): 488 [M+H]$^+$.

Production Example 15

Production of 1-cyclohexyl-3-(2,5-dihydro-3-methyl-5-oxo-1-phenyl-1H-pyrazol-4-yl)-3,5,6,7-tetrahydro-6,6-dimethyl-3-trifluoromethyl-1H-indole-2,4-dione The title compound was obtained as in Production Example 1 but using as the starting material 3-cyclohexylamino-5,5-dimethyl-2-cyclohexen-1-one.
$^1$HNMR (400 MHz, CDCl$_3$, δ ppm): 1.08-1.23 (12H, m), 1.70-2.60 (12H, m), 7.34-7.45 (3H, m), 7.65-7.78 (2H, m).
ESI-MS (m/e): 502 [M+H]$^+$.

Production Example 16

Production of 3-(2,5-dihydro-3-methyl-5-oxo-1-phenyl-1H-pyrazol-4-yl)-3,5,6,7-tetrahydro-6,6-dimethyl-1-(2-pyridylmethyl)-3-trifluoromethyl-1H-indole-2,4-dione The title compound was obtained as in Production Example 1 but using as the starting material 5,5-dimethyl-3-(2-pyridylmethylamino)-2-cyclohexen-1-one.
$^1$HNMR (400 MHz, CDCl$_3$, δ ppm): 1.08 (6H, s), 2.26 (3H, s), 2.19-2.81 (4H, m), 4.81 (1H, d, J=14.6 Hz), 5.00 (1H, d, J=15.6 Hz), 7.07 (1H, m), 7, 22-7.29 (2H, m), 7.33 (1H, d, J=7.8 Hz), 7.70 (4H, m), 8.50 (1H, d, J=4.4 Hz).
ESI-MS (m/e): 511 [M+H]$^+$.

Production Example 17

Production of 3-(2,5-dihydro-3-methyl-5-oxo-1-phenyl-1H-pyrazol-4-yl)-3,5,6,7-tetrahydro-6,6-dimethyl-1-(3-pyridylmethyl)-3-trifluoromethyl-1H-indole-2,4-dione The title compound was obtained as in Production Example 1 but using as the starting material 5,5-dimethyl-3-(3-pyridylmethylamino)-2-cyclohexen-1-one.
$^1$HNMR (400 MHz, CDCl$_3$, δ ppm): 1.03 (3H, s), 1.06 (3H, s), 2.15-2.56 (7H, m), 4.57 (1H, d, J=17.0 Hz), 5.17 (1H, d, J=16.6 Hz), 7.05-7.22 (1H, m), 7.29-7.38 (2H, m), 7.06-7.76 (4H, m), 8.52-8.61 (2H, m).
ESI-MS (m/e): 511 [M+H]$^+$.

Production Example 18

Production of 3-(2,5-dihydro-3-methyl-5-oxo-1-phenyl-1H-pyrazol-4-yl)-3,5,6,7-tetrahydro-6,6-dimethyl-1-(4-pyridylmethyl)-3-trifluoromethyl-1H-indole-2,4-dione The title compound was obtained as in Production Example 1 but using as the starting material 5,5-dimethyl-3-(4-pyridylmethylamino)-2-cyclohexen-1-one.
$^1$HNMR (400 MHz, CDCl$_3$, δ ppm): 1.06 (3H, s), 1.07 (3H, s), 2.20-2.55 (7H, m), 4.66 (1H, m), 5.16 (1H, m), 7.15-7.23 (3H, m), 7.34-7.43 (2H, m), 7.60-7.70 (1H, m), 7.72 (1H, d, J=8.8 Hz), 8.64 (2H, d, J=4.9 Hz).
ESI-MS (m/e): 511 [M+H]$^+$.

Production Example 19

Production of 3-(3-ethyl-2,5-dihydro-5-oxo-1-phenyl-1H-pyrazol-4-yl)-3,5,6,7-tetrahydro-6,6-dimethyl-1-phenyl-3-trifluoromethyl-1H-indole-2,4-dione The title compound was obtained as in Production Example 1 but using as the starting material 2-(3-ethyl-1,5-dihydro-5-oxo-1-phenyl-4H-pyrazol-4-ylidene)-3,3,3-trifluoro-propanoic acid methyl ester.
$^1$HNMR (400 MHz, CDCl$_3$, δ ppm): 0.79 (3H, s), 1.05 (3H, s), 1.39 (3H, t, J=7.3 Hz), 2.09-2.19 (2H, m), 2.26-2.51 (4H, m), 7.32-7.46 (4H, m), 7.47-7.62 (4H, m), 7.81 (2H, d, J=7.8 Hz).
ESI-MS (m/e): 510 [M+H]$^+$.

Production Example 20

Production of 3-(3-cyclopropyl-2,5-dihydro-5-oxo-1-phenyl-1H-pyrazol-4-yl)-3,5,6,7-tetrahydro-6,6-dimethyl-1-phenyl-3-trifluoromethyl-1H-indole-2,4-dione The title compound was obtained as in Production Example 1 but using as the starting material 2-(3-cyclopropyl-1,5-dihydro-5-oxo-1-phenyl-4H-pyrazol-4-ylidene)-3,3,3-trifluoro-propanoic acid methyl ester.
$^1$HNMR (400 MHz, CDCl$_3$, δ ppm): 0.94-1.27 (8H, m), 1.04 (3H, s), 2.27-2.55 (4H, m), 7.14 (1H, t, J=7.3 Hz), 7.27-7.62 (8H, m), 7.75 (1H, d, J=7.8 Hz).
ESI-MS (m/e): 522 [M+H]$^+$.

Production Example 21

Production of 3-(2,5-dihydro-5-oxo-1-phenyl-3-trifluoromethyl-1H-pyrazol-4-yl)-3,5,6,7-tetrahydro-6,6-dimethyl-1-phenyl-3-trifluoromethyl-1H-indole-2,4-dione The title compound was obtained as in Production Example 1 but using as the starting material 2-(1,5-dihydro-3-trifluoromethyl-5-oxo-1-phenyl-4H-pyrazol-4-ylidene)-3,3,3-trifluoro-propanoic acid methyl ester.
$^1$HNMR (400 MHz, CD$_3$OD, δ ppm): 1.08 (3H, s), 1.10 (3H, s), 2.12-2.26 (2H, m), 2.38-2.47 (2H, m), 7.34-7.59 (5H, m), 7.73-7.80 (1H, m), 7.84-7.90 (4H, m).
ESI-MS (m/e): 550 [M+H]$^+$.

Production Example 22

Production of 3-[1-(3-chlorophenyl)-2,5-dihydro-3-methyl-5-oxo-1H-pyrazol-4-yl]-3,5,6,7-tetrahydro-6,6-dimethyl-1-phenyl-3-trifluoromethyl-1H-indole-2,4-dione The title compound was obtained as in Production Example 1 but using as the starting material 2-[1-(3-chlorophenyl)-1,5-dihydro-3-methyl-5-oxo-4H-pyrazol-4-ylidene]-3,3,3-trifluoro-propanoic acid methyl ester.

$^1$HNMR (400 MHz, CDCl$_3$, δ ppm): 1.04 (3H, s), 1.11 (3H, s), 2.00-2.48 (4H, m), 2.50 (3H, s), 7.13 (1H, d, J=7.8 Hz), 7.12-7.29 (2H, m), 7.31 (1H, d, J=5.4 Hz), 7.41 (1H, d, J=7.3 Hz), 7.47-7.59 (3H, m), 7.74 (1H, d, J=9.3 Hz).

ESI-MS (m/e): 530 [M+H]$^+$.

Production Example 23

Production of 3-[1-(4-chlorophenyl)-2,5-dihydro-3-methyl-5-oxo-1H-pyrazol-4-yl]-3,5,6,7-tetrahydro-6,6-dimethyl-1-phenyl-3-trifluoromethyl-1H-indole-2,4-dione The title compound was obtained as in Production Example 1 but using as the starting material 2-[1-(4-chlorophenyl)-1,5-dihydro-3-methyl-5-oxo-4H-pyrazol-4-ylidene]-3,3,3-trifluoro-propanoic acid methyl ester.

$^1$HNMR (400 MHz, CDCl$_3$, δ ppm): 1.06 (3H, s), 1.12 (3H, s), 2.07-2.17 (2H, m), 2.30-2.47 (2H, m), 2.49 (3H, s), 7.28-7.34 (3H, m), 7.32 (1H, m), 7.50-7.58 (4H, m), 7.77 (1H, d, J=9.2 Hz).

ESI-MS (m/e): 530 [M+H]$^+$.

Production Example 24

Production of 3-[2,5-dihydro-1-(2-methoxyphenyl)-3-methyl-5-oxo-1H-pyrazol-4-yl]-3,5,6,7-tetrahydro-6,6-dimethyl-1-phenyl-3-trifluoromethyl-1H-indole-2,4-dione The title compound was obtained as in Production Example 1 but using as the starting material 2-[1,5-dihydro-1-(2-methoxyphenyl)-3-methyl-5-oxo-4H-pyrazol-4-ylidene]-3,3,3-trifluoro-propanoic acid methyl ester.

$^1$HNMR (400 MHz, CDCl$_3$, δ ppm): 1.05 (3H, s), 1.13 (3H, s), 2.16-2.46 (2H, m), 2.47 (3H, s), 3.90 (3H, s), 6.93-7.05 (2H, m), 7.12-7.26 (1H, m), 7.43-7.53 (4H, m), 7.12-7.26 (1H, m), 7.80 (1H, dd, J=7.8, 1.5 Hz).

ESI-MS (m/e): 526 [M+H]$^+$.

Production Example 25

Production of 3-[2,5-dihydro-1-(3-methoxyphenyl)-3-methyl-5-oxo-1H-pyrazol-4-yl]-3,5,6,7-tetrahydro-6,6-dimethyl-1-phenyl-3-trifluoromethyl-1H-indole-2,4-dione The title compound was obtained as in Production Example 1 but using as the starting material 2-[1,5-dihydro-1-(3-methoxyphenyl)-3-methyl-5-oxo-4H-pyrazol-4-ylidene]-3,3,3-trifluoro-propanoic acid methyl ester.

$^1$HNMR (400 MHz, CDCl$_3$, δ ppm): 1.06 (3H, s), 1.12 (3H, s), 2.13 (1H, d, J=9.8 Hz), 2.16 (1H, d, J=12.2 Hz), 2.29-2.44 (2H, m), 2.50 (3H, s), 3.81 (3H, s), 7.37-7.45 (4H, m), 7.49-7.58 (5H, m).

ESI-MS (m/e): 526 [M+H]$^+$.

Production Example 26

Production of 3-[2,5-dihydro-1-(4-methoxyphenyl)-3-methyl-5-oxo-1H-pyrazol-4-yl]-3,5,6,7-tetrahydro-6,6-dimethyl-1-phenyl-3-trifluoromethyl-1H-indole-2,4-dione The title compound was obtained as in Production Example 1 but using as the starting material 2-[1,5-dihydro-3-methyl-1-(4-methoxyphenyl)-5-oxo-4H-pyrazol-4-ylidene]-3,3,3-trifluoro-propanoic acid methyl ester.

$^1$HNMR (400 MHz, CDCl$_3$, δ ppm): 1.05 (3H, s), 1.10 (3H, s), 2.08-2.17 (2H, m), 2.23-2.45 (2H, m), 2.47 (3H, s), 3.79 (3H, s), 6.82 (1H, d, J=9.3 Hz), 6.87 (1H, d, J=7.3 Hz), 7.31-7.66 (7H, m).

ESI-MS (m/e): 526 [M+H]$^+$.

Production Example 27

Production of 3-(2,5-dihydro-3-methyl-5-oxo-1-phenyl-1H-pyrazol-4-yl)-3,5,6,7-tetrahydro-6-methyl-1-phenyl-3-trifluoromethyl-1H-indole-2,4-dione The title compound was obtained as in Production Example 1 but using as the starting material 5-methyl-3-phenylamino-2-cyclohexen-1-one.

$^1$HNMR (400 MHz, CDCl$_3$, δ ppm): 0.99-1.05 (3H, m), 1.98-2.51 (8H, m), 7.00-7.10 (1H, m), 7.17-7.31 (4H, m), 7.46-7.56 (3H, m), 7.63 (2H, t, J=7.8 Hz).

ESI-MS (m/e): 482 [M+H]$^+$.

Production Example 28

Production of 3'-(2,5-dihydro-3-methyl-5-oxo-1-phenyl-1H-pyrazol-4-yl)-1'-phenyl-3'-trifluoromethyl-3',7'-dihydrospiro[cyclobutane-1,6'-indole]-2',4'(1'H,5'H)-dione The title compound was obtained as in Production Example 1 but using as the starting material 8-anilino-spiro[3.5]nona-7-en-6-one.

$^1$HNMR (400 MHz, CDCl$_3$, δ ppm): 1.86-1.95 (2H, m), 2.18-2.24 (3H, m), 2.39-2.64 (4H, m), 3.35-3.49 (2H, m), 3.70-3.83 (2H, m), 7.11-7.18 (1H, m), 7.27-7.37 (4H, m), 7.47-7.63 (5H, m).

ESI-MS (m/e): 508 [M+H]$^+$.

Production Example 29

Production of 3-[2,5-dihydro-3-methyl-5-oxo-1-(4-trifluoromethylphenyl)-1H-pyrazol-4-yl]-3,5,6,7-tetrahydro-6,6-dimethyl-1-phenyl-3-trifluoromethyl-1H-indole-2,4-dione The title compound was obtained as in Production Example 1 but using as the starting material 2-[1,5-dihydro-3-methyl-5-oxo-1-(4-trifluoromethylphenyl)-4H-pyrazol-4-ylidene]-3,3,3-trifluoro-propanoic acid methyl ester.

$^1$HNMR (400 MHz, CDCl$_3$, δ ppm): 1.06 (3H, s), 1.12 (3H, s), 2.07-2.49 (4H, m), 2.52 (3H, s), 7.29-7.50 (2H, m), 7.47-7.67 (6H, m), 7.98 (1H, d, J=8.8 Hz).

ESI-MS (m/e): 564 [M+H]$^+$.

Production Example 30

Production of 3-[1-(4-fluorophenyl)-2,5-dihydro-3-methyl-5-oxo-1H-pyrazol-4-yl]-3,5,6,7-tetrahydro-6,6-dimethyl-1-phenyl-3-trifluoromethyl-1H-indole-2,4-dione The title compound was obtained as in Production Example 1 but using as the starting material 2-[1-(4-fluoromethylphenyl)-1,5-dihydro-3-methyl-5-oxo-4H-pyrazol-4-ylidene]-3,3,3-trifluoro-propanoic acid methyl ester.

$^1$HNMR (400 MHz, CDCl$_3$, δ ppm): 1.06 (3H, s), 1.12 (3H, s), 2.07-2.47 (4H, m), 2.49 (3H, s), 6.99-7.10 (2H, m), 7.29-7.35 (1H, m), 7.41 (1H, d, J=6.8 Hz), 7.48-7.58 (4H, m), 7.73-7.78 (1H, m,).

ESI-MS (m/e): 514 [M+H]$^+$.

Production Example 31

Production of 3-[1-(4-cyanophenyl)-2,5-dihydro-3-methyl-5-oxo-1H-pyrazol-4-yl]-3,5,6,7-tetrahydro-6,6-dimethyl-1-phenyl-3-trifluoromethyl-1H-indole-2,4-dione The title compound was obtained as in Production Example 1 but using as the starting material 2-[1-(4-cyanophenyl)-1,5-dihydro-3-methyl-5-oxo-4H-pyrazol-4-ylidene]-3,3,3-trifluoro-propanoic acid methyl ester.

$^1$HNMR (400 MHz, CDCl$_3$, δ ppm): 1.04 (3H, s), 1.09 (3H, s), 2.01-2.56 (4H, m), 2.51 (3H, s), 7.25-7.34 (2H, m), 7.38-7.45 (1H, m), 7.47-7.66 (5H, m), 7.80-7.92 (1H, m).

ESI-MS (m/e): 521 [M+H]$^+$.

Production Example 32

Production of 3-[2,5-dihydro-1-(4-isopropylphenyl)-3-methyl-5-oxo-1H-pyrazol-4-yl]-3,5,6,7-tetrahydro-6,6-dimethyl-1-phenyl-3-trifluoromethyl-1H-indole-2,4-dione The title compound was obtained as in Production Example 1 but using as the starting material 2-[1,5-dihydro-1-(4-isopropylphenyl)-3-methyl-5-oxo-4H-pyrazol-4-ylidene]-3,3,3-trifluoro-propanoic acid methyl ester.

$^1$HNMR (400 MHz, CDCl$_3$, δ ppm): 1.05 (3H, s), 1.11 (3H, s), 1.21 (3H, s), 1.23 (3H, s), 2.08-2.45 (4H, m), 2.49 (3H, s), 2.83-2.92 (1H, m), 7.16-7.25 (3H, m), 7.35-7.57 (5H, m), 7.64 (1H, d, J=8.3 Hz).

ESI-MS (m/e): 538 [M+H]$^+$.

Production Example 33

Production of 3-[2,5-dihydro-3-methyl-1-(4-methylphenyl)-5-oxo-1H-pyrazol-4-yl]-3,5,6,7-tetrahydro-6,6-dimethyl-1-phenyl-3-trifluoromethyl-1H-indole-2,4-dione The title compound was obtained as in Production Example 1 but using as the starting material 2-[1,5-dihydro-3-methyl-1-(4-methylphenyl)-5-oxo-4H-pyrazol-4-ylidene]-3,3,3-trifluoro-propanoic acid methyl ester.

$^1$HNMR (400 MHz, CDCl$_3$, δ ppm): 1.04 (3H, s), 1.11 (3H, s), 2.07-2.42 (7H, m), 2.48 (3H, s), 7.14 (2H, d, J=8.3 Hz), 7.31-7.57 (6H, m), 7.62 (1H, d, J=8.8 Hz).

ESI-MS (m/e): 510 [M+H]$^+$.

Production Example 34

Production of 3-[1-(4-aminosulfonylphenyl)-2,5-dihydro-5-oxo-3-trifluoromethyl-1H-pyrazol-4-yl]-3,5,6,7-tetrahydro-6,6-dimethyl-1-phenyl-3-trifluoromethyl-1H-indole-2,4-dione The title compound was obtained as in Production Example 1 but using as the starting material 2-[1,5-dihydro-3-methyl-5-oxo-1-(4-sulfoamidophenyl)-4H-pyrazol-4-ylidene]-3,3,3-trifluoro-propanoic acid methyl ester.

$^1$HNMR (400 MHz, CDCl$_3$, δ ppm): 1.10 (6H, s), 1.98-2.76 (7H, m), 7.14 (1H, br), 7.37-7.64 (8H, m).

ESI-MS (m/e): 575 [M+H]$^+$.

Production Example 35

Production of 3-[1-(4-tert-butylphenyl)-2,5-dihydro-3-methyl-5-oxo-1H-pyrazol-4-yl]-3,5,6,7-tetrahydro-6,6-dimethyl-1-phenyl-3-trifluoromethyl-1H-indole-2,4-dione The title compound was obtained as in Production Example 1 but using as the starting material 2-[1-(4-tert-butylphenyl)-1,5-dihydro-3-methyl-5-oxo-4H-pyrazol-4-ylidene]-3,3,3-trifluoro-propanoic acid methyl ester.

$^1$HNMR (400 MHz, CDCl$_3$, δ ppm): 1.05 (3H, s), 1.10 (3H, s), 1.29 (9H, s), 2.09-2.53 (7H, m), 7.11-7.22 (2H, m), 7.23-7.69 (9H, m).

ESI-MS (m/e): 552 [M+H]$^+$.

Production Example 36

Production of 3-[2,5-dihydro-3-methyl-5-oxo-1-(4-trifluoromethoxyphenyl)-1H-pyrazol-4-yl]-3,5,6,7-tetrahydro-6,6-dimethyl-1-phenyl-3-trifluoromethyl-1H-indole-2,4-dione The title compound was obtained as in Production Example 1 but using as the starting material 2-[1,5-dihydro-3-methyl-5-oxo-1-(4-trifluoromethoxyphenyl)-4H-pyrazol-4-ylidene]-3,3,3-trifluoro-propanoic acid methyl ester.

$^1$HNMR (400 MHz, CDCl$_3$, δ ppm): 1.05 (3H, s), 1.10 (3H, s), 2.05-2.52 (7H, m), 7.11-7.22 (2H, m), 7.29-7.43 (2H, m), 7.47-7.62 (4H, m), 7.85 (1H, d, J=9.2 Hz).

ESI-MS (m/e): 580 [M+H]$^+$.

Production Example 37

Production of 3-[2,5-dihydro-3-methyl-1-(3,5-dimethylphenyl)-5-oxo-1H-pyrazol-4-yl]-3,5,6,7-tetrahydro-6,6-dimethyl-1-phenyl-3-trifluoromethyl-1H-indole-2,4-dione The title compound was obtained as in Production Example 1 but using as the starting material 2-[1,5-dihydro-3-methyl-1-(3,5-dimethylphenyl)-5-oxo-4H-pyrazol-4-ylidene]-3,3,3-trifluoro-propanoic acid methyl ester.

$^1$HNMR (400 MHz, CDCl$_3$, δ ppm): 1.06 (3H, s), 1.10 (3H, s), 2.12-2.52 (10H, m), 6.80 (1H, s), 7.18 (1H, s), 7.33-7.61 (6H, m).

ESI-MS (m/e): 524 [M+H]$^+$.

Production Example 38

Production of 3-[1-(4-cyclohexylphenyl)-2,5-dihydro-3-methyl-5-oxo-1H-pyrazol-4-yl]-3,5,6,7-tetrahydro-6,6-dimethyl-1-phenyl-3-trifluoromethyl-1H-indole-2,4-dione The title compound was obtained as in Production Example 1 but using as the starting material 2-[1-(4-cyclohexylphenyl)-1,5-dihydro-3-methyl-5-oxo-4H-pyrazol-4-ylidene]-3,3,3-trifluoro-propanoic acid methyl ester.

$^1$HNMR (400 MHz, CDCl$_3$, δ ppm): 1.05 (3H, s), 1.11 (3H, s), 1.30-1.45 (5H, m), 1.68-1.91 (6H, m), 2.08-2.52 (7H, m), 7.15-7.27 (3H, m), 7.36-7.66 (6H, m).

ESI-MS (m/e): 578 [M+H]$^+$.

Production Example 39

Production of 3-[1-(4-benzylphenyl)-2,5-dihydro-3-methyl-5-oxo-1H-pyrazol-4-yl]-3,5,6,7-tetrahydro-6,6-dimethyl-1-phenyl-3-trifluoromethyl-1H-indole-2,4-dione The title compound was obtained as in Production Example 1 but using as the starting material 2-[1-(4-benzylphenyl)-1,5-dihydro-3-methyl-5-oxo-4H-pyrazol-4-ylidene]-3,3,3-trifluoro-propanoic acid methyl ester.

$^1$HNMR (400 MHz, CDCl$_3$, δ ppm): 1.06 (3H, s), 1.12 (3H, s), 2.09-2.19 (1H, m), 2.25-2.51 (6H, m), 3.93-4.00 (2H, m), 7.11-7.43 (10H, m), 7.45-7.60 (4H, m).

ESI-MS (m/e): 586 [M+H]$^+$.

Production Example 40

Production of 3-[2,5-dihydro-1-(4-isopropoxyphenyl)-3-methyl-5-oxo-1H-pyrazol-4-yl]-3,5,6,7-tetrahydro-6,6-dimethyl-1-phenyl-3-trifluoromethyl-1H-indole-2,4-dione The title compound was obtained as in Production Example 1 but using as the starting material 2-[1,5-dihydro-1-(4-isopropoxyphenyl)-3-methyl-5-oxo-4H-pyrazol-4-ylidene]-3,3,3-trifluoro-propanoic acid methyl ester.

$^1$HNMR (400 MHz, CDCl$_3$, δ ppm): 1.17 (3H, br), 1.31 (6H, d, J=5.9 Hz), 2.09-2.50 (7H, m), 4.43-4.61 (1H, m), 6.79-6.95 (2H, m), 7.32-7.65 (5H, m).

ESI-MS (m/e): 554 [M+H]$^+$.

Production Example 41

Production of 3-[2,5-dihydro-3-methyl-5-oxo-1-(4-phenoxyphenyl)-1H-pyrazol-4-yl]-3,5,6,7-tetrahydro-6,6-dimethyl-1-phenyl-3-trifluoromethyl-1H-indole-2,4-dione The title compound was obtained as in Production Example 1 but using as the starting material 2-[1,5-dihydro-3-methyl-5-oxo-1-(4-phenoxyphenyl)-4H-pyrazol-4-ylidene]-3,3,3-trifluoro-propanoic acid methyl ester.

$^1$HNMR (400 MHz, CDCl$_3$, δ ppm): 1.07 (3H, s), 1.12 (3H, s), 2.09-2.53 (7H, m), 6.94-7.13 (7H, m), 7.28-7.43 (4H, m), 7.46-7.59 (3H, m).

ESI-MS (m/e): 588 [M+H]$^+$.

Production Example 42

Production of 3-[2,5-dihydro-3-methyl-5-oxo-1-(biphenyl-4-yl)-1H-pyrazol-4-yl]-3,5,6,7-tetrahydro-6,6-dimethyl-1-phenyl-3-trifluoromethyl-1H-indole-2,4-dione The title compound was obtained as in Production Example 1 but using as the starting material 2-[1,5-dihydro-3-methyl-5-oxo-1-(biphenyl-4-yl)-4H-pyrazol-4-ylidene]-3,3,3-trifluoro-propanoic acid methyl ester.

$^1$HNMR (400 MHz, CDCl$_3$, δ ppm): 1.05 (3H, s), 1.11 (3H, s), 2.10-2.53 (7H, m), 7.31-7.38 (2H, m), 7.40-7.47 (4H, m), 7.53-7.62 (8H, m).

ESI-MS (m/e): 572 [M+H]$^+$.

Production Example 43

Production of 3-[1-(3,5-dichlorophenyl)-2,5-dihydro-3-methyl-5-oxo-1H-pyrazol-4-yl]-3,5,6,7-tetrahydro-6,6-dimethyl-1-phenyl-3-trifluoromethyl-1H-indole-2,4-dione The title compound was obtained as in Production Example 1 but using as the starting material 2-[(3,5-dichlorophenyl)-1,5-dihydro-3-methyl-5-oxo-1-4H-pyrazol-4-ylidene]-3,3,3-trifluoro-propanoic acid methyl ester.

$^1$HNMR (400 MHz, CDCl$_3$, δ ppm): 1.07 (3H, s), 1.11 (3H, s), 2.09-2.45 (7H, m), 7.12-7.17 (1H, m), 7.28-7.34 (1H, m), 7.38-7.44 (1H, m), 7.49-7.60 (4H, m), 7.83 (1H, d, J=2.0 Hz).

ESI-MS (m/e): 565 [M+H]$^+$.

Production Example 44

Production of 3-[2,5-dihydro-3-methyl-(4-methylsulfonylphenyl)-5-oxo-1H-pyrazol-4-yl]-3,5,6,7-tetrahydro-6,6-dimethyl-1-phenyl-3-trifluoromethyl-1H-indole-2,4-dione The title compound was obtained as in Production Example 1 but using as the starting material 2-[1,5-dihydro-3-methyl-1-(4-methylsulfonylphenyl)-5-oxo-4H-pyrazol-4-ylidene]-3,3,3-trifluoro-propanoic acid methyl ester.

$^1$HNMR (400 MHz, CDCl$_3$, δ ppm): 1.06 (3H, s), 1.12 (3H, s), 2.18-2.54 (7H, m), 3.04 (3H, s), 7.28-7.38 (5H, m), 7.28-7.35 (1H, m), 7.41 (1H, d, J=8.0 Hz), 7.49-7.60 (3H, m), 7.85 (2H, br), 7.92 (1H, d, J=8.8 Hz), 8.09 (1H, d, J=8.8 Hz).

ESI-MS (m/e): 574 [M+H]$^+$.

Referential Example 1

Production of 3-(1-cyclobutylamino)-5,5-dimethyl-2-cyclohexen-1-one

To a toluene solution (30 ml) of 1,3-cyclohexanedione (1.40 g, 10.0 mmol), cyclopentylamine (782 mg, 11.0 mmol) and boron trifluoride diethyl ether complex (1.56 g, 11.0 mmol) were added at room temperature and the mixture was stirred under reflux for 14 hours. After concentrating the liquid reaction mixture under reduced pressure, a 5% aqueous sodium hydroxide solution was added. The liquid reaction mixture was extracted with ethyl acetate and concentrated under reduced pressure. The residue was purified by silica gel flash column chromatography. Thus, the title compound was obtained as a yellow oily product (1.64 g). $^1$HNMR (400

MHz, CDCl₃, δ ppm): 1.06 (6H, s), 1.77-1.96 (4H, m), 2.17 (4H, d, J=7.3 Hz), 2.36-2.46 (2H, m), 3.85-3.95 (1H, m).

Referential Example 2

Production of 3-(1-cyclopentylamino)-5,5-dimethyl-2-cyclohexen-1-one

The title compound was obtained as in Referential Example 1 but using as the starting material cyclopentylamine.

¹HNMR (400 MHz, CDCl₃, δ ppm): 0.77-0.90 (4H, m), 1.11 (3H, s), 1.14 (3H, s), 1.21-1.35 (2H, m), 1.50-1.64 (2H, m), 2.20 (2H, m), 2.49 (2H, br)

Referential Example 3

Production of 3-ethyl-α-hydroxy-2,5-dihydro-5-oxo-1-phenyl-α-trifluoromethyl-1H-pyrazole-4-acetic acid methyl ester To a chloroform solution (5 ml) of 3-ethyl-1-phenyl-5-pyrazolone (94 mg, 0.5 mmol), methyl trifluoropyruvate (78 mg, 0.5 mmol) was added at room temperature and the mixture was stirred at 80° C. for 2 hours. After removing the solvent under reduced pressure, the title compound was obtained as a colorless solid (172 mg).

¹HNMR (400 MHz, CDCl₃, δ ppm): 1.25 (3H, t, J=7.6 Hz), 2.71 (2H, q, J=7.8 Hz) 15.4, 3.98 (3H, s), 4.05 (1H, s), 7.14-7.30 (2H, m), 7.36-7.45 (2H, m), 7.63 (1H, br), 7.84 (1H, d, J=8.8 Hz).

ESI-MS (m/e): 345 [M+H]⁺.

Referential Example 4

Production of 2-(3-ethyl-1,5-dihydro-5-oxo-1-phenyl-4H-pyrazol-4-ylidene)-3,3,3-trifluoro-propanoic acid methyl ester To a toluene solution (5 ml) of 3-ethyl-α-hydroxy-2,5-dihydro-5-oxo-1-phenyl-α-trifluoromethyl-1H-pyrazole-4-acetic acid methyl ester (172 mg, 0.5 mmol), thionyl chloride (0.365 ml, 5.0 mmol) was added and the mixture was stirred under reflux for 3 hours. After concentrating the liquid reaction mixture under reduced pressure, the title compound was obtained as a reddish brown solid (163 mg).

¹HNMR (400 MHz, CDCl₃, δ ppm): 1.36 (3H, t, J=7.3 Hz), 2.75 (2H, dd, J=14.4, 7.1 Hz), 4.01 (3H, s), 7.16-7.22 (1H, m), 7.41 (2H, t, J=8.8 Hz), 7.84 (2H, d, J=7.8 Hz).

ESI-MS (m/e): 327 [M+H]⁺.

Referential Example 5

Production of 3-cyclopropyl-α-hydroxy-2,5-dihydro-5-oxo-1-phenyl-α-trifluoromethyl-1H-pyrazole-4-acetic acid methyl ester To a chloroform solution (5 ml) of 3-cyclopropyl-1-phenyl-5-pyrazolone (100 mg, 0.5 mmol), methyl trifluoropyruvate (78 mg, 0.5 mmol) was added at room temperature and the mixture was stirred at 80° C. for 2 hours. After removing the solvent under reduced pressure, the title compound was obtained as a colorless solid (178 mg).

¹HNMR (400 MHz, CDCl₃, δ ppm): 0.73-1.27 (4H, m), 1.27-1.81 (1H, m), 3.98 (3H, s), 4.06 (1H, s), 7.14-7.22 (1H, m), 7.33-7.45 (3H, m), 7.63 (1H, br), 7.79 (1H, d, J=8.8 Hz).

ESI-MS (m/e): 357 [M+H]⁺.

Referential Example 6

Production of 2-(3-cyclopropyl-1,5-dihydro-5-oxo-1-phenyl-4H-pyrazol-4-ylidene)-3,3,3-trifluoro-propanoic acid methyl ester To a toluene solution (5 ml) of 3-cyclopropyl-α-hydroxy-2,5-dihydro-5-oxo-1-phenyl-α-trifluoromethyl-1H-pyrazole-4-acetic acid methyl ester (178 mg, 0.5 mmol), thionyl chloride (0.365 ml, 5.0 mmol) was added and the mixture was stirred under reflux for 3 hours. After concentrating the liquid reaction mixture under reduced pressure, the title compound was obtained as a reddish brown solid (169 mg).

¹HNMR (400 MHz, CDCl₃, δ ppm): 0.99-1.04 (2H, m), 1.10-1.15 (2H, m),), 1.93-2.01 (1H, m). 4.02 (3H, s), 7.16-7.24 (2H, m), 7.36-7.42 (2H, m), 7.79 (2H, d, J=8.8 Hz).

ESI-MS (m/e): 339 [M+H]⁺.

Referential Example 7

Production of α-hydroxy-2,5-dihydro-5-oxo-1-phenyl-α-trifluoromethyl-3-trifluoromethyl-1H-pyrazole-4-acetic acid methyl ester To a chloroform solution (5 ml) of 1-phenyl-3-trifluoromethyl-5-pyrazolone (114 mg, 0.5 mmol), methyl trifluoropyruvate (78 mg, 0.5 mmol) was added at room temperature and the mixture was stirred at 80° C. for 2 hours. After removing the solvent under reduced pressure, the title compound was obtained as a colorless solid (172 mg).

¹HNMR (400 MHz, CDCl₃, δ ppm): 4.07 (3H, s), 4.31 (1H, s), 7.38 (1H, t, J=7.3 Hz), 7.48 (2H, t, J=7.3 Hz), 7.71 (2H, d, J=8.8 Hz).

ESI-MS (m/e): 385 [M+H]⁺.

Referential Example 8

Production of 2-(1,5-dihydro-3-trifluoromethyl-5-oxo-1-phenyl-4H-pyrazol-4-ylidene)-3,3,3-trifluoropropanoic acid methyl ester To a toluene solution (5 ml) of α-hydroxy-2,5-dihydro-5-oxo-1-phenyl-α-trifluoromethyl-3-trifluoromethyl-1H-pyrazole-4-acetic acid methyl ester (192 mg, 0.5 mmol), thionyl chloride (0.365 ml, 5.0 mmol) was added and the mixture was stirred under reflux for 3 hours. After concentrating the liquid reaction mixture under reduced pressure, the title compound was obtained as a reddish brown solid (183 mg).

¹HNMR (400 MHz, CDCl₃, δ ppm): 4.04 (3H, s), 7.43-7.52 (2H, m), 7.66-7.71 (1H, m), 7.74-7.78 (2H, m).

ESI-MS (m/e): 367 [M+H]⁺.

Referential Example 9

Production of 1-(3-chlorophenyl)-2,5-dihydro-α-hydroxy-3-methyl-5-oxo-α-trifluoromethyl-1H-pyrazole-4-acetic acid methyl ester To a chloroform solution (5 ml) of (3-chlorophenyl)-3-methyl-1-5-pyrazolone (104 mg, 0.5 mmol), methyl trifluoropyruvate (78 mg, 0.5 mmol) was added at room temperature and the mixture was stirred at 80° C. for 2 hours. After removing the solvent under reduced pressure, the title compound was obtained as a colorless solid (182 mg).

¹HNMR (400 MHz, CDCl₃, δ ppm): 2.33 (3H, s), 3.98 (3H, s), 4.01 (1H, s), 7.14-7.30 (2H, m), 7.58-7.66 (1H, m), 7.72-7.80 (1H, m).
ESI-MS (m/e): 365 [M+H]⁺.

Referential Example 10

Production of 2-[1-(3-chlorophenyl)-1,5-dihydro-3-methyl-5-oxo-4H-pyrazol-4-ylidene]-3,3,3-trifluoro-propanoic acid methyl ester To a toluene solution (5 ml) of 1-(3-chlorophenyl)-2,5-dihydro-α-hydroxy-3-methyl-5-oxo-α-trifluoromethyl-1H-pyrazole-4-acetic acid methyl ester (182 mg, 0.5 mmol), thionyl chloride (0.365 ml, 5.0 mmol) was added and the mixture was stirred under reflux for 3 hours. After concentrating the liquid reaction mixture under reduced pressure, the title compound was obtained as a reddish brown solid (173 mg).
¹HNMR (400 MHz, CDCl₃, δ ppm): 2.41 (3H, s), 4.02 (3H, s), 7.17-7.22 (1H, m), 7.33 (1H, t, J=8.3 Hz), 7.75-7.79 (1H, m), 7.90 (1H, t, J=2.0 Hz).
ESI-MS (m/e): 347 [M+H]⁺.

Referential Example 11

Production of 1-(4-chlorophenyl)-2,5-dihydro-α-hydroxy-3-methyl-5-oxo-α-trifluoromethyl-1H-pyrazole-4-acetic acid methyl ester To a chloroform solution (5 ml) of 1-(4-chlorophenyl)-3-methyl-5-pyrazolone (104 mg, 0.5 mmol), methyl trifluoropyruvate (78 mg, 0.5 mmol) was added at room temperature and the mixture was stirred at 80° C. for 2 hours. After removing the solvent under reduced pressure, the title compound was obtained as a colorless solid (182 mg).
¹HNMR (400 MHz, CDCl₃, δ ppm): 2.32 (3H, s), 3.98 (3H, s), 4.01 (1H, s), 7.35-7.41 (2H, m), 7.59-7.65 (2H, m).
ESI-MS (m/e): 365 [M+H]⁺.

Referential Example 12

Production of 2-[1-(4-chlorophenyl)-1,5-dihydro-3-methyl-5-oxo-4H-pyrazol-4-ylidene]-3,3,3-trifluoro-propanoic acid methyl ester To a toluene solution (5 ml) of 1-(4-chlorophenyl)-2,5-dihydro-α-hydroxy-3-methyl-5-oxo-α-trifluoromethyl-1H-pyrazole-4-acetic acid methyl ester (182 mg, 0.5 mmol), thionyl chloride (0.365 ml, 5.0 mmol) was added and the mixture was stirred under reflux for 3 hours. After concentrating the liquid reaction mixture under reduced pressure, the title compound was obtained as a reddish brown solid (173 mg).
¹HNMR (400 MHz, CDCl₃, δ ppm): 2.41 (3H, s), 4.02 (3H, s), 7.36 (2H, d, J=9.3 Hz), 7.79 (2H, d, J=8.8 Hz).
ESI-MS (m/e): 347 [M+H]⁺.

Referential Example 13

Production of 2,5-dihydro-α-hydroxy-1-(2-methoxyphenyl)-3-methyl-5-oxo-α-trifluoromethyl-1H-pyrazole-4-acetic acid methyl ester To a toluene solution (5 ml) of 3-acetyl-2-hydroxy-2-trifluoromethyl-butanedioic acid-4-ethyl-1-methyl ester (143 mg, 0.5 mmol), 2-methoxyphenylhydrazine (78 mg, 0.5 mmol) was added at room temperature and the mixture was stirred at 80° C. for 2 hours. After removing the solvent under reduced pressure, the title compound was obtained as a pale yellow solid (180 mg).
¹HNMR (400 MHz, CDCl₃, δ ppm): 2.36 (3H, s), 3.84 (3H, s), 3.88 (3H, s), 3.99 (1H, s), 7.14-7.21 (2H, m), 7.22-7.29 (2H, m).
ESI-MS (m/e): 361 [M+H]⁺.

Referential Example 14

Production of 2-[1,5-dihydro-1-(2-methoxyphenyl)-3-methyl-5-oxo-4H-pyrazol-4-ylidene]-3,3,3-trifluoro-propanoic acid methyl ester To a toluene solution (5 ml) of 2,5-dihydro-α-hydroxy-1-(2-methoxyphenyl)-3-methyl-5-oxo-α-trifluoromethyl-1H-pyrazole-4-acetic acid methyl ester (180 mg, 0.5 mmol), thionyl chloride (0.365 ml, 5.0 mmol) was added and the mixture was stirred under reflux for 3 hours. After concentrating the liquid reaction mixture under reduced pressure, the title compound was obtained as a reddish brown solid (171 mg).
¹HNMR (400 MHz, CDCl₃, δ ppm): 2.36 (3H, s), 3.92 (3H, s), 3.93 (3H, s), 7.20-7.15 (2H, m), 7.23-7.28 (2H, m).
ESI-MS (m/e): 343 [M+H]⁺.

Referential Example 15

Production of 2,5-dihydro-α-hydroxy-1-(3-methoxyphenyl)-3-methyl-5-oxo-α-trifluoromethyl-1H-pyrazole-4-acetic acid methyl ester To a chloroform solution (5 ml) of 1-(3-methoxyphenyl)-3-methyl-5-pyrazolone (102 mg, 0.5 mmol), methyl trifluoropyruvate (78 mg, 0.5 mmol) was added at room temperature and the mixture was stirred at 80° C. for 2 hours. After removing the solvent under reduced pressure, the title compound was obtained as a pale yellow solid (180 mg).
¹HNMR (400 MHz, CDCl₃, δ ppm): 2.41 (3H, s), 3.98 (3H, s), 4.00 (1H, s), 4.02 (3H, s), 7.14-7.20 (1H, m), 7.23-7.34 (2H, m), 7.41-7.43 (1H, m).
ESI-MS (m/e): 361 [M+H]⁺.

Referential Example 16

Production of 2-[1,5-dihydro-1-(3-methoxyphenyl)-3-methyl-5-oxo-4H-pyrazol-4-ylidene]-3,3,3-trifluoro-propanoic acid methyl ester To a toluene solution (5 ml) of 2,5-dihydro-α-hydroxy-1-(3-methoxyphenyl)-3-methyl-5-oxo-α-trifluoromethyl-1H-pyrazole-4-acetic acid methyl ester (180 mg, 0.5 mmol), thionyl chloride (0.365 ml, 5.0 mmol) was added and the mixture was stirred under reflux for 3 hours. After concentrating the liquid reaction mixture under reduced pressure, the title compound was obtained as a reddish brown solid (171 mg).
¹HNMR (400 MHz, CDCl₃, δ ppm): 2.41 (3H, s), 3.83 (3H, s), 4.02 (3H, s), 7.15-7.20 (1H, m), 7.23-7.33 (2H, m), 7.41-7.44 (1H, m).
ESI-MS (m/e): 343 [M+H]⁺.

Referential Example 17

Production of 2,5-dihydro-α-hydroxy-1-(4-methoxyphenyl)-3-methyl-5-oxo-α-trifluoromethyl-1H-pyrazole-4-acetic acid methyl ester To a chloroform solution (5 ml) of 1-(4-methoxyphenyl)-3-methyl-5-pyrazolone (102 mg, 0.5 mmol), methyl trifluoropyruvate (78 mg, 0.5 mmol) was added at room temperature and the mixture was stirred at 80° C. for 2 hours. After removing the solvent under reduced pressure, the title compound was obtained as a pale yellow solid (180 mg).

$^1$HNMR (400 MHz, CDCl$_3$, δ ppm): 2.26 (3H, s), 3.82 (3H, s), 3.97 (1H, s), 3.98 (3H, s), 6.88-6.95 (1H, m), 7.45 (2H, br)

ESI-MS (m/e): 361 [M+H]$^+$.

Referential Example 18

Production of 2-[1,5-dihydro-(4-methoxyphenyl)-3-methyl-1-5-oxo-4H-pyrazol-4-ylidene]-3,3,3-trifluoro-propanoic acid methyl ester To a toluene solution (5 ml) of 2,5-dihydro-α-hydroxy-1-(4-methoxyphenyl)-3-methyl-5-oxo-α-trifluoromethyl-1H-pyrazole-4-acetic acid methyl ester (180 mg, 0.5 mmol), thionyl chloride (0.365 ml, 5.0 mmol) was added and the mixture was stirred under reflux for 3 hours. After concentrating the liquid reaction mixture under reduced pressure, the title compound was obtained as a reddish brown solid (171 mg).

$^1$HNMR (400 MHz, CDCl$_3$, δ ppm): 2.39 (3H, s), 3.82 (3H, s), 4.00 (3H, s), 6.92 (2H, d, J=9.3 Hz), 7.68 (2H, d, J=9.3 Hz).

ESI-MS (m/e): 343 [M+H]$^+$.

Referential Example 19

Production of 8-anilino-spiro[3,5]non-7-en-6-one

The title compound was obtained as in Referential Example 1 but using as the starting material spiro[3,5]nonan-6,8-dione.

$^1$HNMR (400 MHz, CDCl$_3$, δ ppm): 1.85-1.97 (6H, m), 2.48 (2H, s), 2.57 (2H, s), 5.57 (1H, s), 6.11 (1H, br), 7.14-7.19 (3H, m), 7.31-7.37 (2H, m).

Referential Example 20

Production of 2,5-dihydro-α-hydroxy-3-methyl-5-oxo-α-trifluoromethyl-1-(4-trifluoromethylphenyl)-1H-pyrazole-4-acetic acid methyl ester To a chloroform solution (5 ml) of 3-acetyl-2-hydroxy-2-trifluoromethyl-butanedioic acid-4-ethyl-1-methyl ester (143 mg, 0.5 mmol), 4-trifluorophenylhydrazine (88 mg, 0.5 mmol) was added at room temperature and the mixture was stirred at 80° C. for 2 hours. After removing the solvent under reduced pressure, the title compound was obtained as a pale yellow solid (199 mg).

$^1$HNMR (400 MHz, CDCl$_3$, δ ppm): 2.36 (3H, s), 4.04 (3H, br), 3.97 (3H, s), 4.07 (1H, s), 7.15-7.20 (1H, m), 7.64-7.70 (2H, m).

ESI-MS (m/e): 399 [M+H]$^+$.

Referential Example 21

Production of 2-[1,5-dihydro-3-methyl-5-oxo-1-(4-trifluoromethylphenyl)-4H-pyrazol-4-ylidene]-3,3,3-trifluoro-propanoic acid methyl ester To a toluene solution (5 ml) of 2,5-dihydro-α-hydroxy-3-methyl-5-oxo-α-trifluoromethyl-1-(4-trifluoromethylphenyl)-1H-pyrazole-4-acetic acid methyl ester (180 mg, 0.5 mmol), thionyl chloride (0.365 ml, 5.0 mmol) was added and the mixture was stirred under reflux for 3 hours. After concentrating the liquid reaction mixture under reduced pressure, the title compound was obtained as a reddish brown solid (171 mg).

$^1$HNMR (400 MHz, CDCl$_3$, δ ppm): 2.44 (3H, s), 3.82 (3H, s), 4.02 (1H, s), 4.03 (3H, s), 7.66 (2H, d, J=8.8 Hz), 8.01 (2H, d, J=8.3 Hz).

ESI-MS (m/e): 381 [M+H]$^+$.

Referential Example 22

Production of 1-(4-fluorophenyl)-2,5-dihydro-α-hydroxy-3-methyl-5-oxo-α-trifluoromethyl-1H-pyrazole-4-acetic acid methyl ester To a chloroform solution (5 ml) of 1-(4-fluorophenyl)-3-methyl-5-pyrazolone (96 mg, 0.5 mmol), methyl trifluoropyruvate (78 mg, 0.5 mmol) was added at room temperature and the mixture was stirred at 80° C. for 2 hours. After removing the solvent under reduced pressure, the title compound was obtained as a pale yellow solid (174 mg).

$^1$HNMR (400 MHz, CDCl$_3$, δ ppm): 2.29 (3H, s), 4.00 (3H, br), 4.05 (1H, s), 7.06-7.15 (2H, m), 7.56-7.68 (2H, m).

ESI-MS (m/e): 349 [M+H]$^+$.

Referential Example 23

Production of 2-[1-(4-fluorophenyl)-1,5-dihydro-3-methyl-5-oxo-4H-pyrazol-4-ylidene]-3,3,3-trifluoro-propanoic acid methyl ester To a toluene solution (5 ml) of 1-(4-fluorophenyl)-2,5-dihydro-α-hydroxy-3-methyl-5-oxo-α-trifluoromethyl-1H-pyrazole-4-acetic acid methyl ester (180 mg, 0.5 mmol), thionyl chloride (0.365 ml, 5.0 mmol) was added and the mixture was stirred under reflux for 3 hours. After concentrating the liquid reaction mixture under reduced pressure, the title compound was obtained as a reddish brown solid (171 mg).

$^1$HNMR (400 MHz, CDCl$_3$, δ ppm): 2.41 (3H, m), 4.01 (1H, s), 4.03 (3H, s), 7.07-7.13 (2H, m), 7.76-7.82 (2H, m).

ESI-MS (m/e): 331 [M+H]$^+$.

Referential Example 24

Production of 1-(4-cyanophenyl)-2,5-dihydro-α-hydroxy-3-methyl-5-oxo-α-trifluoromethyl-1H-pyrazole-4-acetic acid methyl ester To a chloroform solution (5 ml) of 1-(4-cyanophenyl)-3-methyl-5-pyrazolone (100 mg, 0.5 mmol), methyl trifluoropyruvate (78 mg, 0.5 mmol) was added at room temperature and the mixture was stirred at 80° C. for 2 hours. After removing the solvent under reduced pressure, the title compound was obtained as a pale yellow solid (174 mg).

$^1$HNMR (400 MHz, CDCl$_3$, δ ppm): 2.33 (3H, s), 3.98 (3H, s), 4.02 (1H, s), 7.70 (2H, d, J=8.3 Hz), 7.92-7.99 (2H, m).

ESI-MS (m/e): 356 [M+H]$^+$.

Referential Example 25

Production of 2-[1-(4-cyanophenyl)-1,5-dihydro-3-methyl-5-oxo-4H-pyrazol-4-ylidene]-3,3,3-trifluoro-propanoic acid methyl ester To a toluene solution (5 ml) of 1-(4-cyanophenyl)-2,5-dihydro-α-hydroxy-3-methyl-5-oxo-α-trifluoromethyl-1H-pyrazole-4-acetic acid methyl ester (180 mg, 0.5 mmol), thionyl chloride (0.365 ml, 5.0 mmol) was added and the mixture was stirred under reflux for 3 hours. After concentrating the liquid reaction mixture under reduced pressure, the title compound was obtained as a reddish brown solid (171 mg).
$^1$HNMR (400 MHz, CDCl$_3$, δ ppm): 2.44 (3H, m), 4.03 (3H, s), 7.70 (2H, d, J=9.3 Hz), 7.76-7.82 (2H, d, J=8.8 Hz).
ESI-MS (m/e): 338 [M+H]$^+$.

Referential Example 26

Production of 2,5-dihydro-α-hydroxy-1-(4-isopropylphenyl)-3-methyl-5-oxo-α-trifluoromethyl-1H-pyrazole-4-acetic acid methyl ester To a chloroform solution (5 ml) of 1-(4-isopropylphenyl)-3-methyl-5-pyrazolone (108 mg, 0.5 mmol), methyl trifluoropyruvate (78 mg, 0.5 mmol) was added at room temperature and the mixture was stirred at 80° C. for 2 hours. After removing the solvent under reduced pressure, the title compound was obtained as a pale yellow solid (186 mg).
$^1$HNMR (400 MHz, CDCl$_3$, δ ppm): 1.25 (6H, dd, J=2.0, 6.8 Hz), 2.36 (3H, s), 2.86-2.97 (1H, m), 3.98 (3H, s), 4.00 (1H, s), 7.14-7.20 (2H, m), 7.22-7.30 (2H, m).
ESI-MS (m/e): 373 [M+H]$^+$.

Referential Example 27

Production of 2-[1,5-dihydro-1-(4-isopropylphenyl)-3-methyl-5-oxo-4H-pyrazol-4-ylidene]-3,3,3-trifluoro-propanoic acid methyl ester To a toluene solution (5 ml) of 2,5-dihydro-α-hydroxy-1-(4-isopropylphenyl)-3-methyl-5-oxo-α-trifluoromethyl-1H-pyrazole-4-acetic acid methyl ester (180 mg, 0.5 mmol), thionyl chloride (0.365 ml, 5.0 mmol) was added and the mixture was stirred under reflux for 3 hours. After concentrating the liquid reaction mixture under reduced pressure, the title compound was obtained as a reddish brown solid (171 mg).
$^1$HNMR (400 MHz, CDCl$_3$, δ ppm): 1.24 (6H, d, J=6.8 Hz), 2.40 (3H, m), 2.86-2.96 (1H, m), 2.40 (3H, m), 3.99 (1H, s), 4.00 (3H, s), 7.23-7.26 (2H, m), 7.68 (2H, d, J=8.8 Hz).
ESI-MS (m/e): 355 [M+H]$^+$.

Referential Example 28

Production of 2,5-dihydro-α-hydroxy-3-methyl-1-(4-methylphenyl)-5-oxo-α-trifluoromethyl-1H-pyrazole-4-acetic acid methyl ester To a chloroform solution (5 ml) of 3-methyl-1-(4-methylphenyl)-5-pyrazolone (94 mg, 0.5 mmol), methyl trifluoropyruvate (78 mg, 0.5 mmol) was added at room temperature and the mixture was stirred at 80° C. for 2 hours. After removing the solvent under reduced pressure, the title compound was obtained as a pale yellow solid (172 mg).
$^1$HNMR (400 MHz, CDCl$_3$, δ ppm): 2.27 (3H, s), 2.36 (3H, s), 3.97 (3H, s), 4.05 (1H, s), 7.20 (2H, d, J=8.8 Hz), 7.67 (2H, d, J=8.8 Hz).
ESI-MS (m/e): 345 [M+H]$^+$.

Referential Example 29

Production of 2-[1,5-dihydro-3-methyl-1-(4-methylphenyl)-5-oxo-4H-pyrazol-4-ylidene]-3,333-trifluoro-propanoic acid methyl ester To a toluene solution (5 ml) of 2,5-dihydro-α-hydroxy-3-methyl-1-(4-methylphenyl)-5-oxo-α-trifluoromethyl-1H-pyrazole-4-acetic acid methyl ester (172 mg, 0.5 mmol), thionyl chloride (0.365 ml, 5.0 mmol) was added and the mixture was stirred under reflux for 3 hours. After concentrating the liquid reaction mixture under reduced pressure, the title compound was obtained as a reddish brown solid (163 mg).
$^1$HNMR (400 MHz, CDCl$_3$, δ ppm): 2.35 (3H, s), 2.40 (3H, m), 4.00 (3H, s), 7.20 (2H, d, J=8.3 Hz), 7.70 (2H, d, J=8.8 Hz).
ESI-MS (m/e): 327 [M+H]$^+$.

Referential Example 30

Production of 2,5-dihydro-α-hydroxy-3-methyl-5-oxo-1-(4-sulfoamidophenyl)-α-trifluoromethyl-1H-pyrazole-4-acetic acid methyl ester To a chloroform solution (5 ml) of 3-methyl-1-(4-sulfoamidophenyl)-5-pyrazolone (205 mg, 0.5 mmol), methyl trifluoropyruvate (78 mg, 0.5 mmol) was added at room temperature and the mixture was stirred at 80° C. for 2 hours. After removing the solvent under reduced pressure, the title compound was obtained as a pale yellow solid (196 mg).
$^1$HNMR (400 MHz, DMSO-d$_6$, δ ppm): 2.31 (3H, s), 3.81 (3H, s), 7.85-7.94 (4H, m).
ESI-MS (m/e): 410 [M+H]$^+$.

Referential Example 31

Production of 2-[1,5-dihydro-3-methyl-5-oxo-1-(4-sulfoamidophenyl)-4H-pyrazol-4-ylidene]-3,3,3-trifluoro-propanoic acid methyl ester To a toluene solution (5 ml) of 2,5-dihydro-α-hydroxy-3-methyl-5-oxo-1-(4-sulfoamidophenyl)-α-trifluoromethyl-1H-pyrazole-4-acetic acid methyl ester (172 mg, 0.5 mmol), thionyl chloride (0.365 ml, 5.0 mmol) was added and the mixture was stirred under reflux for 3 hours. After concentrating the liquid reaction mixture under reduced pressure, the title compound was obtained as a reddish brown solid (163 mg).
$^1$HNMR (400 MHz, CDCl$_3$, δ ppm): 2.45 (3H, m), 4.03 (3H, s), 7.15-7.20 (4H, m).
ESI-MS (m/e): 392 [M+H]$^+$.

Referential Example 32

Production of 1-(4-tert-butylphenyl)-2,5-dihydro-α-hydroxy-3-methyl-5-oxo-α-trifluoromethyl-1H-pyrazole-4-acetic acid methyl ester The title compound was obtained as in Production Example 1 but using as the starting material 4-tert-butylphenylhydrazine.
$^1$HNMR (400 MHz, CDCl$_3$, δ ppm): 1.33 (9H, s), 2.30 (3H, s), 3.99 (3H, br), 4.05 (1H, s), 7.43 (2H, d, J=8.8 Hz), 7.53 (2H, d, J=7.3 Hz).
ESI-MS (m/e): 387 [M+H]$^+$.

Referential Example 33

Production of 2-[1-(4-tert-butylphenyl)-1,5-dihydro-3-methyl-5-oxo-4H-pyrazol-4-ylidene]-3,3,3-trifluoro-propanoic acid methyl ester The title compound was obtained as in Production Example 1 but using as the starting material 1-(4-tert-butylphenyl)-2,5-dihydro-α-hydroxy-3-methyl-5-oxo-α-trifluoromethyl-1H-pyrazole-4-acetic acid methyl ester.
¹HNMR (400 MHz, CDCl₃, δ ppm): 1.32 (9H, s), 2.42 (3H, s), 4.01 (3H, s), 7.41 (2H, d, J=8.8 Hz), 7.68 (2H, d, J=8.8 Hz).
ESI-MS (m/e): 369 [M+H]

Referential Example 34

Production of 2,5-dihydro-α-hydroxy-3-methyl-5-oxo-1-(4-trifluoromethoxyphenyl)-α-trifluoromethyl-1H-pyrazole-4-acetic acid methyl ester The title compound was obtained as in Production Example 1 but using as the starting material 4-trifluoromethoxyphenylhydrazine.
¹HNMR (400 MHz, CDCl₃, δ ppm): 2.31 (3H, s), 4.03 (3H, br), 4.06 (1H, s), 7.15-7.29 (2H, m), 7.74 (2H, d, J=8.3 Hz).
ESI-MS (m/e): 415 [M+H]⁺.

Referential Example 35

Production of 2-[1,5-dihydro-3-methyl-5-oxo-1-(4-trifluoromethoxyphenyl)-4H-pyrazol-4-ylidene]-3,3,3-trifluoro-propanoic acid methyl ester The title compound was obtained as in Production Example 1 but using as the starting material 2,5-dihydro-α-hydroxy-3-methyl-5-oxo-1-(4-trifluoromethoxyphenyl)-α-trifluoromethyl-1H-pyrazole-4-acetic acid methyl ester.
¹HNMR (400 MHz, CDCl₃, δ ppm): 2.42 (3H, s), 4.02 (3H, s), 7.26 (2H, d, J=8.3 Hz), 7.88 (2H, d, J=9.3 Hz).
ESI-MS (m/e): 397 [M+H]

Referential Example 36

Production of 2,5-dihydro-α-hydroxy-3-methyl-1-(3,5-dimethylphenyl)-5-oxo-α-trifluoromethyl-1H-pyrazole-4-acetic acid methyl ester The title compound was obtained as in Production Example 1 but using as the starting material 3,5-dimethylphenylhydrazine.
¹HNMR (400 MHz, CDCl₃, δ ppm): 2.29 (3H, s), 2.34 (6H, s), 4.02 (3H, s), 4.05 (1H, s), 6.92 (1H, s), 7.14-7.20 (1H, m), 7.46 (1H, d, J=7.8 Hz).
ESI-MS (m/e): 359 [M+H]⁺.

Referential Example 37

Production of 2-[1,5-dihydro-3-methyl-1-(3,5-dimethylphenyl)-5-oxo-4H-pyrazol-4-ylidene]-3,3,3-trifluoro-propanoic acid methyl ester The title compound was obtained as in Production Example 1 but using as the starting material 2,5-dihydro-α-hydroxy-3-methyl-1-(3,5-dimethylphenyl)-5-oxo-α-trifluoromethyl-1H-pyrazole-4-acetic acid methyl ester.
¹HNMR (400 MHz, CDCl₃, δ ppm): 2.34 (6H, s), 2.36 (3H, s), 4.02 (3H, s), 7.18 (2H, s), 7.43 (1H, s).
ESI-MS (m/e): 341 [M+H]

Referential Example 38

Production of 1-(4-cyclohexylphenyl)-2,5-dihydro-α-hydroxy-3-methyl-5-oxo-α-trifluoromethyl-1H-pyrazole-4-acetic acid methyl ester The title compound was obtained as in Production Example 1 but using as the starting material 4-cyclohexylphenylhydrazine.
¹HNMR (400 MHz, CDCl₃, δ ppm): 1.32-1.46 (5H, m), 1.77-1.92 (5H, m), 2.28 (3H, s), 2.36 (1H, s), 2.47-2.55 (1H, m), 3.97 (3H, s), 4.04 (1H, s), 6.91 (2H, d, J=9.3 Hz), 7.14-7.20 (1H, m), 7.46 (1H, d, J=7.8 Hz).
ESI-MS (m/e): 413 [M+H]⁺.

Referential Example 39

Production of 2-[1-(4-cyclohexylphenyl)-1,5-dihydro-3-methyl-5-oxo-4H-pyrazol-4-ylidene]-3,3,3-trifluoro-propanoic acid methyl ester The title compound was obtained as in Production Example 1 but using as the starting material 1-(4-cyclohexylphenyl)-2,5-dihydro-α-hydroxy-3-methyl-5-oxo-α-trifluoromethyl-1H-pyrazole-4-acetic acid methyl ester.
¹HNMR (400 MHz, CDCl₃, δ ppm): 1.32-1.46 (5H, m), 1.77-1.92 (5H, m), 2.39 (3H, s), 2.47-2.55 (1H, m), 4.00 (3H, 1), 7.15-7.28 (3H, m), 7.67 (1H, d, J=8.3 Hz).
ESI-MS (m/e): 395 [M+H]

Referential Example 40

Production of 1-(4-benzylphenyl)-2,5-dihydro-α-hydroxy-3-methyl-5-oxo-α-trifluoromethyl-1H-pyrazole-4-acetic acid methyl ester The title compound was obtained as in Production Example 1 but using as the starting material 4-benzylphenylhydrazine.
¹HNMR (400 MHz, CDCl₃, δ ppm): 2.29 (3H, s), 3.99 (2H, s), 4.00 (3H, s), 4.51-4.58 (1H, m), 6.91 (2H, d, J=9.3 Hz), 7.14-7.20 (1H, m), 7.46 (1H, d, J=7.8 Hz).
ESI-MS (m/e): 421 [M+H]⁺.

Referential Example 41

Production of 2-[1-(4-benzylphenyl)-1,5-dihydro-3-methyl-5-oxo-4H-pyrazol-4-ylidene]-3,3,3-trifluoro-propanoic acid methyl ester The title compound was obtained as in Production Example 1 but using as the starting material 1-(4-benzylphenyl)-2,5-dihydro-α-hydroxy-3-methyl-5-oxo-α-trifluoromethyl-1H-pyrazole-4-acetic acid methyl ester.
¹HNMR (400 MHz, CDCl₃, δ ppm): 2.39 (3H, s), 3.98 (2H, s), 4.00 (3H, m), 6.91 (2H, d, J=8.8 Hz), 7.13-7.33 (8H, m), 7.70 (2H, d, J=8.8 Hz).
ESI-MS (m/e): 403 [M+H].

Referential Example 42

Production of 2,5-dihydro-α-hydroxy-1-(4-isopropoxyphenyl)-3-methyl-5-oxo-α-trifluoromethyl-1H-pyrazole-4-acetic acid methyl ester The title compound was obtained as in Production Example 1 but using as the starting material 4-isopropoxyphenylhydrazine.
¹HNMR (400 MHz, CDCl₃, δ ppm): 1.33 (6H, d, J=6.4 Hz) 2.39 (3H, s), 3.98 (3H, s), 4.00 (3H, s), 4.51-4.58 (1H, m), 6.91 (2H, d, J=9.3 Hz), 7.14-7.20 (1H, m), 7.46 (1H, d, J=7.8 Hz).
ESI-MS (m/e): 371 [M+H]⁺.

Referential Example 43

Production of 2-[1,5-dihydro-1-(4-isopropoxyphenyl)-3-methyl-5-oxo-4H-pyrazol-4-ylidene]-3,3,3-trifluoro-propanoic acid methyl ester The title compound was obtained as in Production Example 1 but using as the starting material 2,5-dihydro-α-hydroxy-1-(4-isopropoxyphenyl)-3-methyl-5-oxo-α-trifluoromethyl-1H-pyrazole-4-acetic acid methyl ester.
$^1$HNMR (400 MHz, CDCl$_3$, δ ppm): 2.41 (3H, s), 4.01 (3H, s), 4.50-4.58 (1H, m), 6.91 (2H, d, J=8.8 Hz), 7.15-7.20 (1H, m), 7.65 (2H, d, J=8.8 Hz).
ESI-MS (m/e): 405 [M+H]

Referential Example 44

Production of 2,5-dihydro-α-hydroxy-3-methyl-5-oxo-1-(4-phenoxyphenyl)-α-trifluoromethyl-1H-pyrazole-4-acetic acid methyl ester The title compound was obtained as in Production Example 1 but using as the starting material 4-phenoxyphenylhydrazine.
$^1$HNMR (400 MHz, CDCl$_3$, δ ppm): 2.30 (3H, s), 4.03 (3H, s), 4.05 (1H, s), 6.99-7.10 (4H, m), 7.30-7.37 (3H, m), 7.72-7.77 (2H, m).
ESI-MS (m/e): 423 [M+H]$^+$.

Referential Example 45

Production of 2-[1,5-dihydro-3-methyl-5-oxo-1-(4-phenoxyphenyl)-4H-pyrazol-4-ylidene]-3,3,3-trifluoro-propanoic acid methyl ester The title compound was obtained as in Production Example 1 but using as the starting material 2,5-dihydro-α-hydroxy-3-methyl-5-oxo-1-(4-phenoxyphenyl)-α-trifluoromethyl-1H-pyrazole-4-acetic acid methyl ester.
$^1$HNMR (400 MHz, CDCl$_3$, δ ppm): 2.41 (3H, s), 4.01 (3H, s), 6.97-7.09 (3H, m), 7.30-7.38 (4H, m), 7.73-7.77 (2H, m).
ESI-MS (m/e): 405 [M+H]

Referential Example 46

Production of 2,5-dihydro-α-hydroxy-3-methyl-5-oxo-1-(biphenyl-4-yl)-α-trifluoromethyl-1H-pyrazole-4-acetic acid methyl ester The title compound was obtained as in Production Example 1 but using as the starting material biphenyl-4-ylhydrazine.
$^1$HNMR (400 MHz, CDCl$_3$, δ ppm): 2.33 (3H, s), 4.01 (3H, s), 4.06 (1H, s), 7.33-7.39 (2H, m), 7.42-7.48 (4H, m), 7.56-7.67 (8H, m).
ESI-MS (m/e): 389 [M+H]$^+$.

Referential Example 47

Production of 2-[1,5-dihydro-3-methyl-5-oxo-1-(biphenyl-4-yl)-4H-pyrazol-4-ylidene]-3,3,3-trifluoro-propanoic acid methyl ester The title compound was obtained as in Production Example 1 but using as the starting material 2,5-dihydro-α-hydroxy-3-methyl-5-oxo-1-(biphenyl-4-yl)-α-trifluoromethyl-1H-pyrazole-4-acetic acid methyl ester.
$^1$HNMR (400 MHz, CDCl$_3$, δ ppm): 2.43 (3H, s), 4.03 (3H, s), 7.32-7.39 (2H, m), 7.41-7.68 (4H, m), 7.57-7.68 (8H, m).
ESI-MS (m/e): 389 [M+H]

Referential Example 48

Production of 1-(3,5-dichlorophenyl)-2,5-dihydro-α-hydroxy-3-methyl-5-oxo-α-trifluoromethyl-1H-pyrazole-4-acetic acid methyl ester The title compound was obtained as in Production Example 1 but using as the starting material 3,5-dichlorophenylhydrazine.
$^1$HNMR (400 MHz, CDCl$_3$, δ ppm): 2.31 (3H, s), 4.04 (3H, s), 4.06 (1H, s), 7.24 (1H, s), 7.86 (2H, d, J=4.0 Hz).
ESI-MS (m/e): 400 [M+H]$^+$.

Referential Example 49

Production of 2-[(3,5-dichlorophenyl)-1,5-dihydro-3-methyl-5-oxo-1-4H-pyrazol-4-ylidene]-3,3,3-trifluoro-propanoic acid methyl ester The title compound was obtained as in Production Example 1 but using as the starting material 1-(3,5-dichlorophenyl)-2,5-dihydro-α-hydroxy-3-methyl-5-oxo-α-trifluoromethyl-1H-pyrazole-4-acetic acid methyl ester.
$^1$HNMR (400 MHz, CDCl$_3$, δ ppm): 2.42 (3H, s), 4.03 (3H, s), 7.23 (1H, m), 8.12 (2H, d, J=9.3 Hz).
ESI-MS (m/e): 382 [M+H].

Referential Example 50

Production of 2,5-dihydro-α-hydroxy-3-methyl-1-(4-methylsulfonylphenyl)-5-oxo-α-trifluoromethyl-1H-pyrazole-4-acetic acid methyl ester The title compound was obtained as in Production Example 1 but using as the starting material 4-methylsulfonylphenylhydrazine.
$^1$HNMR (400 MHz, CDCl$_3$, δ ppm): 2.33 (3H, s), 3.06 (3H, s), 3.98 (3H, s), 4.08 (1H, s), 7.17 (2H, d, J=8.3 Hz), 7.98 (2H, d, J=9.0 Hz).
ESI-MS (m/e): 409 [M+H]$^+$.

Referential Example 51

Production of 2-[1,5-dihydro-3-methyl-1-(4-methylsulfonylphenyl)-5-oxo-4H-pyrazol-4-ylidene]-3,3,3-trifluoro-propanoic acid methyl ester The title compound was obtained as in Production Example 1 but using as the starting material 2,5-dihydro-α-hydroxy-3-methyl-1-(4-methylsulfonylphenyl)-5-oxo-α-trifluoromethyl-1H-pyrazole-4-acetic acid methyl ester.
$^1$HNMR (400 MHz, CDCl$_3$, δ ppm): 2.45 (3H, s), 3.07 (3H, s), 4.04 (3H, s), 7.98 (2H, d, J=9.3 Hz), 8.12 (2H, d, J=9.3 Hz).
ESI-MS (m/e): 310 [M+H].

INDUSTRIAL APPLICABILITY

Because of having excellent LCE inhibitory effect, the compounds according to the invention are useful as drugs for treating various diseases in which LCE participates, for example, circulatory diseases, neurological diseases, metabolic diseases, reproductive diseases, digestive tract diseases and so on.

The invention claimed is:

1. A compound represented by the general formula (I-a) or a pharmaceutically acceptable salt thereof:

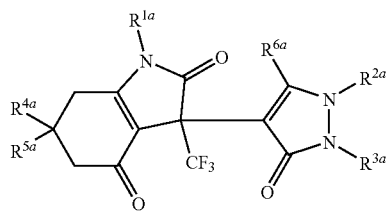

(I-a)

wherein $R^{1a}$ and $R^{2a}$ each independently represents a hydrogen atom, a $C_1$-$C_6$ alkyl group, an aryl group, a heteroaryl group or a $C_1$-$C_6$ alkyl group optionally substituted by a substituent selected from the group consisting of a $C_3$-$C_6$ cycloalkyl group, an aryl group and a heteroaryl group;

$R^{4a}$ and $R^{5a}$ each independently represents a $C_1$-$C_6$ alkyl group, a $C_3$-$C_6$ cycloalkyl group, an aryl group or an aralkyl group, or $R^{4a}$ and $R^{5a}$ may form a $C_3$-$C_6$ cycloalkylidene group together with the adjacent carbon atom;

$R^{6a}$ represents a $C_1$-$C_6$ alkyl group, a $C_1$-$C_6$ haloalkyl group, a $C_3$-$C_6$ cycloalkyl group or a $C_1$-$C_6$ alkoxy-$C_1$-$C_6$ alkyl group; wherein the above-described $C_3$-$C_6$ cycloalkyl group, $C_3$-$C_6$ cycloalkylidene group, aryl group, aralkyl group and heteroaryl group may be each independently substituted by a substituent selected from the group consisting of a halogen atom, a $C_1$-$C_6$ alkyl group, a $C_1$-$C_6$ haloalkyl group and a $C_1$-$C_6$ alkoxy group;

$R^{3a}$ represents a hydrogen atom, a $C_3$-$C_6$ cycloalkyl group, an aryl group, a heteroaryl group or a $C_1$-$C_6$ alkyl group optionally substituted by a substituent selected from the group consisting of a $C_3$-$C_6$ cycloalkyl group, an aryl group and a heteroaryl group, wherein the $C_3$-$C_6$ cycloalkyl group, aryl group and heteroaryl group in $R^{3a}$ each independently represents an unsubstituted group, a $C_3$-$C_6$ cycloalkyl group, an aryl group or a heteroaryl group substituted by one or two substituents selected from the group consisting of a halogen atom, a nitro group, a cyano group, a $C_1$-$C_6$ alkyl group, a $C_1$-$C_6$ haloalkyl group, a $C_1$-$C_6$ alkoxy group, a $C_1$-$C_6$ haloalkoxy group, a carboxyl group, a $C_3$-$C_6$ cycloalkyl group, an aryl group, a heteroaryl group, an aryloxy group, an aralkyl group, —CON($R^7$)$R^8$, —N($R^7$)$R^8$, —N($R^7$)COR$^8$, —N($R^7$)SO$_2$R$^8$, —OCOR$^7$, —OCON($R_7$)$R^8$, —SR$^7$, —SO$_2$N($R^7$)$R^8$ and

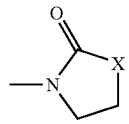

$R^7$ and $R^8$ each independently represents a hydrogen atom or a $C_1$-$C_6$ alkyl group; and X represents —N($R^7$)— or —O—(provided that in the case where $R^{2a}$ is a hydrogen atom, $R^{3a}$ is a phenyl group and $R^{4a}$, $R^{5a}$ and $R^{6a}$ are methyl groups, then $R^{1a}$ does not represent an n-butyl group, a phenyl group, a 4-fluorophenyl group, a 3-chlorophenyl group, a 3,4-dichlorophenyl group, a 4-methylphenyl group, a 3,4-dimethylphenyl group, a 3-trifluoromethylphenyl group, a 4-methoxyphenyl group, a furfuryl group, a benzyl group, a phenethyl group, a 4-fluorobenzyl group, a 2-chlorobenzyl group or a 3,4-dimethoxyphenethyl group.

2. A compound as claimed in claim 1 or a pharmaceutically acceptable salt thereof, wherein $R^{3a}$ is a phenyl group substituted by one or two substituents selected from the group consisting of a halogen atom, a nitro group, a cyano group, a $C_1$-$C_6$ alkyl group, a $C_1$-$C_6$ haloalkyl group, a $C_1$-$C_6$ alkoxy group, a $C_1$-$C_6$ haloalkoxy group, a carboxyl group, a $C_3$-$C_6$ cycloalkyl group, an aryl group, a heteroaryl group, an aryloxy group, an aralkyl group, —CON($R^7$)$R^8$, —N($R^7$)$R^8$, —N($R^7$)COR$_8$, —N($R^7$)SO$_2$R$^8$, —OCOR$^7$, —OCON($R^7$)$R^8$, —SR$^7$, —SO$_2$R$^7$, —SO$_2$N($R^7$)$R^8$ and

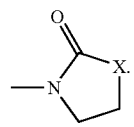

3. A compound as claimed in claim 1 or a pharmaceutically acceptable salt thereof, wherein $R^{1a}$ is a phenyl group, a cyclopropyl group, a cyclobutyl group, a cyclopentyl group, a cyclohexyl group, a propyl group, a 2-pyridylmethyl group, a 3-pyridylmethyl group, a 4-pyridylmethyl group, a 4-chlorophenyl group or a 3-methoxyphenyl group, or a salt or ester thereof.

4. A compound as claimed in claim 3 or a pharmaceutically acceptable salt thereof, wherein $R^{1a}$ is a cyclopropyl group, a cyclobutyl group, a cyclopentyl group, or a cyclohexyl group, or a salt or ester thereof 5. A compound as claimed in claim 1 which is:
1-(4-chlorophenyl)-3-(2,5-dihydro-3-methyl-5-oxo-1-phenyl-1H-pyrazol-4-yl)-3,5,6,7-tetrahydro-6,6-dimethyl-3-trifluoromethyl-1H-indole-2,4-dione,
3-(2,5-dihydro-3-methyl-5-oxo-1-phenyl-1H-pyrazol-4-yl)-3,5,6,7-tetrahydro-1-(3-methoxyphenyl)-6,6-dimethyl-3-trifluoromethyl-1H-indole-2,4-dione,
3-(2,5-dihydro-3-methyl-5-oxo-1-phenyl-1H-pyrazol-4-yl)-3,5,6,7-tetrahydro-1,6,6-trimethyl-3-trifluoromethyl-1H-indole-2,4-dione,
1-ethyl-3-(2,5-dihydro-3-methyl-5-oxo-1-phenyl-1H-pyrazol-4-yl)-3,5,6,7-tetrahydro-6,6-dimethyl-3-trifluoromethyl-1H-indole-2,4-dione,
3-(2,5-dihydro-3-methyl-5-oxo-1-phenyl-1H-pyrazol-4-yl)-3,5,6,7-tetrahydro-6,6-dimethyl-1-propyl-3-trifluoromethyl-1H-indole-2,4-dione,
3-(2,5-dihydro-3-methyl-5-oxo-1-phenyl-1H-pyrazol-4-yl)-3,5,6,7-tetrahydro-1-isopropyl-6,6-dimethyl-3-trifluoromethyl-1H-indole-2,4-dione,
1-cyclopropyl-3-(2,5-dihydro-3-methyl-5-oxo-1-phenyl-1H-pyrazol-4-yl)-3,5,6,7-tetrahydro-6,6-dimethyl-3-trifluoromethyl-1H-indole-2,4-dione,
1-cyclobutyl-3-(2,5-dihydro-3-methyl-5-oxo-1-phenyl-1H-pyrazol-4-yl)-3,5,6,7-tetrahydro-6,6-dimethyl-3-trifluoromethyl-1H-indole-2,4-dione,
1-cyclopentyl-3-(2,5-dihydro-3-methyl-5-oxo-1-phenyl-1H-pyrazol-4-yl)-3,5,6,7-tetrahydro-6,6-dimethyl-3-trifluoromethyl-1H-indole-2,4-dione, 1-cyclohexyl-3-(2,5-dihydro-3-methyl-5-oxo-1-phenyl-1H-pyrazol-4-yl)-3,5,6,7-tetrahydro-6,6-dimethyl-3-trifluoromethyl-1H-indole-2,4-dione,
3-(2,5-dihydro-3-methyl-5-oxo--phenyl-1H-pyrazol-4-yl)-3,5,6,7-tetrahydro-6,6-dimethyl-1 -(2-pyridylmethyl)-3-trifluoromethyl-1H-indole-2,4-dione,
3-(2,5-dihydro-3-methyl-5-oxo-1-phenyl-1H-pyrazol-4-yl)-3,5,6,7-tetrahydro-6,6-dimethyl-1-(3-pyridylmethyl)-3-trifluoromethyl-1H-indole-2,4-dione,
3-(2,5-dihydro-3-methyl-5-oxo-1-phenyl-1H-pyrazol-4-yl)-3,5,6,7-tetrahydro-6,6-dimethyl-1-(4-pyridylmethyl)-3-trifluoromethyl-1H-indole-2,4-dione,
3-(3-ethyl-2,5-dihydro-5-oxo-1-phenyl-1H-pyrazol-4-yl)-3,5,6,7-tetrahydro-6,6-dimethyl-1-phenyl-3 -trifluoromethyl-1H-indole-2,4-dione,
3-(3-cyclopropyl-2,5-dihydro-5-oxo-1-phenyl-1H-pyrazol-4-yl)-3,5,6,7-tetrahydro-6,6-dimethyl-1-phenyl-3-trifluoromethyl-1H-indole-2,4-dione,
3-(2,5-dihydro-5-oxo-1-phenyl-3-trifluoromethyl-1H -pyrazol-4-yl)-3,5,6,7-tetrahydro-6,6-dimethyl-1-phenyl-3-trifluoromethyl-1H-indole-2,4-dione,
3-[1-(3-chlorophenyl)-2,5-dihydro-3 -methyl-5-oxo-1H-pyrazol-4-yl]-3,5,6,7-tetrahydro-6,6-dimethyl-1-phenyl-3-trifluoromethyl-1H-indole-2,4-dione,
3-[1-(4-chlorophenyl)-2,5-dihydro-3-methyl-5-oxo-1H-pyrazol-4-yl]-3,5,6,7-tetrahydro-6,6-dimethyl- 1-phenyl-3-trifluoromethyl-1H-indole-2,4-dione,
3-[2,5-dihydro-1-(2-methoxyphenyl)-3-methyl-5-oxo-1H-pyrazol-4-yl]-3,5,6,7-tetrahydro-6,6-dimethyl-1-phenyl-3-trifluoromethyl-1H -indole-2,4-dione,
3-[2,5-dihydro-1-(3-methoxyphenyl)-3-methyl-5-oxo-1H-pyrazol-4-yl]-3,5,6,7-tetrahydro-6,6-dimethyl-3-trifluoromethyl-1H-indole-2,4-dione,
3-[2,5-dihydro-1-(4-methoxyphenyl)-3-methyl-5-oxo-1H-pyrazol-4-yl]-1-phenyl-3,5,6,7-tetrahydro-6,6-dimethyl-3-trifluoromethyl- 1H-indole-2,4-dione,
3-(2,5-dihydro-3-methyl-5-oxo-1-phenyl-1H-pyrazol-4-yl)-3,5,6,7-tetrahydro-6-methyl-1-phenyl-3-trifluoromethyl-1H-indole-2,4-dione,
3'-(2,5-dihydro-3-methyl-5-oxo-1-phenyl-1H-pyrazol-4-yl)- 1'-phenyl-3'-trifluoromethyl-3',7'-dihydrospiro[cyclobutan-1,6'-indole]-2',4'(1'H,5'H)-dione,
3-[2,5-dihydro-3-methyl-5-oxo-1-(4-trifluoromethylphenyl)- 1H-pyrazol-4-yl]-3,5,6,7-tetrahydro-6,6-dimethyl-1-phenyl-3-trifluoromethyl-1H -indole-2,4-dione,
3-[1-(4-fluorophenyl)-2,5-dihydro-3-methyl-5-oxo-1H-pyrazol-4-yl]-3,5,6,7-tetrahydro-6,6-dimethyl- 1-phenyl-3-trifluoromethyl- 1H-indole-2,4-dione,
3-[1-(4-cyanophenyl)-2,5-dihydro-3-methyl-5-oxo-1H-pyrazol-4-yl]-3,5,6,7-tetrahydro-6,6-dimethyl- 1-phenyl-3-trifluoromethyl-1H-indole-2,4-dione,
3-[2,5-dihydro-1-(4-isopropylphenyl)-3-methyl-5-oxo-1H-pyrazol-4-yl]-3,5,6,7-tetrahydro-6,6-dimethyl-1-phenyl-3-trifluoromethyl-1H-indole-2,4-dione,
3-[2,5-dihydro-3-methyl-1-(4-methylphenyl)-5-oxo-1H-pyrazol-4-yl]-3,5,6,7-tetrahydro-6,6-dimethyl-1-phenyl-3-trifluoromethyl-1H-indole-2,4-dione,
3-[1-(4-aminosulfonylphenyl)-2,5-dihydro-5-oxo-1H-pyrazol-4-yl]-3,5,6,7-tetrahydro-6,6-dimethyl-1-phenyl-3-trifluoromethyl-1H-indole-2,4-dione,
3-[1-(4-tert-butylphenyl)-2,5-dihydro-3-methyl-5-oxo-1H-pyrazol-4-yl]-3,5,6,7-tetrahydro-6,6-dimethyl-1-phenyl-3-trifluoromethyl-1H-indole-2,4-dione,
3-[2,5-dihydro-3-methyl-5-oxo-1-(4-trifluoromethoxyphenyl)-1H-pyrazol-4-yl]-3,5,6,7-tetrahydro-6,6-dimethyl-1-phenyl-3-trifluoromethyl -1H-indole-2,4-dione,
3-(2,5-dihydro-3-methyl-1-(3,5-dimethylphenyl)-5-oxo-1H-pyrazol-4-yl) -3,5,6,7-tetrahydro-6,6-dimethyl-1-phenyl-3-trifluoromethyl-1H-indole-2,4-dione,
3-[1-(4-cyclohexylphenyl)-2,5-dihydro-3-methyl-5-oxo-1H-pyrazol-4-yl]-3,5,6,7-tetrahydro-6,6-dimethyl-1-phenyl-3-trifluoromethyl-1H-indole-2,4-dione,
3-[1-(4-benzylphenyl)-2,5-dihydro-3-methyl-5-oxo-1H-pyrazol-4-yl]-3,5,6,7-tetrahydro-6,6-dimethyl-1-phenyl-3-trifluoromethyl-1H-indole-2,4-dione,
3-[2,5-dihydro-1-(4-isopropoxylphenyl)-3-methyl-5-oxo-1H-pyrazol-4-yl]-3,5,6,7-tetrahydro-6,6-dimethyl-1-phenyl-3-trifluoromethyl-1H-indole-2,4-dione,
3-[2,5-dihydro-3-methyl-5-oxo-1-(4-phenoxyphenyl)-1H-pyrazol-4-yl]-3,5,6,7-tetrahydro-6,6-dimethyl-1-phenyl-3-trifluoromethyl-1H-indole-2,4-dione,
3-[2,5-dihydro-3-methyl-5-oxo-1-(biphenyl-4-yl)-1H-pyrazol-4-yl]-3,5,6,7-tetrahydro-6,6-dimethyl-1-phenyl-3-trifluoromethyl-1H-indole-2,4-dione,
3-[1-(3,5-dichlorophenyl)-2,5-dihydro-3-methyl-5-oxo-1H-pyrazol-4-yl]-3,5,6,7-tetrahydro-6,6-dimethyl-1-phenyl-3-trifluoromethyl-1H-indole-2,4-dione or
3-[2,5-dihydro-3-methyl-(4-methylsulfonylphenyl)-5-oxo-1-1H-pyrazol-4-yl]-3,5,6,7-tetrahydro-6,6-dimethyl-1-phenyl-3-trifluoromethyl-1H-indole-2,4-dione,
or a pharmaceutically acceptable salt thereof.

6. A method of treating diabetes comprising administering to a subject in need thereof a long chain fatty acyl elongase (LCE) inhibitor comprising a compound represented by the general formula (I) or a pharmaceutically acceptable salt thereof:

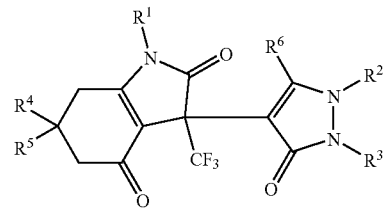

(I)

wherein $R^1$ and $R^2$ each independently represents a hydrogen atom, a $C_3$-$C_6$ cycloalkyl group, an aryl group, a heteroaryl group or a $C_1$-$C_6$ alkyl group optionally substituted by a substituent selected from the group consisting of a $C_3$-$C_6$ cycloalkyl group, an aryl group and a heteroaryl group;

$R^4$ and $R^5$ each independently represents a $C_1$-$C_6$ alkyl group, a $C_3$-$C_6$ cycloalkyl group, an aryl group or an aralkyl group, or $R^4$ and $R^5$ may form a $C_3$-$C_6$ cycloalkylidene group together with the adjacent carbon atom;

$R^6$ represents a $C_1$-$C_6$ alkyl group, a $C_1$-$C_6$ haloalkyl group, a $C_3$-$C_6$ cycloalkyl group or a $C_1$-$C_6$ alkoxy-$C_1$-$C_6$ alkyl group; wherein the above-described $C_3$-$C_6$ cycloalkyl group, $C_3$-$C_6$ cycloalkylidene group, aryl group, aralkyl group and heteroaryl group may be each independently substituted by a substituent selected from the group consisting of a halogen atom, a $C_1$-$C_6$ alkyl group, a $C_1$-$C_6$ haloalkyl group and a $C_1$-$C_6$ alkoxy group;

$R^3$ represents a hydrogen atom, a $C_3$-$C_6$ cycloalkyl group, an aryl group, a heteroaryl group or a $C_1$-$C_6$ alkyl group optionally substituted by a substituent selected from the group consisting of a $C_3$-$C_6$ cycloalkyl group, an aryl group and a heteroaryl group, wherein the $C_3$-$C_6$ cycloalkyl group, aryl group and heteroaryl group in $R^3$ each independently represents an unsubstituted group or a $C_3$-$C_6$ cycloalkyl group, an aryl group or a heteroaryl group substituted by one or two substituents selected from the group consisting of a halogen atom, a nitro group, a cyano group, a $C_1$-$C_6$ alkyl group, a $C_1$-$C_6$ haloalkyl group, a $C_1$-$C_6$ alkoxy group, a $C_1$-$C_6$ haloalkoxy group, a carboxyl group, a $C_3$-$C_6$ cycloalkyl group, an aryl group, a heteroaryl group, an aryloxy group, an aralkyl group, —CON($R^7$)$R^8$—N($R^7$)$R^8$, —N($R^7$)COR$^8$, —N($R^7$)SO$_2$R$^8$, —OCOR$^7$, —OCOR$^7$, —OCON($R^7$)$R^8$, —SR$^7$, —SR$_2$R$^7$, —SO$_2$N($R^7$)$R^8$ and

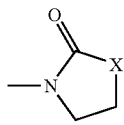

$R^7$ and $R^8$ each independently represents a hydrogen atom or a $C_1$-$C_6$ alkyl group; and X represents —N($R^7$)— or —O—.

7. A long chain fatty acyl elongase (LCE) inhibitor as claimed in claim 6 wherein, in the compound of the general formula (I) or a pharmaceutically acceptable salt thereof, $R^2$ is a hydrogen atom, $R^3$ is a phenyl group and $R^4$, $R^5$ and $R^6$ are methyl groups.

8. A long chain fatty acyl elongase (LCE) inhibitor as claimed in claim 7 wherein, in the compound of the general formula (I) or a pharmaceutically acceptable salt thereof, $R^1$ is a phenyl group, a benzyl group, a 3-chlorophenyl group, a 4-fluorophenyl group or a 4-methoxyphenyl group.

9. A long chain fatty acyl elongase (LCE) inhibitor as claimed in claim 6 wherein, in the compound of the general formula (I) or pharmaceutically acceptable salt thereof, $R^3$ is a phenyl group substituted by one or two substituents selected from the group consisting of a halogen atom, a nitro group, a cyano group, a $C_1$-$C_6$ alkyl group, a $C_1$-$C_6$ haloalkyl group, a $C_1$-$C_6$ alkoxy group, a $C_1$-$C_6$ haloalkoxy group, a carboxyl group, a $C_3$-$C_6$ cycloalkyl group, an aryl group, a heteroaryl group, an aryloxy group, an aralkyl group, —CON($R^7$)$R^8$, —N($R^7$)$R^8$, —N($R^7$)COR$^8$, —N($R^7$)SO$_2$R$^8$, —OCOR$^7$, —OCON($R^7$)$R^8$, —SR$^7$, —SO$_2$R$^7$, —SO$_2$N($R^7$)$R^8$ and

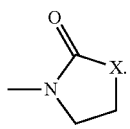

10. A long chain fatty acyl elongase (LCE) inhibitor as claimed in claim 6 wherein, in the compound of the general formula (I) or pharmaceutically acceptable salt thereof, $R^1$ is a cyclopropyl group, a cyclobutyl group, a cyclopentyl group, a cyclohexyl group, a propyl group, a 2-pyridylmethyl group, a 3-pyridylmethyl group, a 4-pyridylmethyl group, a 4-chlorophenyl group or a 3-methoxyphenyl group.

11. A long chain fatty acyl elongase (LCE) inhibitor as claimed in claim 10 wherein, in the compound of the general formula (I) or pharmaceutically acceptable salt thereof, $R^1$ is a cyclopropyl group, a cyclobutyl group, a cyclopentyl group or a cyclohexyl group.

12. A long chain fatty acyl elongase (LCE) inhibitor as claimed in claim 6 which comprises a compound selected from:

3-(2,5-dihydro-3-methyl-5-oxo-1-phenyl-1H-pyrazol-4-yl)-3,5,6,7-tetrahydro -6,6-dimethyl-1-phenyl-3-trifluoromethyl-1H-indole-2,4-dione, 3-(2,5-dihydro-3-methyl-5-oxo-1-phenyl-1H-pyrazol-4-yl)-3,5,6,7-tetrahydro -6,6-dimethyl-1-phenylmethyl-3-trifluoromethyl-1H-indole-2,4-dione, 1-(4-fluorophenyl)-3-(2,5-dihydro-3-methyl-5-oxo-1-phenyl-1H-pyrazol-4-yl)-3,5,6,7-tetrahydro-6,6-dimethyl-3-trifluoromethyl-1H-indole-2,4-dione, 3-(2,5-dihydro-3-methyl-5-oxo-1-phenyl-1H-pyrazol-4-yl)-3,5,6,7-tetrahydro -1-(4-methoxyphenyl)-6,6-dimethyl-3-trifluoromethyl-1H-indole-2,4-dione, or 1-(3-chlorophenyl)-3-(2,5-dihydro-3-methyl-5-oxo-1-phenyl-1H-pyrazol-4-yl)-3,5,6,7-tetrahydro-6,6-dimethyl-3-trifluoromethyl-1H-indole-2,4-dione, or pharmaceutically acceptable salt thereof.

13. A medicinal composition comprising a therapeutically effective amount of a compound represented by the general formula (I) or pharmaceutically acceptable salt thereof, and a pharmaceutically acceptable additive:

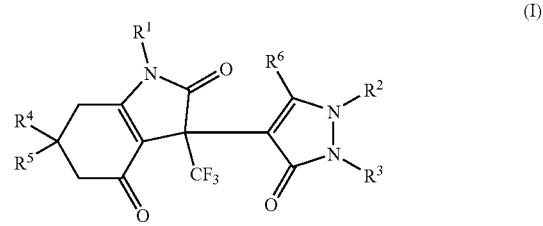

(I)

wherein $R^1$ and $R^2$ each independently represents a hydrogen atom, a $C_3$-$C_6$ cycloalkyl group, an aryl group, a heteroaryl group or a $C_1$-$C_6$ alkyl group optionally substituted by a substituent selected from the group consisting of a $C_3$-$C_6$ cycloalkyl group, an aryl group and a heteroaryl group;

$R^4$ and $R^5$ each independently represents a $C_1$-$C_6$ alkyl group, a $C_3$-$C_6$ cycloalkyl group, an aryl group or an aralkyl group, or $R^4$ and $R^5$ may form a $C_3$-$C_6$ cycloalkylidene group together with the adjacent carbon atom;

$R^6$ represents a $C_1$-$C_6$ alkyl group, a $C_1$-$C_6$ haloalkyl group, a $C_3$-$C_6$ cycloalkyl group or a $C_1$-$C_6$ alkoxy-$C_1$-$C_6$ alkyl group; wherein the above-described $C_3$-$C_6$ cycloalkyl group, lower cycloalkylidene group, aryl group, aralkyl group and heteroaryl group may be each independently substituted by a substituent selected from the group consisting of a halogen atom, a $C_1$-$C_6$ alkyl group, a $C_1$-$C_6$ haloalkyl group and a $C_1$-$C_6$ alkoxy group;

$R^3$ represents a hydrogen atom, a $C_3$-$C_6$ cycloalkyl group, an aryl group, a heteroaryl group or a $C_1$-$C_6$ alkyl group optionally substituted by a substituent selected from the group consisting of a $C_3$-$C_6$ cycloalkyl group, an aryl group and a heteroaryl group, wherein the $C_3$-$C_6$ cycloalkyl group, aryl group and heteroaryl group in $R^3$ each independently represents an unsubstituted group or a $C_3$-$C_6$ cycloalkyl group, an aryl group or a heteroaryl group substituted by one or two substituents selected from the group consisting of a halogen atom, a nitro group, a cyano group, a $C_1$-$C_6$ alkyl group, a $C_1$-$C_6$ haloalkyl group, a C₁-C₆ alkoxy group, a C₁-C₆ haloalkoxy group, a carboxyl group, a C₃-C₆ cycloalkyl group, an aryl group, a heteroaryl group, an aryloxy group, an aralkyl group, —CON(R⁷)R⁸, —N(R⁷)R⁸, —N(R⁷)SO₂R⁸, —OCOR⁷, —OCON(R⁷)R⁸, —SR⁷, —SO₂R⁷, —SO₂N(R⁷)R⁸ and

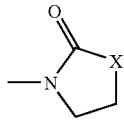

wherein R⁷ and R⁸ each independently represents a hydrogen atom or a C₁-C₆ alkyl group; and X represents —N(R⁷)— or —O—.

14. A medicinal composition as claimed in claim 13 wherein, in the compound of the general formula (I) or pharmaceutically acceptable salt thereof, R² is a hydrogen atom, R³ is a phenyl group and R⁴, R⁵ and R⁶ are methyl groups.

15. A medicinal composition as claimed in claim 14 wherein, in the compound of the general formula (I) or pharmaceutically acceptable salt thereof, R¹ is a phenyl group, a benzyl group, a 3-chlorophenyl group, a 4-fluorophenyl group or a 4-methoxyphenyl group.

16. A medicinal composition as claimed in claim 13 wherein, in the compound of the general formula (I) or pharmaceutically acceptable salt thereof, R³ is a phenyl group substituted by one or two substituents selected from the group consisting of a halogen atom, a nitro group, a cyano group, a C₁-C₆ alkyl group, a C₁-C₆ haloalkyl group, a C₁-C₆ alkoxy group, a C₁-C₆ haloalkoxy group, a carboxyl group, a C₃-C₆ cycloalkyl group, an aryl group, a heteroaryl group, an aryloxy group, an aralkyl group, —CON(R⁷)R⁸, —N(R⁷)R⁸, —N(R⁷)SO₂R⁸, —OCOR⁷, —OCON(R⁷)R⁸, —SR⁷, —SO₂R⁷, —SO₂N(R⁷)R⁸ and

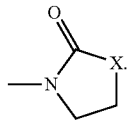

17. A medicinal composition as claimed in claim 13 wherein, in the compound of the general formula (I) or pharmaceutically acceptable salt thereof, R¹ is a cyclopropyl group, a cyclobutyl group, a cyclopentyl group, a cyclohexyl group, a propyl group, a 2-pyridylmethyl group, a 3-pyridylmethyl group, a 4-pyridylmethyl group, a 4-chlorophenyl group or a 3-methoxyphenyl group.

18. A medicinal composition as claimed in claim 17 wherein, in the compound of the general formula (I) or pharmaceutically acceptable salt thereof, R¹ is a cyclopropyl group, a cyclobutyl group, a cyclopentyl group or a cyclohexyl group.

19. A drug for treating diabetes, obesity or non-alcoholic fatty liver which comprises a medicinal composition as claimed in claim 13.

20. A medicinal composition as claimed in claim 13 which comprises a compound selected from:
   3-(2,5-dihydro-3-methyl-5-oxo-1-phenyl-1H-pyrazol-4-yl)-3,5,6,7-tetrahydro-6,6-dimethyl-1-phenyl-3-trifluoromethyl-1H-indole-2,4-dione,
   3-(2,5-dihydro-3-methyl-5-oxo-1-phenyl-1H-pyrazol-4-yl)-3,5,6,7-tetrahydro-6,6-dimethyl-1-phenylmethyl-3-trifluoromethyl-1H-indole-2,4-dione,
   1-(4-fluorophenyl)-3-(2,5-dihydro-3-methyl-5-oxo-1-phenyl-1H-pyrazol-4-yl)-3,5,6,7-tetrahydro-6,6-dimethyl-3-trifluoromethyl-1H-indole-2,4-dione,
   3-(2,5-dihydro-3-methyl-5-oxo-1-phenyl-1H-pyrazol-4-yl)-3,5,6,7-tetrahydro-1-(4-methoxyphenyl)-6,6-dimethyl-3-trifluoromethyl-1H-indole-2,4-dione, or
   1-(3-chlorophenyl)-3-(2,5-dihydro-3-methyl-5-oxo-1-phenyl-1H-pyrazol-4-yl)-3,5,6,7-tetrahydro-6,6-dimethyl-3-trifluoromethyl-1H-indole-2,4-dione,
or pharmaceutically acceptable salt thereof, and a pharmaceutically acceptable additive.

* * * * *

UNITED STATES PATENT AND TRADEMARK OFFICE
CERTIFICATE OF CORRECTION

PATENT NO. : 8,106,086 B2
APPLICATION NO. : 12/532182
DATED : January 31, 2012
INVENTOR(S) : Toshiyuki Takahashi et al.

It is certified that error appears in the above-identified patent and that said Letters Patent is hereby corrected as shown below:

In the Claims:

Column 65, Line 55 should appear as follows:

(R7)R8, -SR7, -SO2R7, -SO2N(R7)R8 and

Column 69, Line 14 should appear as follows:

-OCON(R7)R8, -SR7, -SO2R7, -SO2N(R7)R8 and

Column 71, Lines 5 should appear as follows:

-N(R7)COR8, -N(R7)SO2R8, -OCOR7, -OCON(R7)R8, -SR7.

Signed and Sealed this
Sixteenth Day of July, 2013

Teresa Stanek Rea
*Acting Director of the United States Patent and Trademark Office*